(12) United States Patent
Shiki et al.

(10) Patent No.: US 6,419,632 B1
(45) Date of Patent: Jul. 16, 2002

(54) HIGH RESOLUTION FLOW IMAGING FOR ULTRASOUND DIAGNOSIS

(75) Inventors: Eiichi Shiki, Otawara; Yoshitaka Mine, Tochigi-Ken, both of (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/539,322

(22) Filed: Mar. 30, 2000

(30) Foreign Application Priority Data

Mar. 30, 1999 (JP) .......................................... 11-090293

(51) Int. Cl.[7] ................................................. A61B 8/00
(52) U.S. Cl. ...................................................... 600/443
(58) Field of Search ........................ 600/437, 440–441, 600/443, 447, 450–458; 73/625, 626

(56) References Cited

U.S. PATENT DOCUMENTS

| | | |
|---|---|---|
| 4,809,249 A | 2/1989 | Barnes |
| 4,928,698 A | 5/1990 | Bonnefous |
| 4,930,513 A * | 6/1990 | Mayo et al. ................ 600/455 |
| 5,913,824 A * | 6/1999 | Ogasawara et al. ......... 600/455 |

* cited by examiner

*Primary Examiner*—Francis J. Jaworski
*Assistant Examiner*—Ali M. Imam
(74) *Attorney, Agent, or Firm*—Oblon, Spivak, McClelland, Maier & Neustadt, P.C.

(57) ABSTRACT

In a high-resolution flow mode, a diagnostic ultrasound apparatus and a diagnostic ultrasound method that provide an image of blood flow or perfusion is provided with higher sensitivity and high resolution, which makes it possible to precisely observe the presence of fine blood vessels. In this apparatus, by scanning means (81 to 83), with a ultrasound pulse having a wideband frequency characteristic transmitting at least two times in the same direction within an object, a cross section to be imaged therein is scanned to obtain an echo signal at each time of transmission. By processing means 84, highpass filtering or differential processing is performed with rows of data in the time axis direction of an echo signal acquired at each sample location in the cross section, so that signals from blood flow are extracted. By producing means 85, the processed signals are produced into data of luminance or power. This data is displayed by displaying means 86 as a high-resolution color (flow) image or grayscale flow image indicative of blood flow or perfusion.

36 Claims, 39 Drawing Sheets

CONVENTIONAL METHOD
(a) PRIOR ART (b) METHOD ON PRESENT INVENTION (a) SCREEN DISPLAYED ON MONITOR (c) COLOR BAR(VELOCITY)

(b) COLOR BAR(VELOCITY)

(d) COLOR BAR(VELOCITY)

(e) COLOR BAR(POWER)

(a) CONVENTIONAL DOPPLER VELOCITY IMAGE
PRIOR ART (b) DOPPLER VELOCITY IMAGE WHEREIN BLOOMING IS OCCURED BY CONTRAST AGENT INJECTION (a) CONVENTIONAL DOPPLER VELOCITY IMAGE
PRIOR ART

(b) HIGH-RESOLUTION FLOW IMAGE (a) CONVENTIONAL DOPPLER VELOCITY IMAGE
PRIOR ART (b) HIGH-RESOLUTION FLOW IMAGE (a) CONVENTIONAL DOPPLER VELOCITY IMAGE
PRIOR ART

(b) HIGH-RESOLUTION FLOW IMAGE

HIGH RESOLUTION FLOW IMAGING FOR ULTRASOUND DIAGNOSIS

BACKGROUND OF THE INVENTION

1. Field of the Invention

The present invention relates to a diagnostic ultrasound apparatus and a method of diagnosis with ultrasound images capable of visualizing images of blood flow as an element in motion in an object to be imaged at a higher degree of resolution and high sensitivity, and in particular, to the apparatus and method preferable to an contrast echo technique performed with an ultrasound contrast agent injected into an object for acquiring blood flow images.

2. Description of the Related Art

A diagnostic ultrasound apparatus has a wide variety of advantages, such as, relatively compact in size, lower price, no X-ray exposure, and availability of blood flow imaging on an ultrasound Doppler technique, thereby providing an indispensable today's imaging modality in the field of clinics.

Particularly, the blood flow imaging on the ultrasound Doppler technique, which functions strongly in finding lesions in the cardiac system and others, is called color flow mapping (CFM) or color Doppler tomography and has been standardized in almost all the diagnostic ultrasound apparatus. This color flow mapping two-dimensionally displays blood flow information in almost real time, where a flow toward an ultrasound probe is displayed in red, while a flow away from the probe is displayed in blue.

To perform such display, it is required that the same location in an object be ultrasound-scanned a plurality of times, N, to acquire a time-sequential echo signal and a velocity of blood cells at a desired depth location is detected from the echo signal on the Doppler technique. That is, a Doppler signal is derived from an amount of phase shift per unit time of a reflected signal (blood flow signal) originated from blood cells through scanning of the same location at intervals, and converted into a velocity of blood flow.

In an echo signal associated with ultrasound scanning at each time, there are mixed of a reflected wave from moving substances such as blood cells and another reflected wave from stationary substances, such as the wall of a blood vessel and tissue, which scarcely move. It is characteristic that the latter is dominant in reflected intensity, but there occurs almost no Doppler shift in the reflected wave (clutter signal) from the stationary reflection. members belonging to the latter, while the former has the Doppler shift therein. Thus a Doppler signal is extracted from the echo signal by a quadrature phase detector (comprising a mixer and an LPF), and a blood flow Doppler signal is efficiently extracted by an MTI filter which removes a clutter signal component from the Doppler signal on differences in Doppler shift amounts. The blood flow Doppler signal then experiences frequency analysis carried out using N-piece Doppler data at each depth location, producing an average of the spectrum. (Doppler frequency), dispersion, or reflection intensity from blood cells. The Doppler frequency $f_d$ is converted into a Doppler velocity $v_d$ according to this formula:

$$v_d = f_d \cdot c / (2 f_M \cdot \cos\theta) \qquad (1),$$

wherein c denotes a sound velocity, $f_M$ does the frequency of a reference signal in the mixer, $\theta$ does an angle made between an ultrasound beam and blood flow. This information about blood flow thus-obtained is, in general, two-dimensionally displayed on a monitor, with a B-mode image employed as a background.

A CFM mode used in performing this color flow mapping (CFM) will now be compared with a B mode in terms of resolution, S/N, dynamic range for display, aliasing frequency, realtime performance, and others.

The number of burst waves associated with transmitted ultrasound waves differs between the B mode and CFM mode. The burst wave number is defined as the number, per cycle, of ultrasound pulses having the length of a transmission repetition $T_0$ that is the inverse of an ultrasound transmission frequency $f_0$.

The B mode is directed to observing a tomographic image, that is, an image composed of ultrasound signals echoed from tissue. The reflected signal from the tissue is able to have a satisfactorily high S/N, because the reflected signal can be detected at fully large signal intensities within a range of ultrasound pressures which are determined with consideration of safety for an object to be diagnosed. Hence the burst wave number can be set to a lower value, such as one to two waves, and a range resolution can be increased satisfactorily, fulfilling both the S/N and range resolution.

By contrast, the CFM mode is used for observing blood flow, which corresponds therefore to a reflected signal from blood cells (blood flow signal). This blood flow signal is considerably less in signal intensity, approximately −40 to −80 dB, than that acquired from the tissue. Under the same transmission pulse condition as that in the B mode, the CFM mode provides an inferior S/N, with blood flow information substantially unavailable.

The S/N can therefore be improved by increasing the power of an ultrasound pulse to be transmitted. However, in general, since the transmitted ultrasound pressure has a limitation that has been determined with consideration of safety for an object in the B mode, it is difficult to raise the pressure any more. As a result, the number of burst waves is determined at a larger value, such as three waves or more, to enhance power of the ultrasound pulse to be transmitted. An excessively large burst wave number cause, however, range resolution to be deteriorated, thus an upper limit of the burst wave number being determined dependently on an allowed value of the range resolution.

Although the S/N of the blood flow signal can be improved in this way, the power of the blood flow signal still remain smaller by approx. a few dozes of dB than the power of a single reflected from tissue, even when the burst wave number would be raised up to the upper limit within the tolerance thereof. This causes differences in dynamic ranges for display. The dynamic range for B-mode display is large; for example, 100 dB in maximum, although the dynamic rage for the power mode displaying power under the CFM mode is small; for example, 40 dB in maximum.

The ultrasound pulse is repetitively transmitted at a pulse repetition time $T_r$. Thus in the velocity mode displaying Doppler velocities under the CFM mode, an aliasing phenomenon will occur, due to the sampling theory, at $\pm f_r/2$ which is half the pulse repetition frequency $f_r = 1/Tr$ inverted from the pulse repetition time. The values of $\pm f_r/2$ are referred to as aliasing frequencies. The sign ± means that the direction is separated. From the foregoing equation (1), an aliasing velocity $v_r/2$ corresponding to the aliasing frequencies is obtained as follows, by setting $\theta=0$:

$$v_r/2 = (f_r/2) \cdot (c/2 f_M) \qquad (2).$$

Because c and $f_M$ are constant, the aliasing velocity $v_r/2$ becomes constant as well. This aliasing velocity is normally displayed, for diagnosis, on a TV monitor together with a two-dimensional image indicative of blood flow information.

In the B mode, a tomographic image is obtained by performing one time transmission and reception of an ultrasound pulse along the same raster (beam) direction, while in the CFM mode, imaging is based on Doppler signals obtained by performing the transmission and reception of an ultrasound pulse a plurality of times along the same raster direction. Thus, the CFM mode is largely lowered in frame rate than the B mode. For instance, where the transmission and reception is desired to be repeated sixteen times in the same direction, the transmission and reception is required to be repeated seventeen times in total, including scanning of the B mode. If the number of frames for the B mode is ten frames per sec., the number for the CFM mode is six frames per sec., thereby reducing realtime performance.

As a countermeasure to improve the realtime performance in the CFM mode, a technique called "parallel simultaneous reception" has now been in practical use, where the transmission is performed in one direction and the reception is performed simultaneously in a plurality of directions. However, this parallel simultaneous reception technique requires a transmitted beam to be spread, which reduces power transmitted to each sample position (depth position) in an object, ultimately lowering detection sensitivity. Since the safety standard regulates the transmitted power not to exceed a given value, performing the parallel simultaneous reception generally reduces the detection sensitivity. Therefore, the CFM mode, which is in charge of imaging signals of lower sensitivities, i.e., blood flow signals, has a limitation in using the parallel simultaneous reception technique. Namely, a portion to be diagnosed is confined to portions having relatively higher sensitivities, such as ventricles. The parallel simultaneous reception technique is still effective in improving realtime performance, but this technique is not a way that can always be used regardless of portions to be diagnosed.

On one hand, to diagnose tumor or ischemic heart illness, there has been a strong need that one would like to detect blood vessels as thinner as possible, like seen in detecting blood flow in tumor or blood flow of the coronary. In the conventional CFM mode, the following countermeasures to improve sensitivity was planned, in addition to enhance the fundamental performance of an apparatus by adopting higher-performance components.

Namely, the detection on the power mode has been improved recently, and is superior in sensitivity than the velocity mode. The reason is as follows.

In the velocity mode, because a flow of which velocity is almost zero or a flow intersecting an ultrasound beam becomes back when it is visualized, which means the velocity is not practically shown. In the case of the improved power mode, those types of blood flow are visualized based on the strength of their power, providing greater detectability in lower-velocity flows.

Moreover, in the velocity mode, a signal whose intensity is less than a given value is always regarded as noise and is avoided from being displayed, even if it is a blood flow signal. On one hand, according to the improved power mode, even when signal power is weak, it is displayed at a lowered luminance. And a spatial connection of signals is considered into whether the signals are from blood flow, with the result that blood flow of which sensitivity is low is easy to detect.

Though the improved power mode has owned such enhanced sensitivity, the imaging conditions of the conventional CFM mode are applied to the improved power mode. Potential ability of the improved power mode has not been shown fully yet. For example, the number of transmission burst waves still remains as conventional, thus lowering spatial resolution. As a result, a thin blood vessel is displayed as being thick one or adjoining blood vessels are displayed without being separated, only having shown poor diagnosis performance.

Under the circumstances, an evaluation of blood flow utilizing an ultrasound contrast agent has been tried recently. Since the ultrasound contrast agent (hereinafter, referred to as a contrast agent) enhances the scattering intensity of ultrasound signals when it is administered into a blood vessel of an object, it has been expected to obtain blood flow images of superior diagnosis performance with the use of the enhancement effect. For a recent few years, in particular, the contrast agent has been remarkably increased in its performance and has upgraded its contrast effect, in addition to lowered invasiveness due to the fact that the contrast agent is possible to administer from the vein, it seems that the contrast agent will become more and more popular from now. Associated with this fact, there is a need that a diagnostic ultrasound apparatus should has a function to perform diagnosis making use of the features of the contrast agent improved year by year.

In the case that blood flows of an object into which this contrast agent is injected are observed with the conventional diagnostic ultrasound apparatus, the following various problems has remained unsolved at present, to one's regret.

The contrast agent is injected into an object to enhance the sensitivity of blood flow signals. Practically, such agent is administered from the body surface to the vein or from a catheter to the artery, and flows into each organ through the heart and/or large arteries. The primary constituent of the contrast agent consists of microbubbles having a diameter of approx. a few microns, and is greatly higher in scattering intensity than the blood cells ( for example, it is higher by a few dozes of decibels). Injecting this constant medium allows blood flow signals (in detail, echo signals that are reflected from the contrast agent flowing through blood vessels) to be enhanced largely up to a comparable level with echo signals emanated from tissue. It seems that this enhancement makes it possible to detect blood vessels whose diameters are thin or which exist deeply, which have been undetectable so far.

However, in a practical use, there has been reported that a phenomenon called "blooming" occurs in which a blood flow is displayed with its picture creeping out largely, compared to the diameter of a blood vessel displayed in the B mode. FIG. 38($a$) illustrates an example of an ordinary Doppler velocity image which depicts a blood vessel B, while FIG. 38($b$) does an example of a Doppler velocity image in which there occurs the blooming due to the injection of a contrast agent. The blooming, when it occurs, extremely deteriorates the spatial resolution, thus practical diagnosis being almost impossible.

It is considered that the blooming will occur by the following reasons. Assume that the pulse length of an ultrasound pulse to be transmitted is assigned to a value determined by the number of burst waves, M (positive integer) and a transmission frequency $f_0$. The pulse length at a time when being outputted from a transmission circuit becomes $M/f_0$. An ultrasound pulse of such pulse length is transmitted and received by way of a probe, during which time a received pulse dulls along its time-axis direction, that is, the depth direction, thus spreading, owing to frequency-dependent loss of an object and/or the band characteristic of the probe. Additionally, during the reception to display, the received signal undergoes processing using filters for a variety of types of processing. This filtering processing causes the waveform of the received pulse to dull, thus making it further spread in the time-axis direction.

By contrast, when the contrast agent is not used, the spreading is limited to a little amount. It is considered that the reason is as follows. A blood flow signal is low in intensity, which is an amount slightly larger than an apparatus noise level. The spread roots of a received pulse are mostly less than the noise level, while the remaining pulse portion of which strength is over the noise level keeps amounts slightly larger than the $M/f_0$, or slightly lower that it, in some cases. Normally the display is carried out with gain adjusted so as not to visualize noise, with the result that the influences due to the spread pulse waveform scarcely appear on an displayed image. In the end, the blood vessel diameter in the depth direction in the image remains within a deterioration range of an original resolution, which is formed by adding the pulse length $M/f_0$ to the original diameter itself of a blood vessel, and can be practically used.

However, when using the contrast agent, reflected signals from the contrast agent becomes a dominant in blood flow signals to be imaged, and their intensities increase by an amount of few dozens of decibels. As a result, most of the roots of a received pulse that has spread in the time-axis direction exceed the noise level, thus causing the blooming. This blooming generates in the azimuth direction as well.

As described above, there is a possibility that fine blood vessels can be seen through injecting the contrast agent. An important factor in observing blood flows passing through the fine blood vessels (significant blood flows are those of tumor and the coronaria) is to acquire realtime performance that assures the blood flow of being detected instantaneously at time when it began flowing, without fail. Since the conventional apparatus is obliged to observe blood flows of fine blood vessels in the CFM mode, a shortage of the number of frames becomes fatal. It is clear that a few frames in the CFM mode are still short for observation, and there is a fear that they fail to instantaneously detect a flowing blood.

Moreover, though injecting the contrast agent makes the detection sensitivity in the CFM mode improve up to a level as equivalent as the B mode, a conventional dynamic range for display in the power mode of the CFM mode is at most approx. 40 dB, which clearly shows there is a shortage in the range. Signals over 40 dB in sensitivity are all visualized with saturation at 40 dB, which results in poor gradation, thus providing only a blood flow image that gives a flat feeling in gradation. There is also a fear of degrading diagnosis capability on account of such poor gradation. Further, when diagnosing through observing the luminance levels of a blood flow image, the saturated portions cannot provide precise information about luminance levels.

In this way, where a blood flow is observed with the conventional apparatus with an objects into which the contrast agent is injected, there are various problems or drawbacks described above, thereby leading to a lowered performance in diagnosis, providing no practical use.

The foregoing conditions can be summarized as below, in which listed are representatives of unfavorable situations or unsolved problems about imaging blood flows using the conventional diagnostic ultrasound apparatus.

(1) In imaging blood flows of fine vessels on the conventional color Doppler technique, taking low-level blood flow signals into account, a variety of countermeasures to improve detection sensitivity are adopted, which include lengthening a transmission pulse length and various spatial average processing. But these countermeasures have been taken at the sacrifice of spatial resolution. Recently the basic performances of the apparatus have been advanced, and, like the improved power mode, there has been provided a mode to raise sensitivity without the sacrifice of the spatial resolution any more. The improved power mode is superior in sensitivity than the velocity mode of the CFM. Nevertheless, the power mode still succeeds a drawback that the resolution is low, like the conventional CFM mode. Primarily, without the heart's cavities, blood flow images are desired to be used in observing the existence and/or running conditions of blood vessels, like seen in diagnosing tumor. Thus it is required to depict blood vessels including as finer vessels as possible.

Although such a demand has existed, a measure against the problem has not been proposed yet. Under such a demand, for example, U.S. Pat. Nos. 4,809,249 and 4,928,698 disclose a way of mapping an object in motion on the basis of a cross correlation method (correlation in the time domain) using blood flow velocities. However, an amount that can be detected using the cross correlation method is a blood flow velocity having poor sensitivity. Meanwhile, an apparatus capable of performing a blood flow mapping technique called color velocity imaging (CVI) has also been developed. This apparatus, however, not only uses an ultrasound pulse whose wave-continuous length is short, which is called short pulse, but also uses the cross correlation method, with color mapping of blood flow velocities inferior in sensitivity performed.

Because these techniques focus on obtaining velocities of objects in motion such as blood flow, there is a difficulty in sensitivity for detecting blood that flows at slower speeds or fine blood flows. Therefore, a recent demand for ultrasound diagnosis that the existence itself of such blood flow is desired to be observed and confirmed at a higher accuracy has not been met yet.

On one hand, in the case that blood flows of fine vessels are tried to be observed with the conventional diagnostic ultrasound apparatus with the contrast agent injected into an object, which has been eagerly developed recently, there are the following problems.

(2) Although enhancement effects of a contrast agent can greatly raise detection sensitivity, the spatial resolution of blood flow images is deadly deteriorated, making diagnosis difficult.

(3) When an object to be observed is flow of fine blood vessels, there is a possibility that an observer fails to see significant behaviors of blood flows on account of the shortage of realtime performance. In such a case, diagnostic capability decreases extremely, lowering reliability in diagnosis.

(4) When enhancement effects of a contrast agent increases a detection sensitivity of blood flow up to a level as high as the B mode, the dynamic range for display in the power mode belonging to the CFM mode might become short. In such a case, display gradation in a blood flow image is saturated, lowering reliability in display. Additionally there is a fear that information on luminance lacks, lessening diagnostic capability.

SUMMARY OF THE INVENTION

The present invention has been attempted to break through the foregoing situations the conventional techniques encounter. One object of the present invention is to provide a blood flow image which spatial resolution is raised, especially, which depicts fine blood vessels or blood streams flowing at slower speeds, with great fineness.

Another object of the present invention is to provide a blood flow image possessing improved spatial resolution and higher S/N, even when blood of fine vessels is observed.

Still another object of present invention is to provide, in imaging blood of fine vessels utilizing enhancement effects of echo signals from a contrast agent administered into an object, an blood flow image having improved image quality for the power mode as well as improved spatial resolution and superior realtime performance.

In order to realize the foregoing objects, a diagnostic ultrasound apparatus according to the present invention is based on, as one aspect, a configuration that comprises: scanning means for not only scanning a cross section of an object to be imaged by transmitting at least two times, along the same direction in the cross section, an ultrasound pulse having a wideband frequency characteristic, but also acquiring an electric echo signal caused by the ultrasound pulse every time of transmission; processing means for performing processing with a train of data of the echo signal aligning in a time axis direction at each sample position in the cross section and being acquired by the scanning means, the processing being for extracting a signal of a moving element; producing means for producing the signal processed by the processing means into two-dimensional image data; and visualizing means for visualizing an image based on the two-dimensional image data.

The processing means consist of means that perform desired processing for extracting a change in a moving element or in a phase with the train of data.

Preferably, the desired processing performed by the processing means highpass filtering or differential processing.

Still preferably, the two-dimensional image data are data indicative of luminance information or power information of the echo signal reflected by the moving element existing in the cross section, or data indicative of luminance information or power information of the echo signal originated from a contrast agent residing in the cross section.

On one hand, a method of ultrasound diagnosis according to the present invention is characterized in that comprising the steps of: for not only scanning a cross section of an object to be imaged by transmitting at least two times, along the same direction in the cross section, an ultrasound pulse having a wideband frequency characteristic, but also acquiring an electric echo signal caused by the ultrasound pulse every time of transmission; performing processing with a train of data the echo signal aligning in a time axis direction at each sample position in the cross section and being acquired through the scanning, the processing being highpass filtering or differential processing; producing the signal processed into two-dimensional image data; and visualizing an image based on the two-dimensional image data.

One example of operation of the present invention derived from the above-mentioned configurations will now be described.

An imaging mode on the present invention is to be referred to as a "high resolution flow mode." This "high resolution flow mode" allows high resolution color flow mapping images or grayscale flow mapping images, which represent existence or non-existence of blood flow, to be displayed by a contrast echo method or a non-contrast echo method.

Specifically, as an ultrasound pulse having a wideband frequency characteristic, i.e., an ultrasound pulse of which spatial resolution is high is transmitted and received along an object's cross section in the same direction, a plurality of times, the cross section is scanned, producing a beamformed echo signal. From a train of data along the time axis at each sample position in the scanned cross section, which are formed from the echo signal, unnecessary clutter compotes (reflected signal components stationary or almost stationary tissues) are removed, an echo component of blood flow (echo component from a contrast agent) being, extracted. This echo component is produced into data of appropriate forms (practically, data consisting of luminance or power), and displayed as a blood flow image.

Such a blood flow image is provided as an image indicative of luminance or power of a wideband echo signal. Hence, compared to a conventional CFM blood flow velocity image that represents blood flow velocities where a transmission pulse length is long, fine blood flows or flows of which speeds are slow are steadily detested as well, so that provided is a blood flow image which is higher in resolution and sensitivity and which finely represents existence of blood flow. Hence information about existence of blood flow can be provided with great reliability based on improved detectability of blood flow.

On one hand, an ultrasound pulse is set to a wideband pulse, with the result that the band of a received signal varies depth by depth because of the effect of signal's frequency dependency within a living body. Accordingly, in response to the depth, the frequency of a reference signal for phase detection is controlled. Additionally, a filter whose band characteristic is variable, which is inserted into a receiving processor, is controlled in its band characteristic in response to the depth. Thanks to these configurations, both high resolution and high sensitivity are realized.

Moreover, injecting a contrast agent increases remarkably sensitivity. Thus, even if the number of transmission/reception times along the same direction in an object's cross section is reduced than scanning with no contrast agent, there can still be provided image of enough sensitivity and quality. Especially, when a signal-processing filter for extracting a blood flow signal is formed by a differentiator, clutter removal is possible by a minimum of two times of transmission/reception. In addition, in the case that a technique of simultaneous reception in a plurality of directions toward transmission in one direction is adopted, enough sensitivity and quality of images are obtained, however the number of receiving directions may be increased. In consequence, using both the techniques of the reduced number of transmission/reception times and/or increasing the number of simultaneous receiving directions is able to provide blood flow images of very high frame rates (time resolution).

Further, because of highly increased sensitivity resulting from a contrast agent, a display dynamic range for the power of echo signals needs to be widened largely. Determining the display dynamic rage in agreement with this power can provide the high-quality blood flow images, without image saturation (i.e., lack of blood flow information).

A reflected echo from a contrast agent includes high-level harmonics as well as a fundamental wave. The present invention, regardless of frequencies of these reflected waves, can be applied to any of the fundamental wave, harmonics, and a mixed wave of those.

To remove unnecessary clutter components, a high-pass filtering technique, which is high in removal capability, or differential technique, of which realtime performance can be set highly, may be available.

Echo components from blood flow (echo components from a contrast agent) are possible to be formed into image data in an appropriate form. For example, they may be power image data produced using power mode processing or may be luminance image data produced using B-mode processing.

Due to the fact that a contrast agent collapses within a range of sound pressures used in an ordinary diagnosis or vibrates irregularly, the phase of reflected echo signals vary irregularly. Thus, however blood flow (contrast agent) may be nearly at rest in tissue, like blood perfusion, echo signals from the contrast agent, of which phases have varied, are extracted by highpass filtering or differential processing, differently from tissue echoes (clutters). Therefore, applying the present invention to an object into which a contrast agent makes it possible to detect through the fundamental wave the perfusion which was impossible to detect in the past, providing high-resolution, high-sensitivity, an realtime perfusion images.

The other constructions, operations and advantages according to the present invention will become distinct from the following embodiments and description on the accompanying drawings.

PREFERRED EMBODIMENTS OF THE INVENTION

Various embodiments of the present invention will now be described with reference to the accompanying drawings.

(1) First Embodiment

Referring to FIGS. 1 to 4 and 39, a diagnostic ultrasound apparatus according to a first embodiment will now be described.

This diagnostic ultrasound apparatus is used to obtain a blood flow image by performing an contrast echo technique that requires a contrast agent to be injected to, for example, the vein of a patient, but it is not necessarily required that the contrast agent be injected. That is, the apparatus is also used in performing a non-contrast echo technique.

Figure 1:
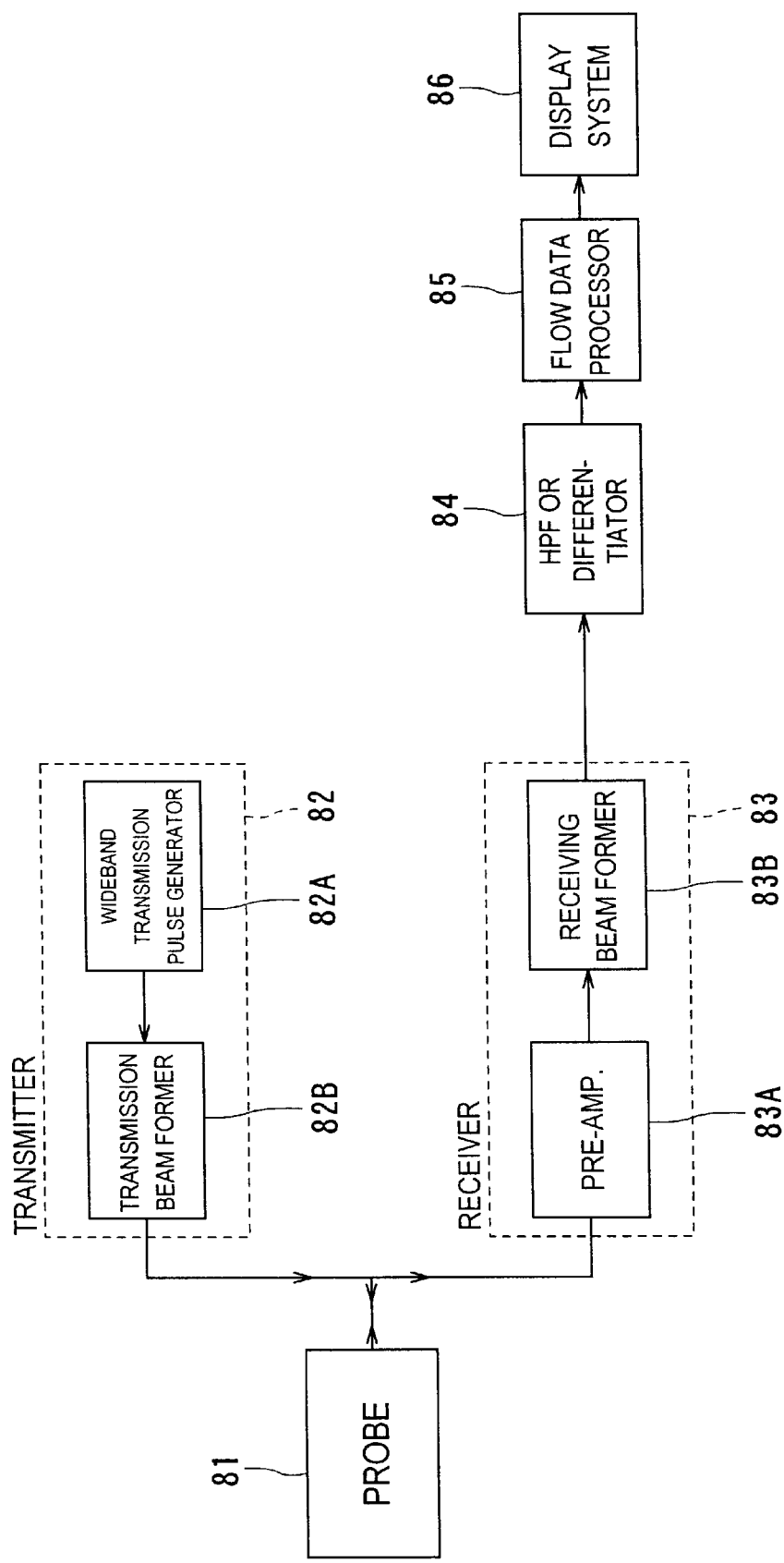
FIG. 1 shows in block form an outlined configuration of a diagnostic ultrasound apparatus according to a first embodiment of the present invention.

FIG. 1 is a block diagram that shows an outlined configuration of this diagnostic ultrasound apparatus. In this apparatus, a transmitter 82 and a receiver 83 are both connected with a probe 81. A highpass filter (HPF) or differentiator 84, flow data processor 85 and display system 86 are arranged in this order at the output side of the receiver 83. Either one of the HPF or the differentiator 84 is used to remove a signal component originated from surrounding tissue to extract a reflected signal from blood flow.

The transmitter 82 is provided with a wideband transmission pulse generator 82A that produces wideband ultrasound pulses and a transmission beam former 82B that delays the ultrasound pulses and applies them to the probe 81. Also, the receiver 83 is provided with a pre-amplifier 83A that amplifies the detected echo signals by the probe 81 and a receiving beam former 83B that delays and mutually adds the output signals of this amplifier. The wideband transmission pulse generator 82A and the transmission beam former 82B individually include circuit elements corresponding to the number of transmission channels. Also, the pre-amplifier 83A and the receiving beam former 83B individually include circuit elements corresponding to the number of reception channels.

The wideband transmission pulse generator 82A produces a pulse that is not only wide in band than the pulse used in the conventional CFM-mode imaging but also as wide as (wideband) an ultrasound pulse used to produce ordinary conventional B-mode tomograms. This produced pulse is sent to the transmission beam former 82B. Thus, the transmission beam former 82B drives the probe 81 based on a transmitting delay technique using the wideband pulse, resulting in that a "wideband" ultrasound pulse is radiated from probe 81. The ultrasound pulse thus-radiated is beam-formed within a patient body so as to become a beamed pulse.

Widening the band of an ultrasound pulse will now be explained. Considering the reciprocal of a transmission frequency $f_0$ is a transmission cycle $T_0$, an ultrasound pulse having a time length corresponding to 1 cycle "$T_0$" of an ultrasound wave is referred to as a pulse of one burst wave, an ultrasound pulse having a time length of 2 cycles "$2T_0$" to a pulse of two burst waves, and an ultrasound pulse having a time length of M cycles "$MT_0$" to a pulse of M burst waves, respectively, in which one wave, two waves, . . . , M-piece waves are called the burst wave number. The value that multiplies the transmission cycle by the burst wave number is equal to the pulse length.

The wideband transmission pulse generator 82A is a constituent composing one of the characteristics of this invention, and specifically produces a pulse of which transmission frequency is $f_0$ and of which wideband burst wave number is M-pieces which are less than 3. Although an example of the burst wave whose burst wave number is "one wave" is explained below, this still holds the generality of this invention.

Figure 2:
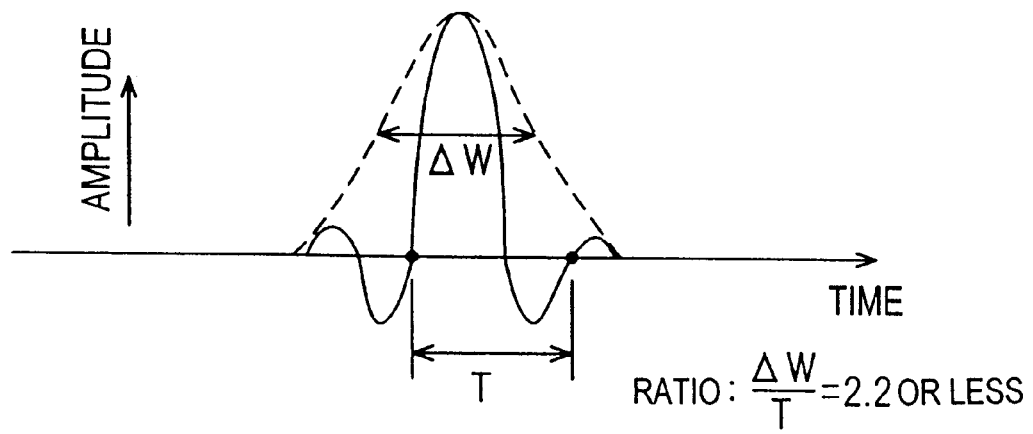
FIG. 2 illustrates a burst waveform of a wideband transmission ultrasound pulse.

This "wideband transmission/reception pulse" is not necessarily limited by defining the number of burst waves (less than 3 waves). Alternatively, the wideband may be defined with the ratio "$\Delta W/T$" between a half width value $\Delta W$ of the envelope of a time burst wave and a cycle T thereof, as shown in FIG. 2. When this ratio is used, the transmission/reception pulse employed in this invention is expressed by $$\Delta W/T = \text{less than } 2.2.$$

Figure 3:
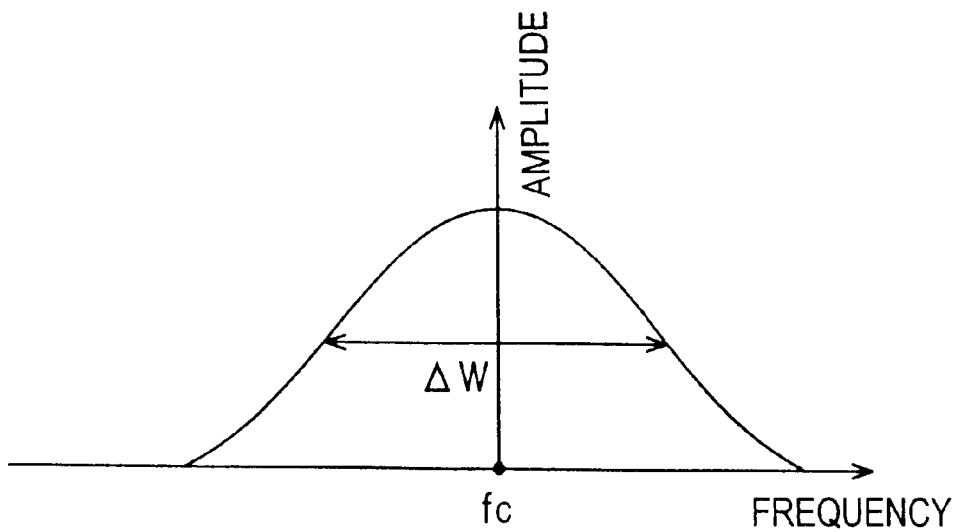
FIG. 3 illustrates a fractional bandwidth of a wideband transmission ultrasound pulse.

Alternatively, as shown in FIG. 3, a fractional bandwidth= $\Delta W/fc$ of the spectrum of a transmission/reception pulse ($\Delta W$: half width value, fc: spectral center frequency) may be used to define the range of the wide band. In this case, a range defined by $$\text{fractional bandwidth} = \Delta W/fc = 0.3 \text{ or more}$$

corresponds to the "wideband" referred to the present invention.

Referring to FIG. 1, reflected signals of a transmission ultrasound pulse received by the probe 81 are inputted into the receiving beam former 83B through the pre-amplifier 83A of the receiver 83 as the echo signals of electric quantity, every reception channel. Delay and addition for beam forming is performed with the echo signals in this beam former 83B, similarly at the time of the transmission.

An echo signal thus-beam formed enters either one of HPF or differentiator 84. The differential processing is not limited to a simple difference computed between adjacent two data residing in an echo signal train. This differential processing may be any kind of difference, provided that signal components derived from surrounding tissue are removed.

In this embodiment, the ultrasound pulse is transmitted and received along the same raster direction, at least twice. Thus, the echo signal that has inputted in one of HPF or differentiator 84 generates a train of echo data that line up in the time axis direction, every sample position in a scanned section of a patient body.

The HPF or differentiator 84 performs highpass filtering or space-based differential processing with each of the trains of echo signals, extracting echo components caused by blood flow. Such filtering or difference permits components originated from tissue to be removed.

Figure 4:
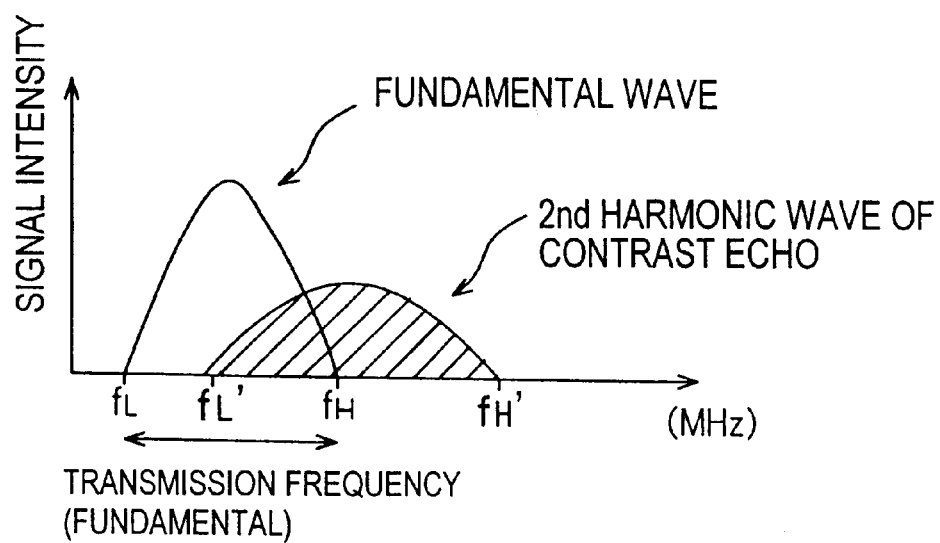
FIG. 4 exemplifies waveforms indicative of frequency regions for harmonic imaging.

FIG. 4 shows the spectrum of a signal received from a contrast agent. Echo signals which have reflected by microbubbles composing an essential component of the contrast agent include harmonics, subharmonics, and ultraharmonics because of their non-linear oscillation characteristics. Therefore, the band of a received signal is determined to include a band of non-linear signals as well as the band of a transmitted signal.

In performing the contrast echo technique, echo components originated from a contrast agent enters the flow data processor 85. In this processor 85, the echo component signals are processed into image data showing luminance or power information of the echoes from the contrast agent. In contrast, if the non-contrast echo technique is executed, the flow data processor 85 processes echo component signals into image data showing luminance or power information of the echoes from blood flow. The image data are displayed by the display system 86, as a blood flow image that shows the existence positions of blood flow.

In consequence, B-mode or power-mode (color-mode) blood flow images can be displayed. By way of example, a high-resolution flow image is displayed as pictorially shown in FIG. 39(*b*) (wherein an image in FIG. 39(*a*) exemplifies a conventional Doppler velocity image, written for comparison with the former.)

In this visualization of a blood flow image, since the wideband ultrasound pulse is transmitted, grayscale flow images of higher spatial resolution or higher-resolution color images are obtained. The unnecessary tissue echoes are removed, because the highpass filtering or differential processing is carried out every the sample point in the space of a scanned section, resulting in that echo signals originating from an injected contrast agent (corresponding to blood flow) or echo signals reflected directly from blood flow are steadily extracted.

Moreover, this diagnostic ultrasound apparatus does not employ a technique of computing blood flow velocities on the Doppler technique so as to obtain blood flow images, like seen in the conventional CFM (color flow mapping) method. Instead, performing highpass filtering or differential processing with echo signals that have been received through a plurality of times of scanning along each raster direction leads to a steady extraction of echo signals from blood flow, thereby removing tissue echo signals. Furthermore, the extracted blood flow echo signals are processed into luminance or power information, without the computation of velocity distributions as in the conventional CFM mode, and the luminance or power information is displayed as a blood flow image. Compared to the case that a blood flow velocity distribution is computed depending on the Doppler method (refer to FIG. 39(*a*)), blood that flows at slow speeds and/or flows through fine vessels is detected with high sensitivity. Therefore, the depicting ability in relation to the presence of a blood flow B in a displayed blood flow image (refer to FIG. 39(*b*)) is more excellent than that on the blood flow velocity distribution.

The advantage of improvement for this depicting ability can be obtained even in the non-contrast echo imaging that does not require the injection of a contrast agent. Because complete non-invasiveness is also realized, this embodiment is extremely effective when a thin blood vessel is visualized.

Additionally, the highpass filtering and differential processing permits blood flow echo signals to be depicted in a steady fashion, so that a B-mode image is also able to accomplish blood flow imaging with features of the image used.

(2) Second Embodiment

Figure 5:
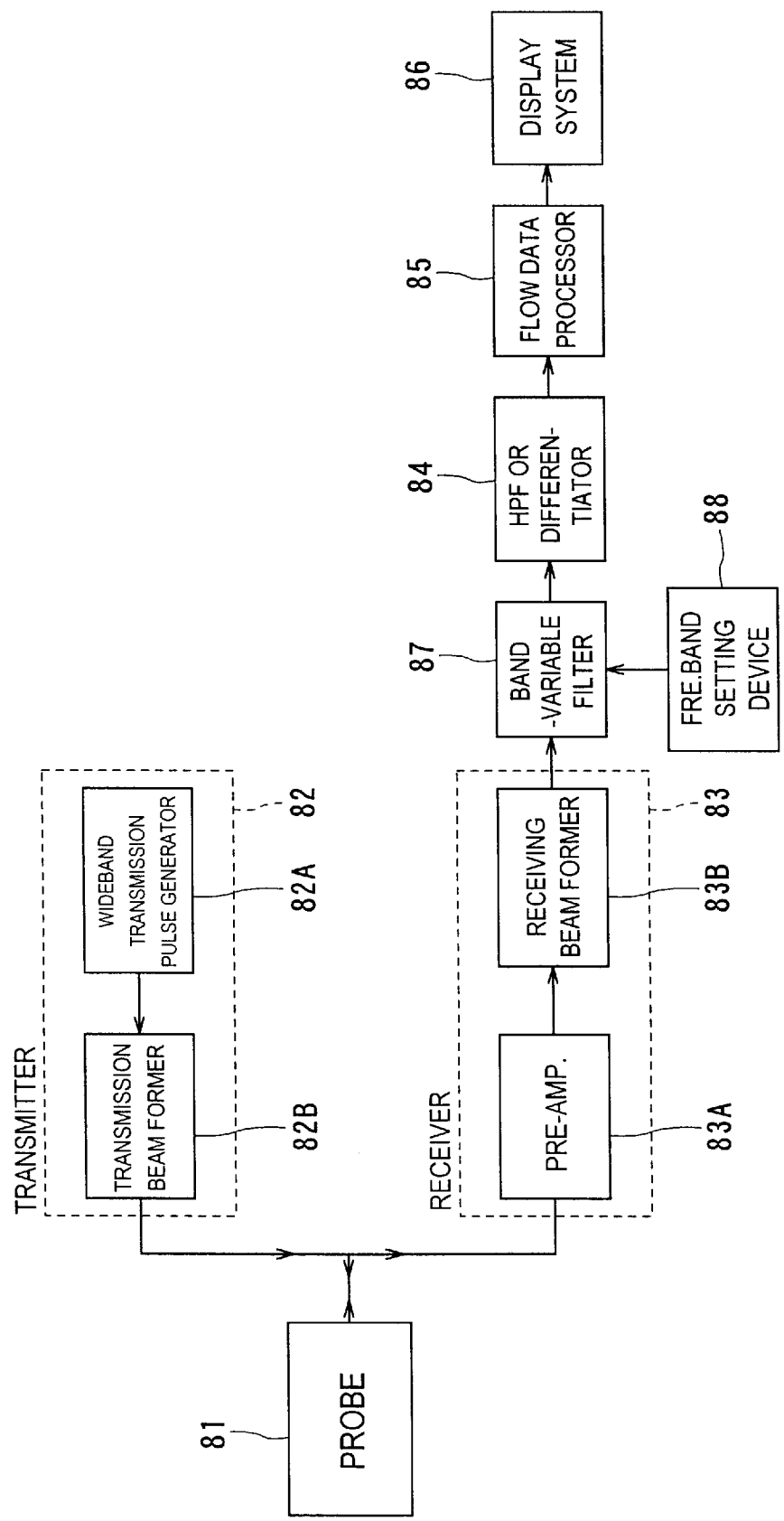
FIG. 5 outlines in block form the configuration of a diagnostic ultrasound apparatus according to a second embodiment of the present invention.

Referring to FIG. 5, a diagnostic ultrasound apparatus according to a second embodiment will now be described. This apparatus is used on the contrast echo or non-contrast echo method and uses a band-variable filter.

As shown in FIG. 5, between the receiving beam former 83B and the HPF or differentiator 84, a band-variables filer 87 functioning as filter means is inserted. The band-variable filter 87 has a passing band controlled by a frequency band setting device 88.

The band-variable filter 87 has a desired passing characteristic set to a passing echo signal at each depth in a raster along which a received beam is formed. This configuration is able to remove noise existing in an outside band of a signal so as to increase an S/N. In addition, echo signals are obtained, from which influences of both signal attenuation and band changes in the depth direction are corrected. Further it is possible that the fundamental wave of high sensitivity, a harmonic wave of less artifact, a mixed wave of those, or others is selected, permitting the selection of a reception signal frequency most suitable to occasions.

As the band-variable filter 87, a filter which band-filters an RF signal, a filter which band-filters an intermediate frequency signal, a filter which filters in a low band a signal produced by quadrature phase detection, or the like can be employed. In the case of employing the intermediate frequency method or quadrature phase detection method, a reference frequency and a filter bandwidth are changed in agreement with a depth in each raster direction.

The other configurations are identical to those in the first embodiment.

As a result, in addition to the operations and advantages obtained in the foregoing first embodiment, a blood flow image is obtained, in which improvement for an S/N is secured, influence on band changes or signal losses in the depth direction along each raster is corrected steadily, and both improvement for sensitivity and the reduction in influence of artifact are optimized.

(3) Third Embodiment

Figure 6:
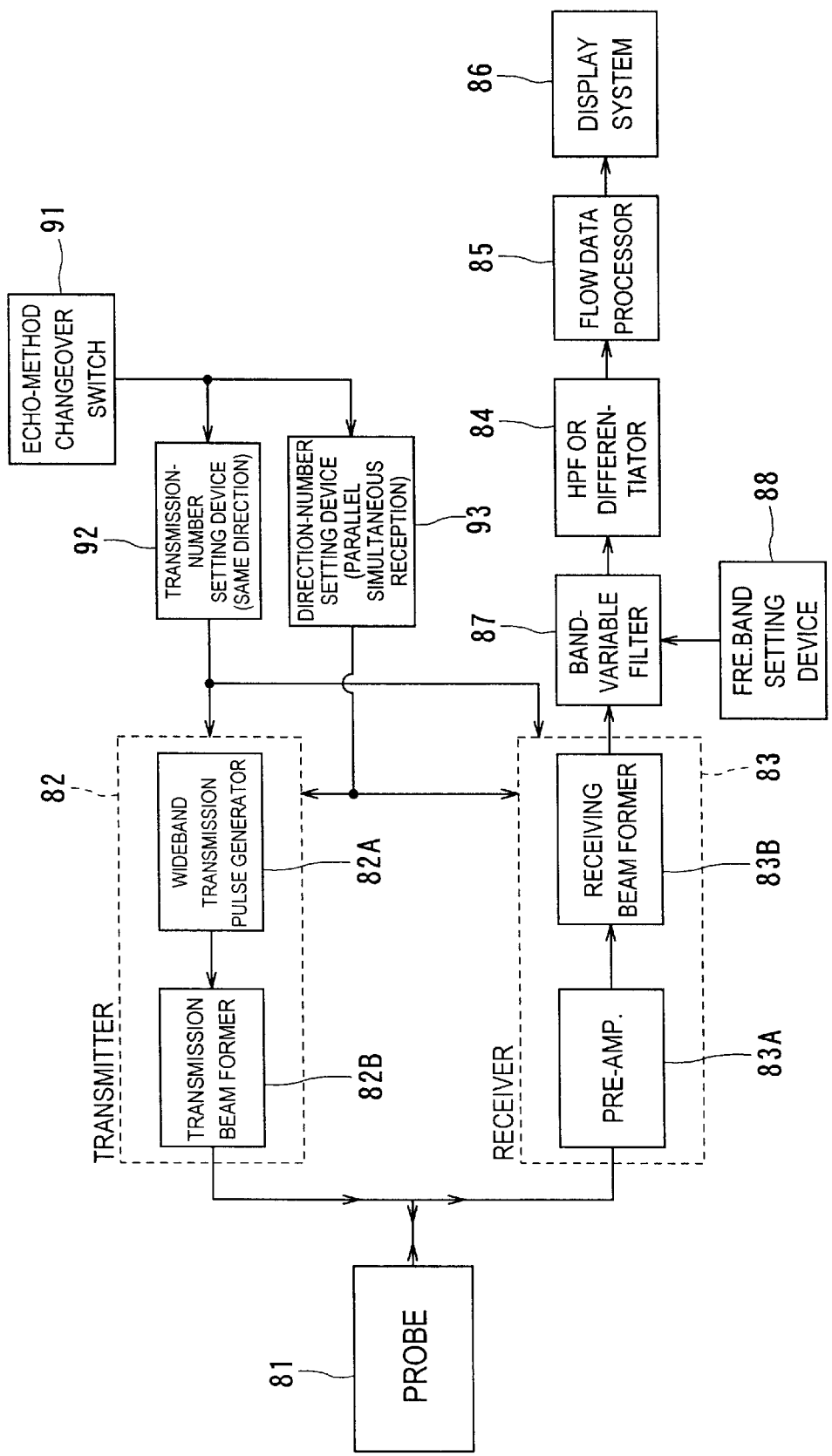
FIG. 6 outlines in block form the configuration of a diagnostic ultrasound apparatus according to a third embodiment of the present invention.

Referring to FIG. 6, a diagnostic ultrasound apparatus according to a third embodiment will now be described. This apparatus is concerned with the changeover of transmission/reception characteristics in cases where the contrast and non-contrast echo methods are selectively used.

As shown in FIG. 6, on top of the configurations in FIG. 5, there are additionally provided an echo-method changeover switch 91, transmission-number setting device 92, and direction-number setting device 93.

The echo-method changeover switch 91 is provided to, for example, manually command the changeover between the contrast and non-contrast echo methods. The switch signal is given both the direction-number setting device 93 and the transmission-number setting device 92.

The direction-number setting device 93 is placed to set the number of directions for parallel simultaneous reception and its setting signal is sent to both the transmitter 82 and the receiver 83. The transmission-number setting device 92 is provided to set the number of times of transmitting an ultrasound pulse in the same direction under transmission and its setting signal is handed over to both the transmitter 82 and the receiver 83.

In accordance with the switch information, that is, whether it is the contrast echo method or non-contrast echo method, the receiving direction-number setting device 93 automatically changes over and sets differently the number of directions for parallel simultaneous reception. Also, in accordance with the switch information, that is, whether it is the contrast echo method or non-contrast echo method, the transmission-number setting device 92 automatically changes over and sets differently the number of times of transmission in the same direction.

A practical changeover is such that, when the contrast echo method is commanded by the echo-method changeover switch 91, the parallel simultaneous reception number is increased, while the transmission number along the same raster direction is decreased, compared to the non-contrast echo method.

Also provided in the transmitter 82 are two pieces of information; information indicating the parallel simultaneous reception number different depending on the contrast echo method or the non-contrast echo method stated above, and information representing the number of times of transmission along the same transmitting direction given from the transmission-number setting device 92. This allows the transmitter 82 to repetitively transmit a wideband ultrasound pulse in the same raster direction by a specified number of times. On one hand, the receiver 83 executes simultaneous reception for a specified number of parallel simultaneous reception.

Therefore, the following eminent merits are obtained, in addition to the operations and advantages in the foregoing first and second embodiments.

First there is an advantage resulting from the parallel simultaneous reception. Since, in cases a contrast agent is injected into an object for scanning, as described before, the detection sensitivity is normally enhanced by a few dozens of decibels, the detection sensitivity is still enough even if a transmission beam is widened and the number of parallel simultaneous reception is increased. Thus, when the contrast echo method is instructed, the direction-number setting device 93 operates to increase the number of parallel simultaneous reception, compared to the non-contrast echo method. This raises remarkably the number of frames (i.e., temporal resolution), thus providing blood flow images of higher temporal resolution.

Further, there is provided an advantage yielding from controlling the number of times of transmission in the same transmitting direction. Because a blood flow echo single is low in intensity, this signal is subject to the influence of noise. To reduce this influence, in detecting blood flow echo signals, normally, an ultrasound pulse is transmitted and received in the same raster direction, for example, 16 times, so that a train of data consisting of a plurality of data aligning time-sequentially in relation to the same signal source (a sample position in a scanned section) are detected, and a blood flow echo signal is then extracted from the data train through highpass filtering or differential processing. In the case of the contrast echo method, however, the detection sensitivity from blood flow is enhanced by a few dozens of decibels, greatly improving an S/N, resulting in that a blood flow echo signal hardly has the influence of noise. Namely, even though the number of times of transmitting an ultrasound pulse in the same raster direction is lowered, a blood flow signal of which S/N is high is obtained in a stable signal state. When the contrast echo method is issued, the transmission-number setting device 92 reduces the number of times of transmission in the same raster direction. This reduction allows the number of frames per sec. (corresponding to temporal resolution) to increase, thus providing blood flow images of a high realtime performance.

Moreover, in this embodiment, the foregoing techniques of increasing the number of directions for parallel simultaneous reception and decreasing the number of times of transmission in the same raster direction are both used, extremely enhancing the effect of improvement for realtime performance. If necessary, either one of the foregoing two techniques may be used alone. Alternatively, both of the two techniques can be applied to the apparatus in the first embodiment.

(4) Fourth Embodiment

Figure 7:
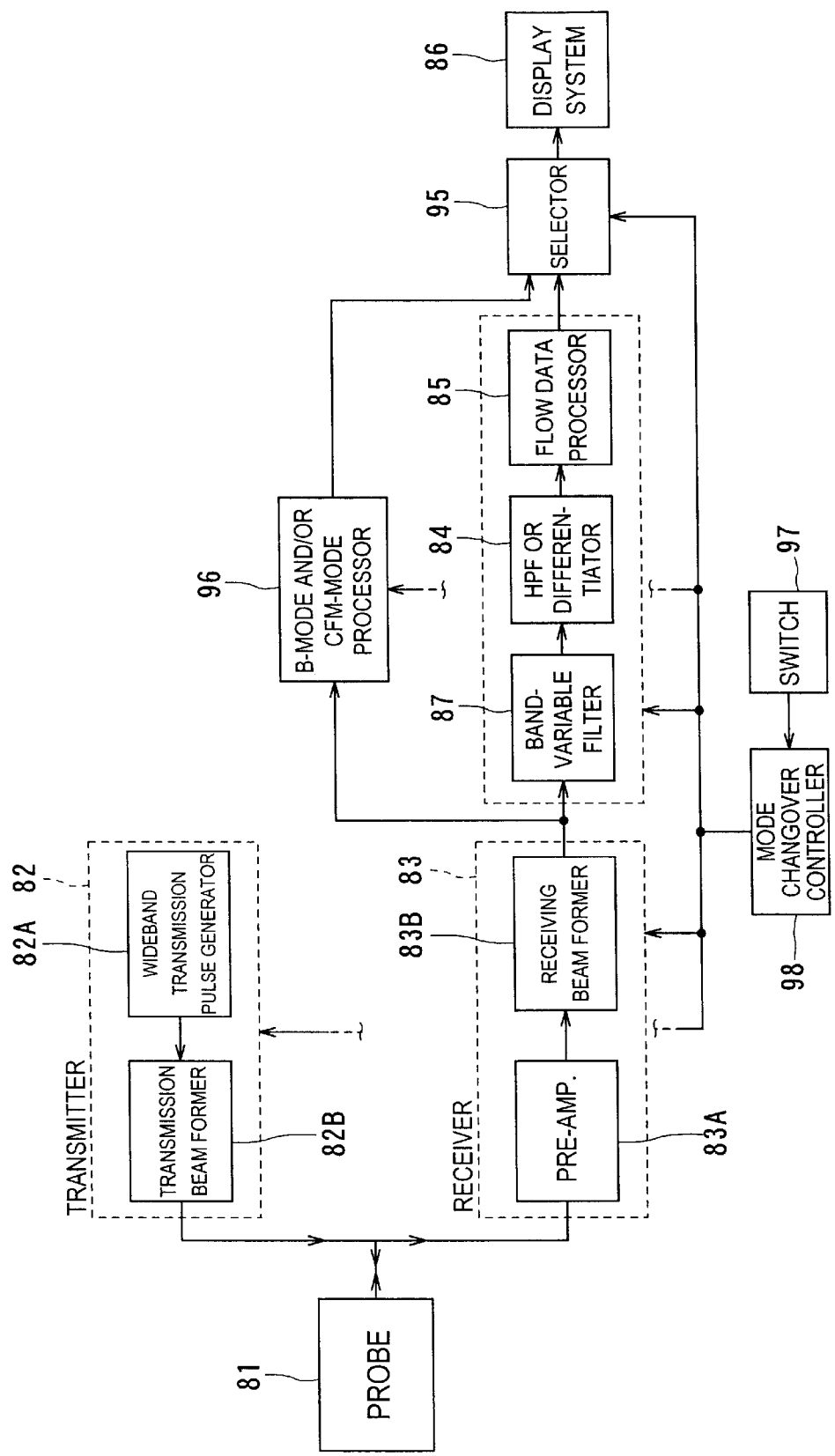
FIG. 7 outlines in block form the configuration of a diagnostic ultrasound apparatus according to a fourth embodiment of the present invention.

Referring to FIG. 7, a diagnostic ultrasound apparatus of a fourth embodiment will now be described. This apparatus relates to the changeover control between the high-resolution flow mode according to the present invention and an ordinary B or CFM mode that has been used so far.

As shown in FIG. 7, between the flow data processor 85 and the display system 86, a selector to select image data is inserted. Meanwhile, from the output of the receiver 83, a B-mode and/or CFM-mode processor 96 is placed in parallel to the band-variable filter 87, HPF or differentiator 84, and flow data processor 85. The selector 95 is able to, therefore, select either image data from the B-mode and/or CFM-mode processor 96 or image data from the flow data processor 85 residing in the high-resolution flow mode side, and send the selected image data to the display system 86.

A switch 97 constitutes means, for example, manually used by an operator to change over modes. A signal from the switch is supplied to a mode changeover controller 98. Responsively to the issued mode, this controller 98 issues a changeover command to a high-resolution flow processing unit comprising the transmitter 82, receiver 83, band-variable filter 87, HPF or differentiator 84, and flow data processor 85, the selector 95, and the B-mode and/or CFM-mode processor 96.

If the processor 96 is a B-mode processor, a not-shown control circuit operates to have a transmission/reception control function. By this function, transmitting and receiving an ultrasound pulse one time per each raster produces an echo signal sent to the processor 96.

Accordingly, an operator can freely change over a display mode of a blood flow image between the high-resolution flow mode and the conventional B mode and/or CFM mode. This enables the operator to observe the same blood flow from various aspects, providing the apparatus higher versatility as well as securing steady diagnosis.

(5) Fifth Embodiment

Figure 8:
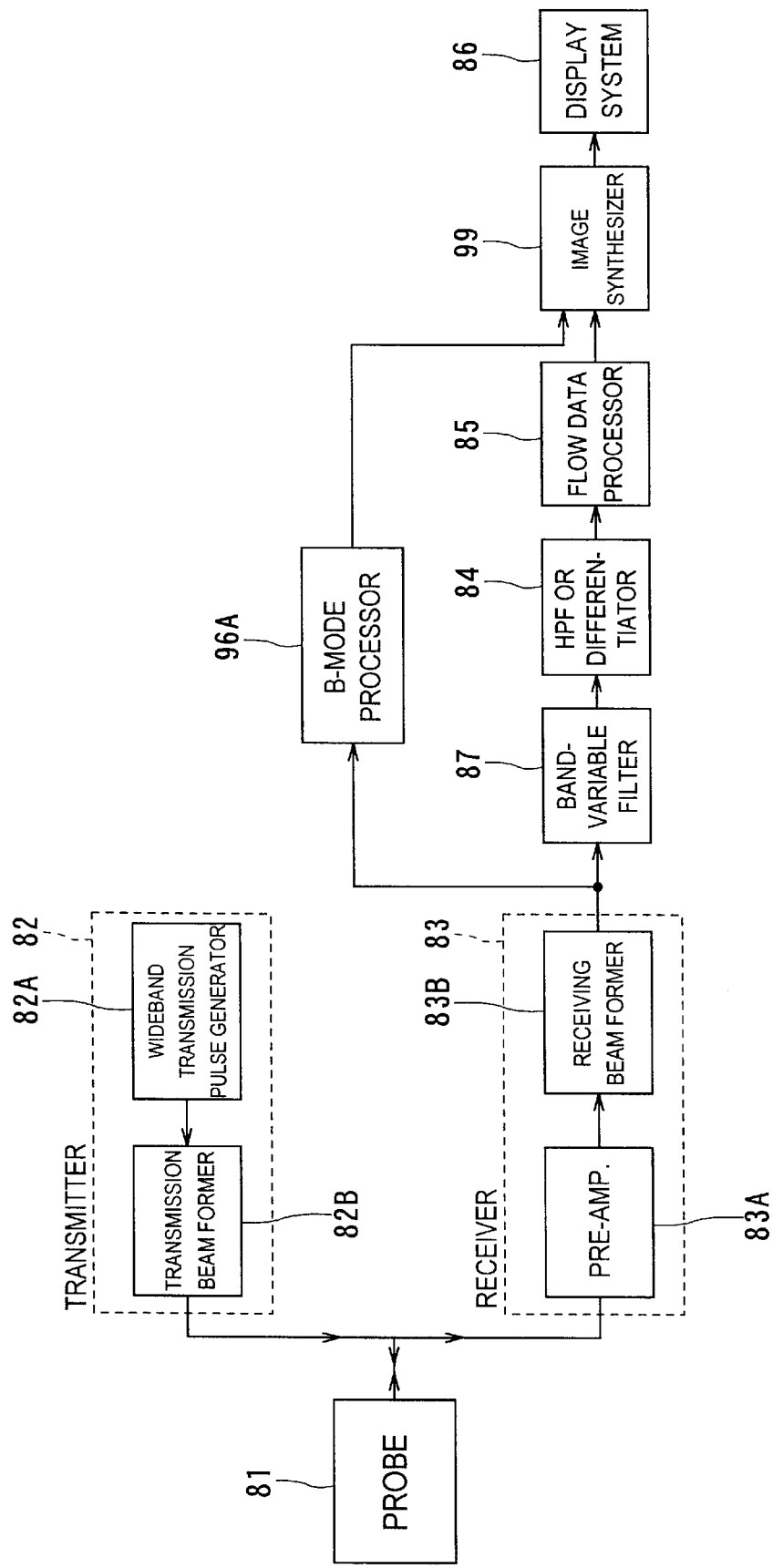
FIG. 8 outlines in block form the configuration of a diagnostic ultrasound apparatus according to a fifth embodiment of the present invention.
Figure 39:
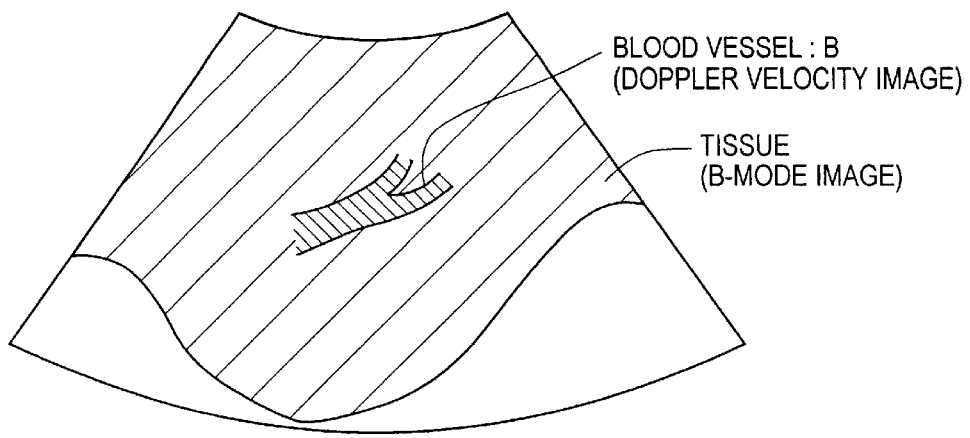
FIG. 39 exemplifies a blood flow image on a high-resolution flow mode in the first and fifth embodiments, which is accompanied by a conventional Doppler velocity image.
Figure 39:
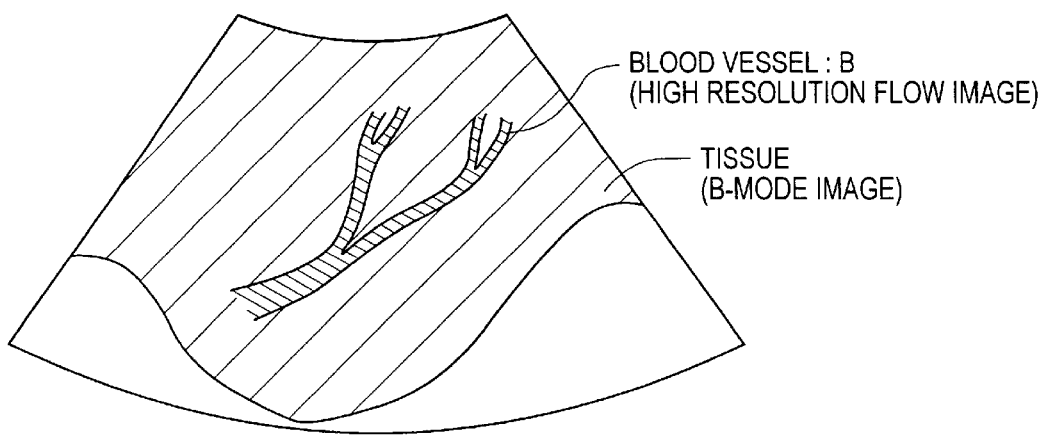
Figure 40:
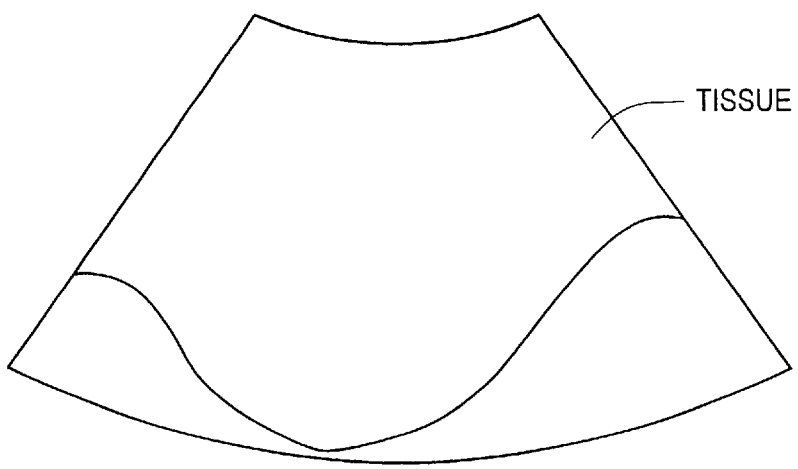
FIG. 40 shows an example of a perfusion image on a high-resolution flow mode based on the contrast echo technique in the eighth embodiment, which is accompanied by a conventional Doppler velocity image.
Figure 40:
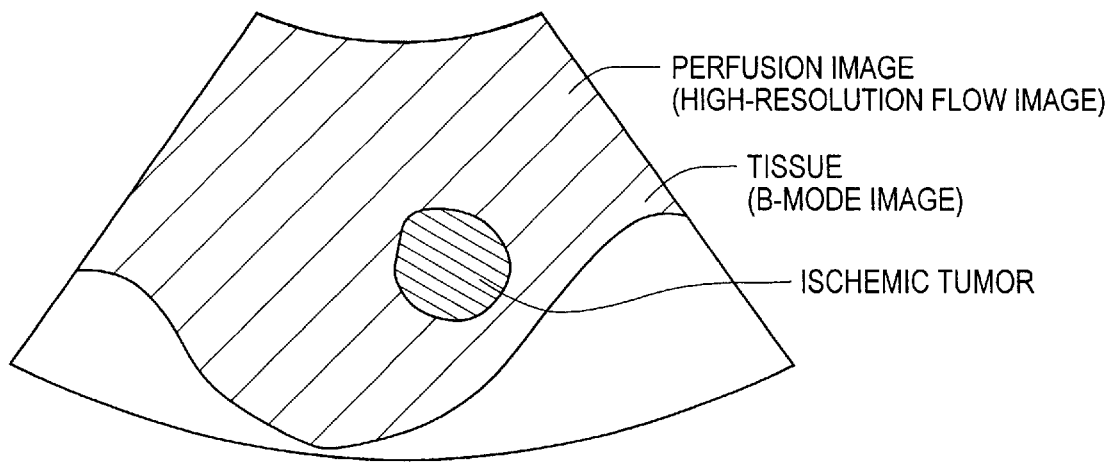
Figure 41:
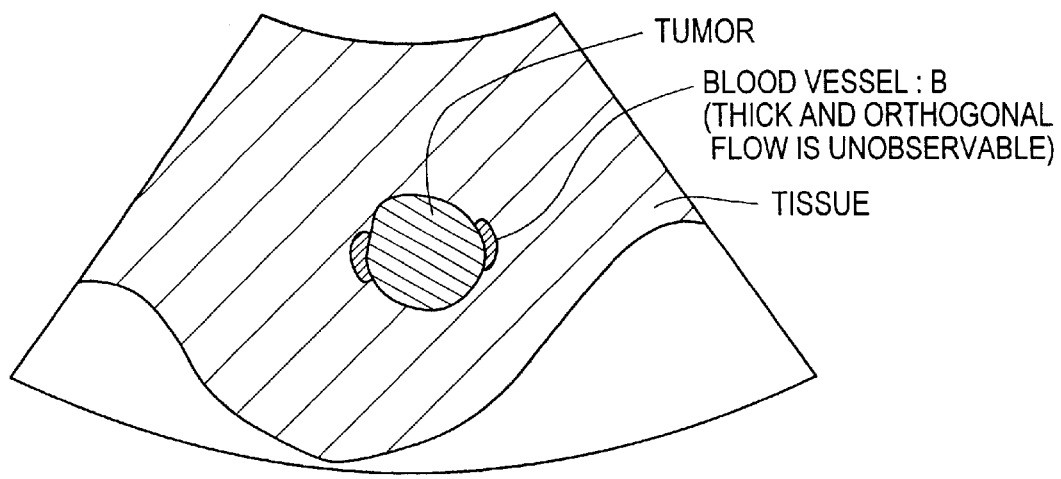
FIG. 41 shows an example of a blood flow image toward an orthogonal flow on the high-resolution flow mode in the eighth embodiment, which is accompanied by a conventional Doppler velocity image.
Figure 41:
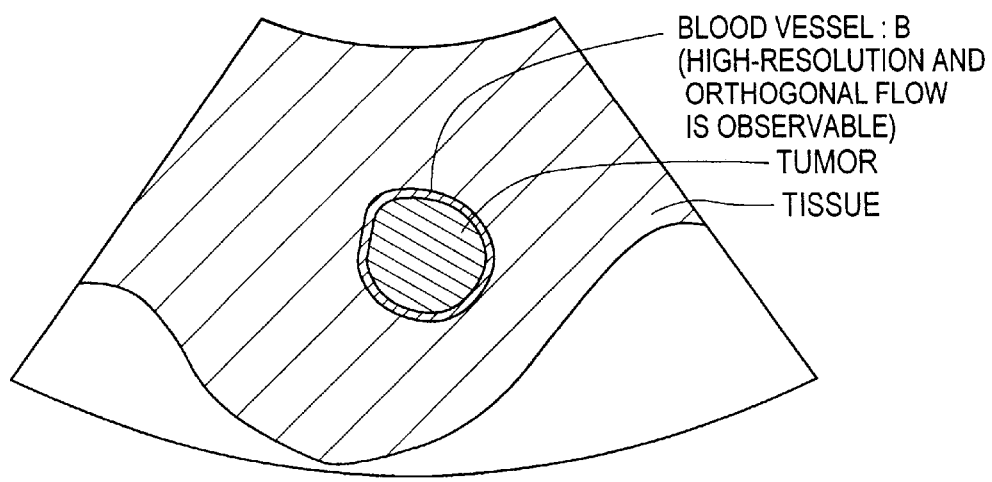

Referring to FIGS. 8 and 39, a diagnostic ultrasound apparatus of an eighth embodiment will now be described. This apparatus features a technique that the high-resolution flow mode of the present invention and the ordinary B mode conventionally used are synthesized for image display.

As shown in FIG. 8, a B-mode processor 96A is disposed in parallel with a high-resolution flow processing unit comprising the band-variable filter 87, HPF or differentiator 84, and flow data processor 85. The outputs of both the processor 85, which is at the final stage of the high-resolution flow processing unit, and the B-mode processor 96A are provided to the display system 86 via an image synthesizer 99 that synthesizes image data pixel by pixel.

A not-shown control circuit operates to have a transmission/reception control function that transmits and receives an ultrasound pulse one time per each raster, producing an echo signal sent to the B-mode processor 96A.

Accordingly, by means of the synthesizer 99, as pictorially shown in FIG. 39(*b*), a blood flow image under the high-resolution flow mode is superposed on a B-mode tomographic image when they are displayed. (FIG. 39(*a*) illustrates as a comparative example of a conventional Doppler velocity image.) If a blood flow is low in velocity or thin in diameter, it is detected at high sensitivity. Thus, the B-mode tomographic image becomes a background image, providing a high-resolution blood flow image in which the position of the blood flow is easy to recognize.

(6) Sixth Embodiment

Figure 9:
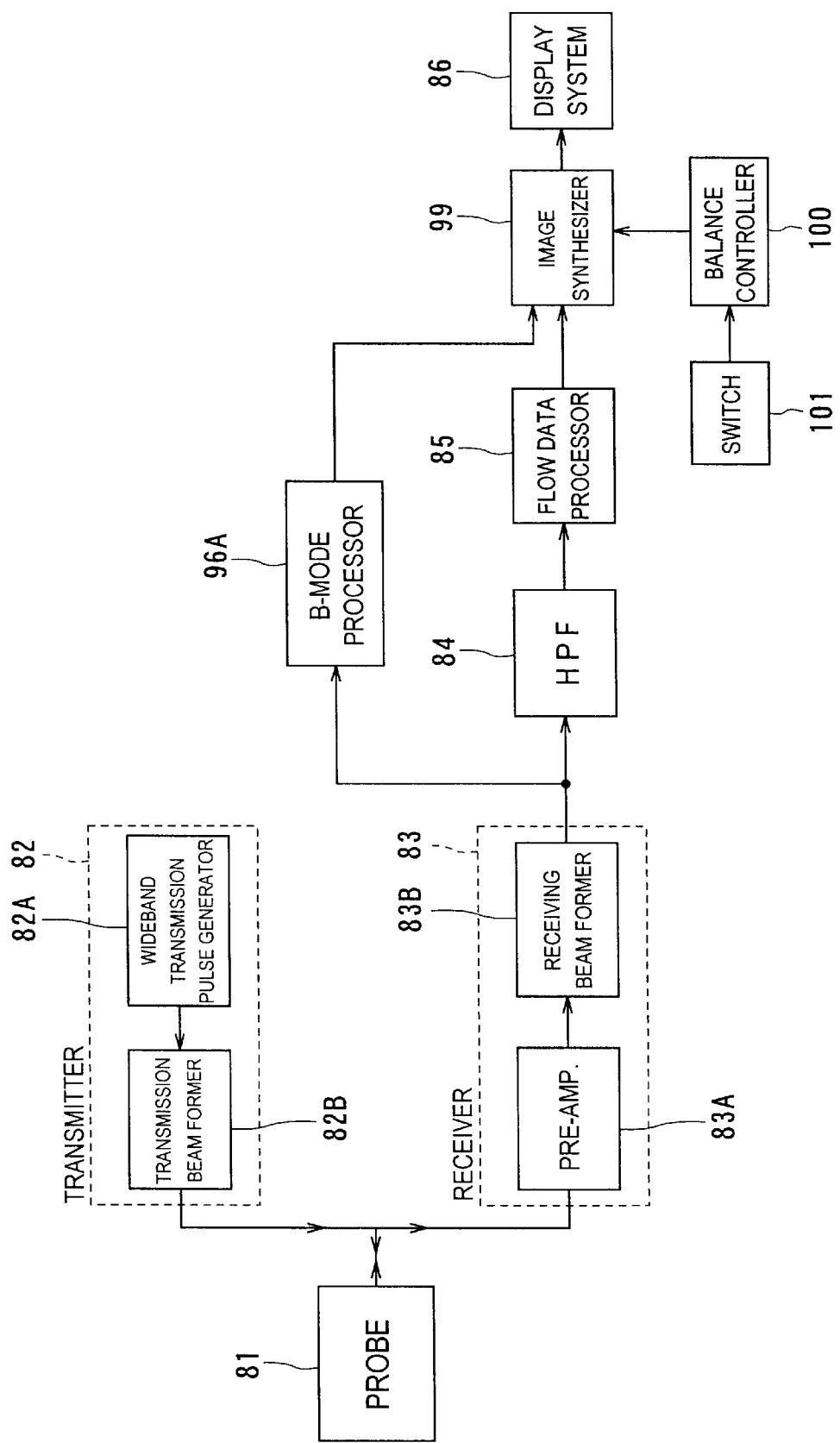
FIG. 9 outlines in block form the configuration of a diagnostic ultrasound apparatus according to a sixth embodiment of the present invention.

Referring to FIG. 9, a diagnostic ultrasound apparatus of a sixth embodiment will now be described. This apparatus has a function of obtaining a blood flow referred to as a "high-resolution color image," based on the "high-resolution flow mode" of the present invention. This apparatus can be practiced by any of the contrast echo method or the non-contrast echo method.

In this apparatus, as shown in FIG. 9, at the output side of the receiver 83, disposed in parallel are circuits realizing the high-resolution flow mode and consisting of the HPF 84 and flow data processor 85, and the B-mode processor 96A. Both of the circuit systems are further connected to the display system 86 via the synthesizer 99. With the synthesizer 99, a balance controller 100 and a switch 101 are coupled to control a display balance (synthesized balance) between a blood flow image and a contour image.

Of these, the flow data processor 85 not only performs power calculation at a level which is the same as or similar to that of the power calculation performed in the CFM mode but also codes the calculated power values into color data with luminance corresponding thereto.

The synthesizer 99 synthesizes the outputs of the flow data processor 85, which becomes the outputs from the high-resolution color mode processing unit, with the outputs of the B-mode processor 96A, thus producing one set of image data.

The balance controller 100 receives a signal of the switch 101, which is produced by manual operation, for instance. Responsively to this signal, the controller 100 is capable of adjusting how both B-mode image data and blood flow image data are synthesized.

Therefore, under the high-resolution flow mode, an echo signal sent from the receiver 83 undergoes highpass filtering in the HPF 84, being extracted as an echo signal inherent in blood flow or a contrast agent. The flow data processor 85 inputs the echo signal to calculate the power thereof and produce color image data of a luminance level that corresponds to the power value. The color image data are sent to the synthesizer 99.

By contrast, an echo signal sent from the receiver 83 under the B mode is produced by the B-mode processor 96A into grayscale B-mode image data composed of luminance levels in accord with signal intensities. The B-mode image data thus produced are also supplied to the synthesizer 99.

The synthesizer 99 synthesizes image data pixel by pixel such that a blood flow image is superposed on a B-mode image. Specifically, concerning pixels at which only either the B-mode image data or blood flow image data exist, data at the existing pixels are employed. In contrast, as to pixels at which data of both the images commonly exist, two synthesizing techniques can be used selectively. One synthesizing technique is adopting image data of the blood flow image in preference to the other. Using this synthesizing method, a blood flow image is represented on the tomographic image without fail. The other synthesizing method is synthesizing the blood flow image on the B-mode image as mixing ratios of pixel values of those images are adjusted. This way of synthesis enables the blood flow image to be displayed without fail, with the tomographic image observed transparently.

It is preferable that both the synthesizing techniques be continuously changed over therebetween, for example. Namely, a condition at which a mixing ratio of 100% is given the blood flow image in this mixing synthesis corresponds to the former synthesizing technique under which the priority is given the blood flow image. According to a state set through the switch 101, the balance controller 100 adjusts this mixing ratio.

The data of a synthesized image are supplied to the display system 86, so that they are displayed. As a result, with the B-mode image used as a background, the blood flow image superposed on the B-mode image is displayed in almost real time. That is, the blood flow image is displayed in the state that it is overlaid on the B-mode image that provides contour information.

Therefore, as seeing an image displayed on the display system 86, an operator can operate the switch 101 in an appropriate manner. This permits a synthesizing balance between the B-mode image and the blood flow image to be changed relatively. Thus, for example, a region of interest can easily be confirmed with the visualized image.

Alternatively, the foregoing diagnostic ultrasound apparatus may has a function of obtaining a blood flow image referred to as a "grayscale flow" based on the "high-resolution flow mode" of the present invention. In such case, instead of the foregoing configuration, it is enough that the flow data processor 85 has a construction for calculating luminance at an identical or nearly identical level to that in the B mode. Thus in the state that the contrast echo method or non-contrast method is carried out, a normal B-mode image is used as a background, and a blood flow image on luminance information in "high-resolution flow mode" is superposed on the background and displayed. Operating the switch 101 also enables the adjustment of the mixing ratio at the synthesizer 99, controlling relatively a synthesizing balance between the background image composed of the B-mode image and the blood flow image consisting of luminance information.

(7) Seventh Embodiment

Figure 10:
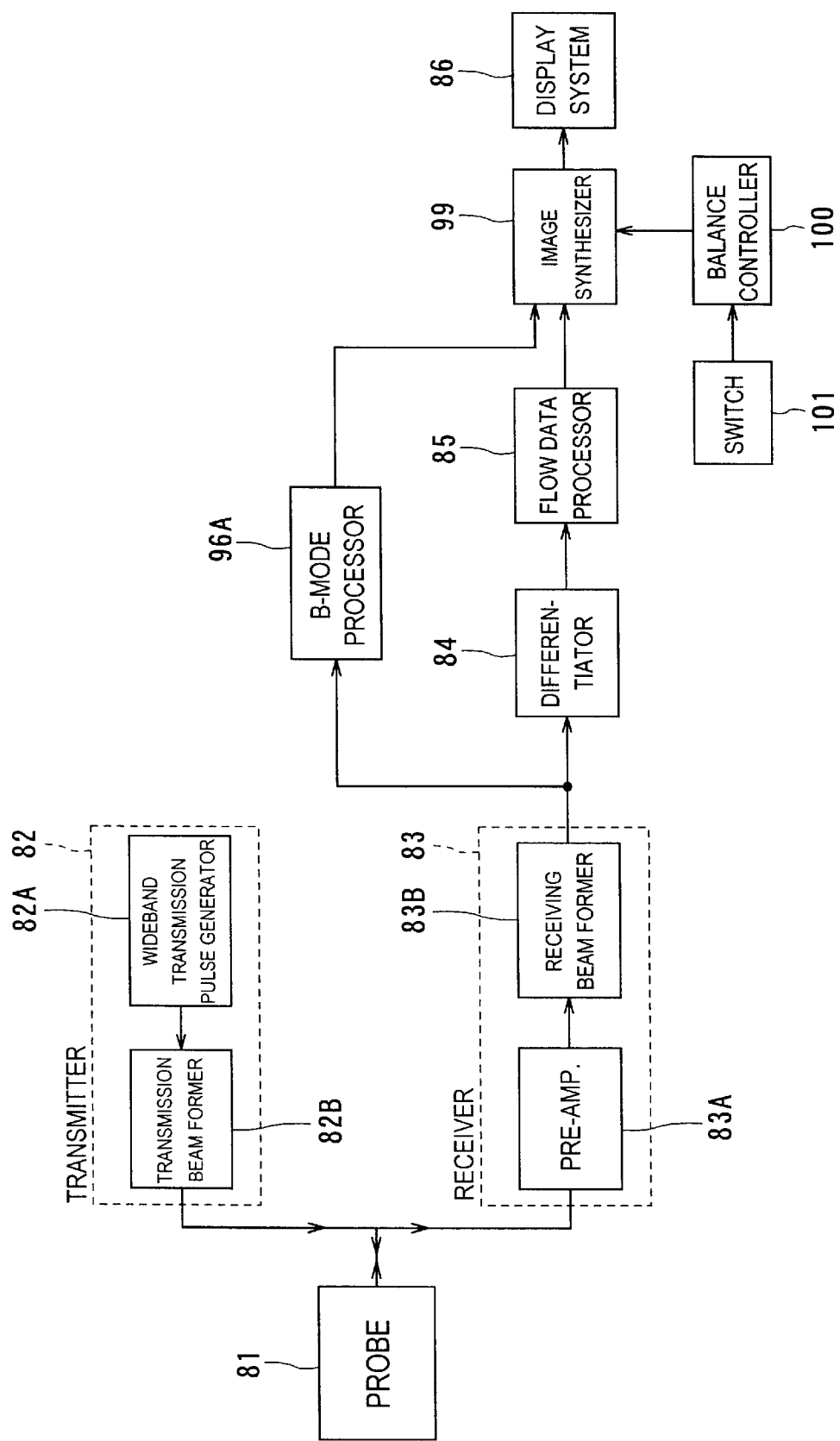
FIG. 10 outlines in block form the configuration of a diagnostic ultrasound apparatus according to a seventh embodiment of the present invention.

Referring to FIG. 10, a diagnostic apparatus of a seventh embodiment will now be described. Like the sixth embodiment, the diagnostic ultrasound apparatus has a function of acquiring a blood flow image called "high-resolution color" image based on the "high-resolution flow mode" of the present invention. This apparatus can be practiced using either the contrast or non-contrast echo method.

In this apparatus, as shown in FIG. 10, at the output stage of the receiver 83, there are provided in parallel a circuit group for the high-resolution flow mode, which comprises the differentiator 84 and the flow data processor 85, and the B-mode processor 96A. The remaining circuitry is identical to that in FIG. 9.

Therefore, as described before, under the high-resolution flow mode, an echo signal supplied from the receiver 83 is differentially calculated by the differentiator 84, being extracted as an echo signal originating from blood flow or a contrast agent. The flow data processor 85 inputs the echo signal to calculate the power thereof and forms color image data each of which luminance corresponds to the calculated power amount. The color image data are sent to the synthesizer 99.

On one hand, under the B mode, the echo signal from the receiver 83 is produced by the B-mode processor 96A into grayscale B-mode image data each of which luminance is in accord with an intensity of the echo signal. The B-mode image data are also sent to the synthesizer 99.

The synthesizer 99 synthesizes image data pixel by pixel such that a blood flow image is superposed on a B-mode image. Specifically, concerning pixels at which only either the B-mode image data or blood flow image data exist, data at the existing pixels are employed. In contrast, as to pixels at which data of both the images commonly exist, two synthesizing techniques can be used selectively. One synthesizing technique is adopting image data of the blood flow image in preference to the other. Using this synthesizing method, a blood flow image is represented on the tomographic image without fail. The other synthesizing method is synthesizing the blood flow image on the B-mode image as mixing ratios of pixel values of those images are adjusted. This way of synthesis enables the blood flow image to be displayed without fail, with the tomographic image observed transparently.

It is preferable that both the synthesizing techniques be continuously changed over therebetween, for example. Namely, a condition in which a mixing ratio of 100% is given the blood flow image in this mixing synthesis corresponds to the former synthesizing technique under which the priority is given the blood flow image. According to a state set through the switch 101, the balance controller 100 adjusts this mixing ratio.

The data of a synthesized image are supplied to the display system 86, so that they are displayed. As a result, with the B-mode image used as a background, the blood flow image superposed on the B-mode image is displayed in almost real time.

Therefore, an operator can operate the switch 101 in an appropriate manner, which allows the synthesizing balance between the B-mode image and the blood flow image to be changed relatively.

Alternatively, the foregoing diagnostic ultrasound apparatus may have a function of obtaining a blood flow image referred to as a "grayscale flow" based on the "high-resolution flow mode" of the present invention. In such case, instead of the foregoing configuration, it is enough that the flow data processor 85 has a construction for calculating luminance at an identical or nearly identical level to that in the B mode.

Moreover, in the foregoing fourth to seventh embodiments, for displaying on the display system 86 different types of images (for example, a B-mode or CFM-mode image and a blood flow image based on the "high-resolution flow mode" of the present invention), it is not always to superpose them one on another. By way of example, those images may be displayed on the same screen in a separated form. Alternatively, a plurality of display systems may be prepared, where each image is presented on each display system.

(8) Eighth Embodiment

With referent to FIGS. 11–15, 40 and 41, a diagnostic ultrasound apparatus of an eighth embodiment will now be described.

Figure 11:
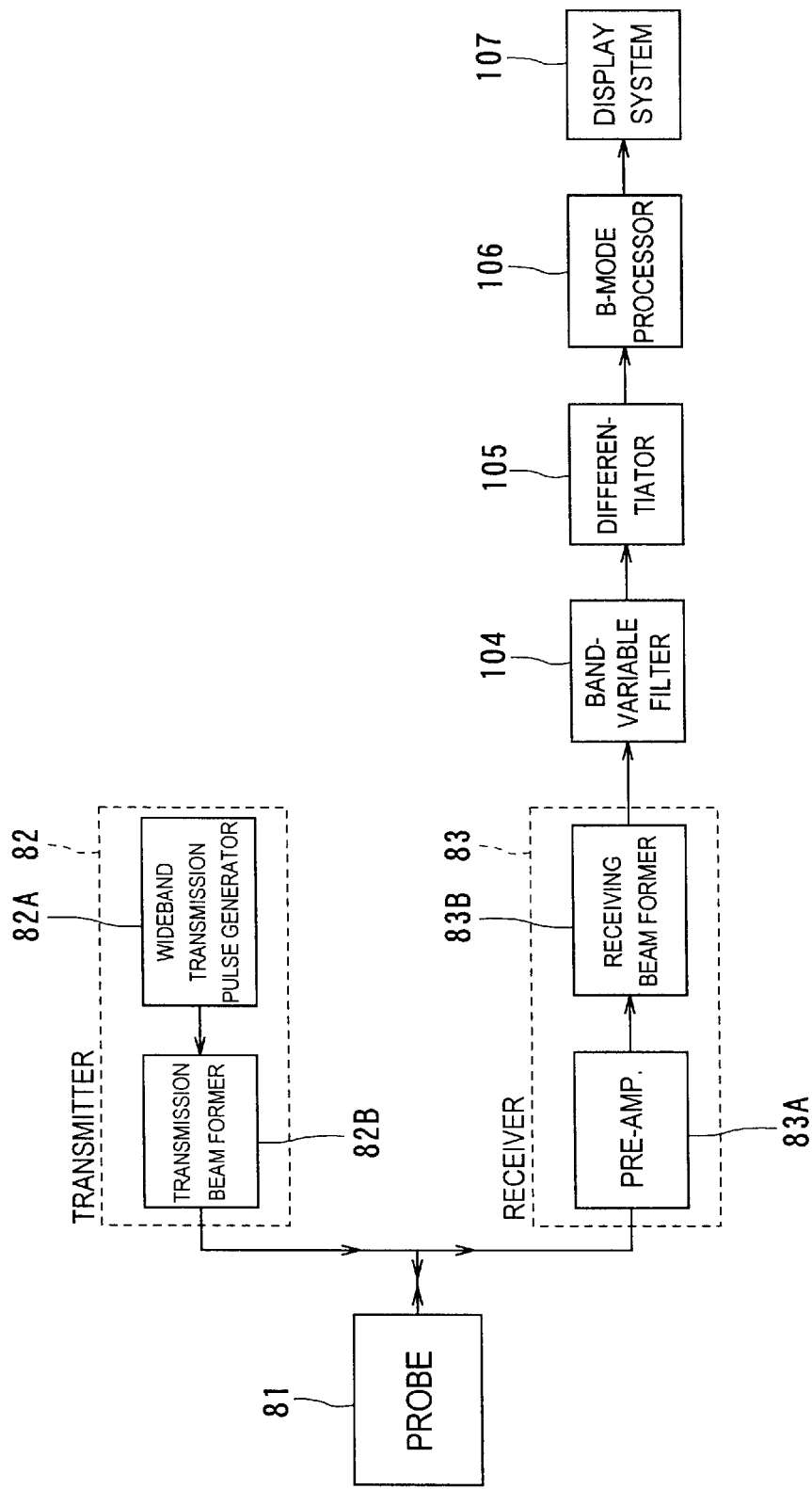
FIG. 11 outlines in block form the configuration of a diagnostic ultrasound apparatus according to an eighth embodiment of the present invention.

This apparatus shows an example in which the present invention is applied to diagnosis performed in a B mode or harmonic B mode with a contrast agent injected FIG. 11 is a block diagram showing an outlined configuration of the diagnostic ultrasound system. In the apparatus, a transmitter 82 and a receiver 83 are coupled in parallel with a probe 81. And the output side of the receiver 83, a band-variable filter 104, differentiator 105, B-mode processor 106, and display system 107 are disposed in this order.

The transmitter 82 has a wideband transmission pulse generator 82A generating a wideband ultrasound pulse and a transmission beam former 82B delaying the ultrasound pulse to apply it to the probe 81. The receiver 83 has a pre-amplifier 83A amplifying echo signals detected by the probe and a receiving beam former 83B delaying and adding output signals of the amplifier. Of these, each of the wideband transmission pulse generator 82A and the transmission beam former 82B includes individual circuit elements corresponding to the number of transmission channels, while each of the preamplifier 83A and the receiving beam former 83B includes individual circuit elements in accord with the number of reception channels.

Figure 12:
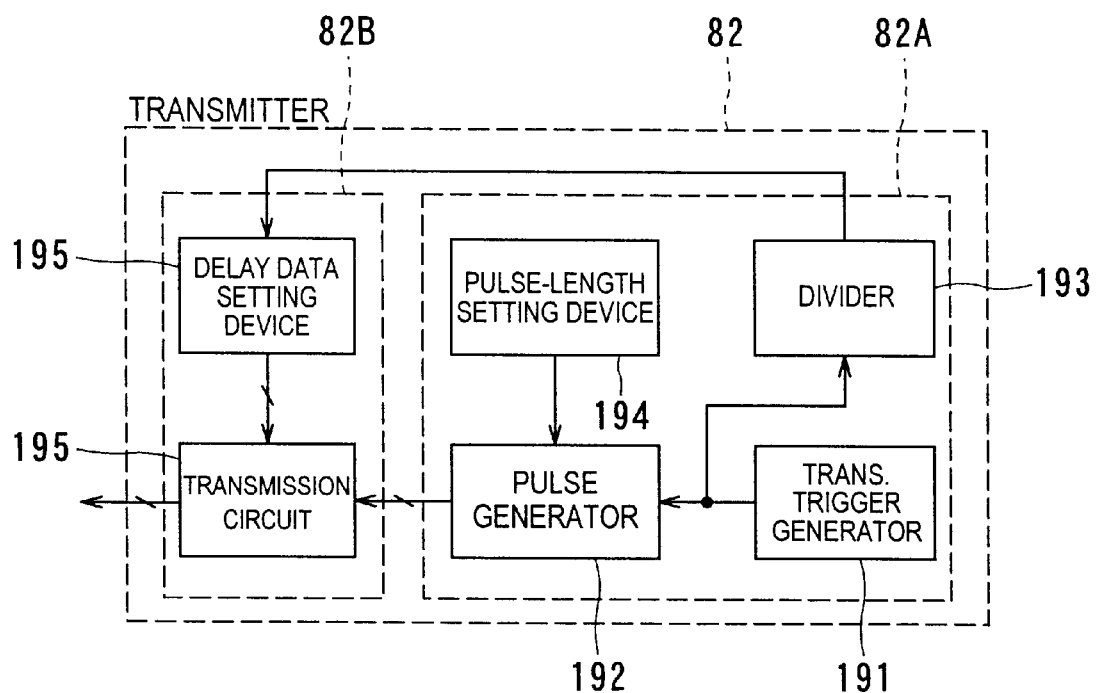
FIG. 12 is a block diagram of a transmitter installed in the apparatus of the eight embodiment.

The transmitter 82 is configured, in detail, into circuitry shown in FIG. 12. That is, the wideband transmission pulse generator 82A comprises a transmission trigger generator 191, pulse generator 192, divider 193, and pulse-length setting device 194. The transmission beam former 82B comprises a transmission circuit 195 and a delay data setting device 196.

Figure 13:
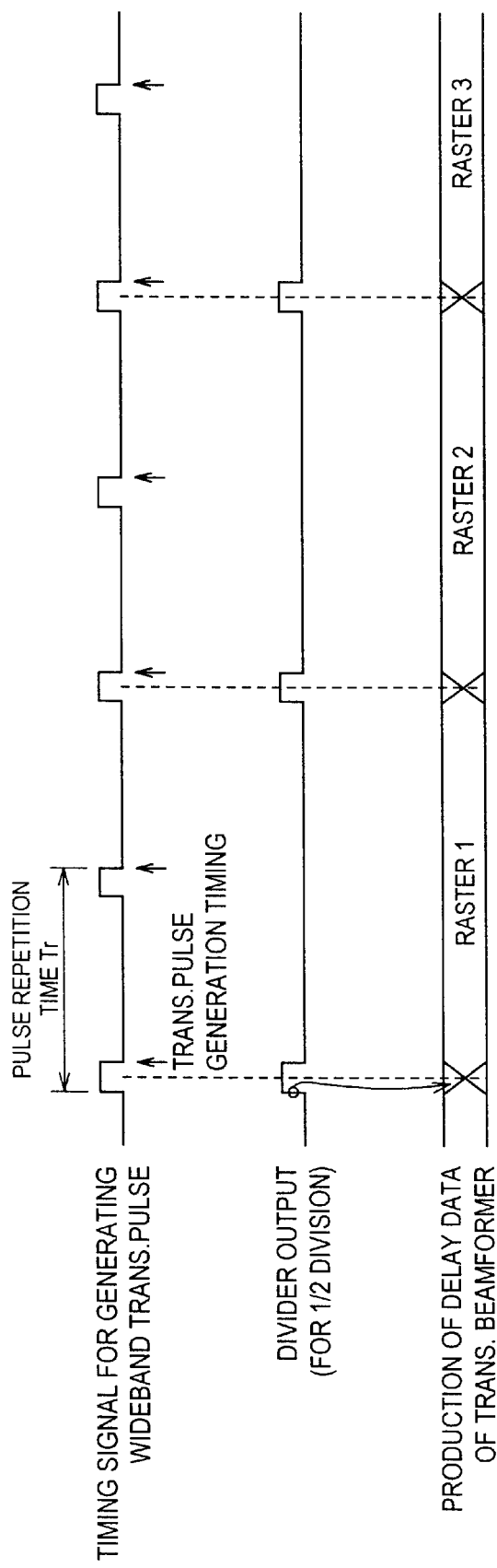
FIG. 13 is a timing chart explaining the operation of the transmitter used in the eight embodiment.

The transmission trigger generator 191 outputs, as shown in FIG. 13, a timing signal for generating a transmission pulse at a predetermined pulse repetition time Tr. This timing signal is provided to the pulse generator 192 and the divider 193. The pulse-length setting device 194 sends a pulse-length setting signal for transmitting a wideband ultrasound pulse to the pulse generator 192.

The pulse generator 192 generates driving pulses corresponding to the number of transmission channels in response to the timing signal and the pulse-length setting signal and give them to the transmission circuit 195. The divider 193 divides the timing signal into a signal activated at every given period (refer to FIG. 13, in which 1/2 division is shown) and send the divided signal to the delay data setting device 196.

Furthermore, the delay data setting device 196 generates, every input of the divided signal (i.e., every raster), data of delay amounts for respective transmission channels to control the direction of a raster (scanning line), like electric sector scanning, for example, and provides them to delay elements in the respective transmission channels of the transmission circuits 195 (refer to FIG. 13). Thus, the transmission circuit 195 delays the driving signals for each transmission channel, amplifies them, and gives them to a plurality of transducers of the probe 81. Accordingly, an ultrasound pulse transmitted from the probe 81 into an object body has a transmission directivity in conformity with the data of delay amounts.

Figure 14:
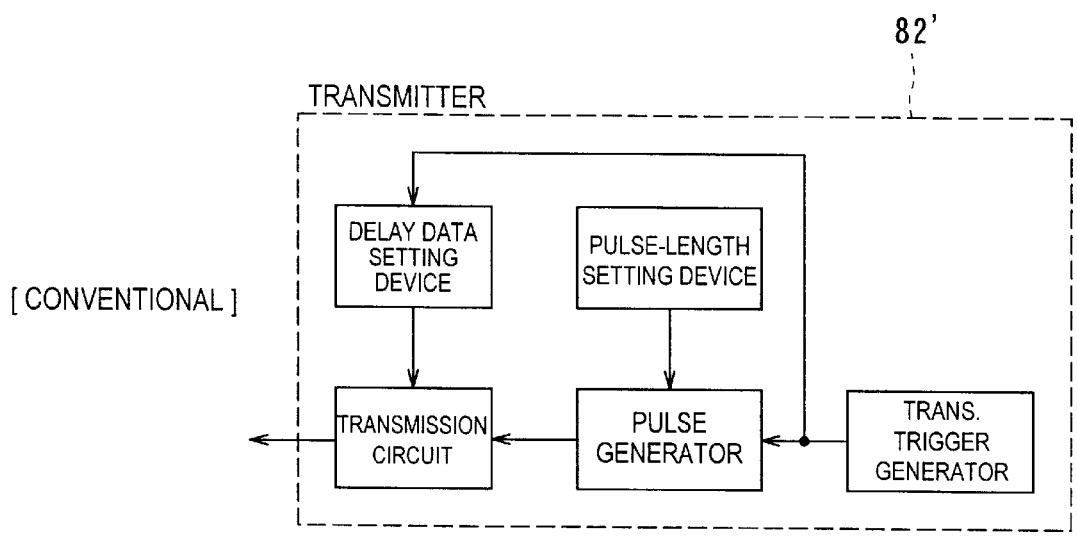
FIG. 14 shows a block diagram of a conventionally used transmitter, described for comparison.
Figure 15:
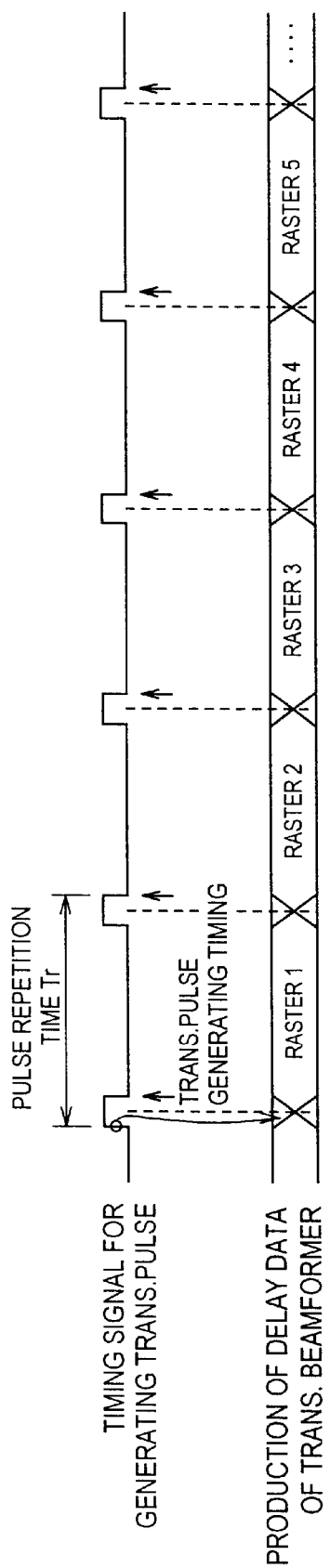
FIG. 15 shows a timing chart of the conventionally used transmitter, described for comparison.

For comparative explanation, FIG. 14 shows a conventional transmitter 82', which should be compared to the circuitry of FIG. 12. That is, this transmitter is formed, without a divider, to have a pulse-length setting device for setting a desired pulse length of which band is not wide, differently from the present invention providing a wideband pulse. For comparison, FIG. 15 shows the operation of the circuitry of FIG. 14.

On one hand, a reflected signal of the transmitted ultrasound pulse which is received by the probe 81, as an electric echo signal in each reception channel, is provided to the receiving beam former 83B via the pre-amplifier 83A of the receiver 83. In this beam former 83B, like the transmission, the echo signals are delayed and added to each other, realizing beam forming.

The echo signal thus-beamformed is sent to the band-variable filter 104 to which desired characteristics or filtering bands. are set at each depth, in which a desired frequency component is thus extracted for each depth. As the band-variable filter 104, a filter which band-filters an RF signal, a filter which band-filters an intermediate frequency signal, a filter which filters in a low band a signal produced by quadrature phase detection, or the like can be employed. In the case of employing the intermediate frequency method or quadrature phase detection method, a reference frequency and a filter bandwidth is changed in agreement with a depth in each raster direction. In the case of displaying images in the harmonic B mode, the band of a reception signal is set to include the band of a non-linear signal as well as the band of a transmission signal.

In this embodiment, the ultrasound pulse is transmitted and received along the same raster direction, at least twice. Thus, by the differential filter 105, differential processing on space-based is performed with received echo signals scanned a plurality of times in the same raster direction, so that a signal originated from the contrast agent is detected. This signal is sent through the B-mode processor 106 to the display system 107, and displayed on the monitor thereof The space-based differential processing is not confined to simple difference between two data and is carried out for the purpose of removing a signal component originated from surrounding tissue. This space-based differential processing includes highpass filtering of two or more data obtained by transmission carried out in the same raster direction two or more times.

Consequently, an ordinary B-mode display or a harmonic B-mode display can be realized, where the transmission of a wideband ultrasound pulse provides B-mode images of a higher spatial resolution and the depth-dependent control of the band characteristic and others of the band-variable filter gives superior detection sensitivity and a higher S/N. Additionally, the differential processing at each spatial location removes unnecessary echoes from living body tissue, so that a signal from a contrast agent is steadily extracted. The differential processing can be done if the transmission and reception is executed at least two times, which results in higher frame rates compared to the conventional CFM mode. Further the B mode is inherently large in dynamic range. Hence the scanning in the B and harmonic B modes is able to provide contrast agent images, i.e., blood flow images, which is higher in resolution, frame rate, and dynamic range.

In particular, injecting a contrast agent provides perfusion images of living body's tissue. FIG. 40(b) shows a pictorial example of this perfusion image obtained using a contrast agent, as a high-resolution flow image. (FIG. 40(a) illustrates a conventional Doppler velocity image, for comparison, in which perfusion is scarcely depicted.) Since the essential constituent of a contrast agent is microbubbles, increasing the sound pressure of an ultrasound pulse to be transmitted within a predetermined range (within a limitation of the safety standard for the living body) causes the microbubbles to collapse. Reflected signals from collapsing microbubbles include similar signal components to those from moving microbubbles, even when the microbubbles (contrast agent) is at rest in living body's tissue. Therefore, collapsing the contrast agent by an ultrasound pulse and removing unwanted echoes from tissue at rest by the differential processing makes it possible to provide perfusion images of the tissue, even in the B mode, at high resolution, a frame rate, and a dynamic range.

Although there has been known a phenomenon that the microbubbles of the contrast agent collapse due to radiated energy of a transmission ultrasound pulse, speeds of changes of data formed of a signal derived from the contrast agent in the collapsing stage are still useful. Making use of such speed changes can distinguish a signal of a contrast agent being taken in Kupffer's cells and being at rest in relation to tissue from a signal orienting from surrounding tissue which moves slowly.

In this embodiment of the present invention, the sound pressure of an ultrasound pulse is set to an amount that causes no collapse in the agent. The agent oscillates, however, irregularly at the sound pressure causing no collapse. In this oscillation, the phases of signals reflected from microbubbles (contrast agent) when the transmission has done a plurality of times in the same raster directions differ at each time. This shows that the reflected signals are detected as signals identical to those detected from a contrast agent in motion. Hence, a perfusion image that can be seen similarly in the collapse of the microbubbles can be obtained, with no collapse of the contrast agent. Causing the irregular oscillations makes it possible to detect an orthogonal blood flow that has not been detected in a conventional Doppler-based blood flow image. FIG. 4(b) pictorially shows, as a high-resolution flow, an example of a blood flow image in which a blood flow orthogonal with an ultrasound beam is detected. (For comparison, FIG. 41(a) exemplifies an illustration in which an orthogonal flow is observed as a conventional Doppler velocity image.)

Owing to the fact that the contrast agent is not collapsed, it is unnecessary to wait for a time during which alternative microbubbles enter in a scanned region, for such waiting should be done to compensate a decrease in sensitivity once the microbubbles has collapsed. Hence there are provided, from an inherent sense of view, realtime images of perfusion and blood flow using a contrast agent. Imaging is also possible even in the B mode (fundamental wave), providing higher-sensitivity images.

(9) Ninth Embodiment

Figure 16:
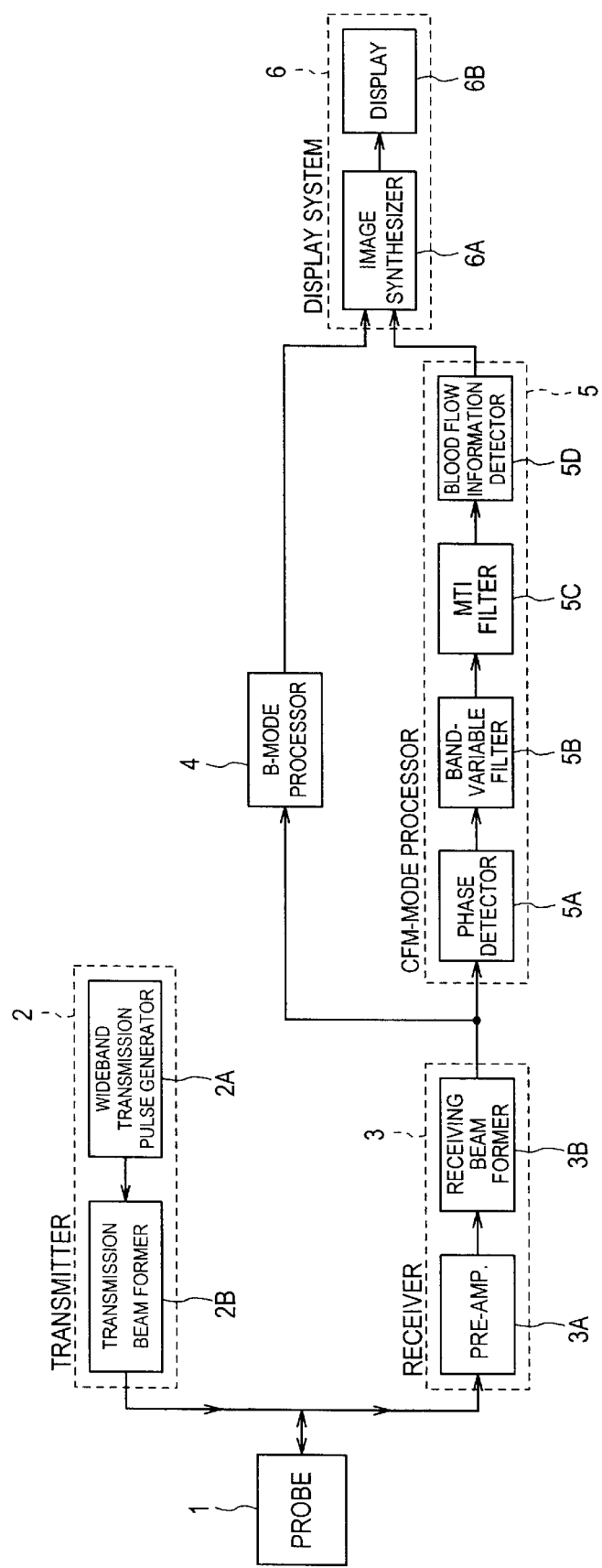
FIG. 16 is a functional block diagram of a diagnostic ultrasound apparatus according to a ninth embodiment of the present invention.

With reference to FIG. 16, a diagnostic apparatus of a ninth embodiment of the present invention will now be described.

This apparatus is used for diagnosis in a CFM (color flow mapping) imaging blood flow information about an object into which a contrast agent is injected from, for example, the vein. The contrast agent used is "Levovist" or "Optison" (trade name), for instance.

FIG. 16 represents a functional block diagram of the diagnostic ultrasound apparatus. This apparatus is shown as an outlined configuration into which various features of the present invention is practically embodied. Those features will be detailed in a tenth embodiment.

As shown therein, the apparatus has an ultrasound probe 1 (hereinafter referred to as a probe) used on an object body, while the apparatus has a transmitter 2 and a receiver 3 both electrically connected with the probe 1, a B-mode processor 4 and a CFM-mode processor 5 both connected to the receiver 3, and a display system 6 electrically coupled with both the processors 4 and 5.

The probe 1 has a function of converting signals bilaterally between ultrasound and electric signals. As one example, the probe 1 has array type of piezoelectric transducers disposed linearly at the tip. The array type of transducers has a plurality of piezoelectric elements disposed in parallel, defining its disposition direction as a scanning direction and a plurality of piezoelectric elements providing respective channels for transmission and reception.

The transmitter 2 comprises a wideband transmission pulse generator 2A generating a wideband transmission pulse, and a transmission beam former 2B exciting transducers of respective transmission channels of the probe 1 by delay-controlling the transmission pulse to convert the pulse into driving pulses. By this configuration, an ultrasound pulse transmitted from the probe 1 into an object has a wide bandwidth that is less than three in the number of burst waves, for example. Thus the transmission and reception are carried out with the wideband ultrasound pulse through the probe 1. Namely, this pulse is scanned at least twice along the same raster direction in a cross section of an object. As the ultrasound pulse is wideband, spatial resolution becomes high.

The probe 1 converts a reflected ultrasound pulse to an electric signal to send it to the receiver 3. The receiver 3 had a pre-amplifier 3A assigned to respective reception channels and a receiving beam former 3B to delay and mutually add received signals. Delay-adding received signals produces an echo signal beam-formed in the same direction as that in transmission. The echo signal is sent to both the B-mode processor 4 and CFM-mode processor 5.

By the B-mode processor 4, the echo signal obtained by transmitting and receiving the ultrasound pulse is detected and produced into tomographic data of the B mode.

On one hand, the CFM-mode processor 5 has, as illustrated in FIG. 16, a phase detector 5A, band-variable filter 5B, MTI filter 5C, and blood flow information detector 5D in this order, from the input side thereof Of these, the phase detector 5A is a constituent quadrature-phase-detecting an echo signal to extract a Doppler signal. The frequency of a reference signal used in the quadrature phase detection is changed in a controlled manner, in real time, in accordance with a location in each raster direction in a cross section of an object. The location corresponds to a depth taken from the object's body surface. Thus, influence on the frequency-dependent loss of signals caused in a living body, which is associated with the transmission and reception of a wideband ultrasound pulse, is eliminated or largely suppressed. Further, the band-variable filter 5B is inserted to filter only an echo signal and to remove noise. The frequency band of this filter 5B is also changed in real time in accord with a depth in the raster direction. This removes noise effectively. In this way, changing both the frequency of the reference signal and the band of the filter at each depth makes it possible to increase an S/N and detection sensitivity, but an ultrasound pulse to be transmitted and received is wideband (high resolution).

The noise-reduced Doppler signal (a train of Doppler data), which still contains a clutter component originating from fixed reflectors and a blood flow Doppler signal, is sent to the MTI filter 5C placed successively. Making use of differences in Doppler shift amount, the MTI filter 5C removes from the Doppler signal the clutter component resulting from fixed reflectors.

The Doppler signal (in detail, blood flow Doppler signal) is then supplied to the blood flow information detector 5D, which computes not merely velocities (mean velocities) of blood flows through the frequency analysis of the signal but also information on blood flow dynamics, such as the power of a reflected signal from blood flow and the dispersion of its velocity distributions, that is, blood flow information. For computing the power, a dynamic range for display is widely set in consideration of scanning carried out with a contrast agent injected. This wide dynamic range prevents power information due to the display saturation from dropping off. Further, in this detector 5D, correspondingly to the foregoing control-mode changes of the frequency of the reference signal, a plurality of aliasing velocities are computed in a velocity mode. The computation of those aliasing velocities can be practiced in various modes, as will be detailed in the following tenth embodiment.

The blood information is sent to the dismay system 6, which comprises an image synthesizer 6A and a display 6B. The image synthesizer 6A produces image data in which the blood flow information in the CFM mode is superposed on, for example, the B-mode topographic imago and the aliasing velocities are written on together. The image data are then displayed on the monitor 6B.

(10) Tenth Embodiment

Referring to FIGS. 17 to 36, a diagnostic ultrasound apparatus of a tenth embodiment of the present invention will now be described. In this embodiment, the configuration of the diagnostic ultrasound apparatus according to the foregoing ninth embodiment will explained more deeply. The story of the entire operation in this apparatus is identical to that in the ninth embodiment.

10.1. Outline of Apparatus Configuration

First, the configuration of this diagnostic ultrasound apparatus will be outlined. The apparatus shown in FIG. 17 comprises, as a whole, like the apparatus of the first embodiment, a probe 11, transmitter 12, receiver 13, B-mode processor 14, CFM-mode processor 15, and display system 16, and further an operation panel 17 used by an operator to input necessary information and a controller 18 taking in the information about operator to produce it into control information sent to predetermined units in the apparatus. The controller 18 has a CPU that calculates various tasks given by software. The controller 18 may be formed by employing digital circuits such as logic circuits as its essential components.

10.2. Configuration and Operation of Each Component

The probe 11 has, by way of example, a construction for electric sector scanning using an array type of transducers, like the ninth embodiment.

10.2.1. Configuration and Operation of Transmission system

Figure 17:
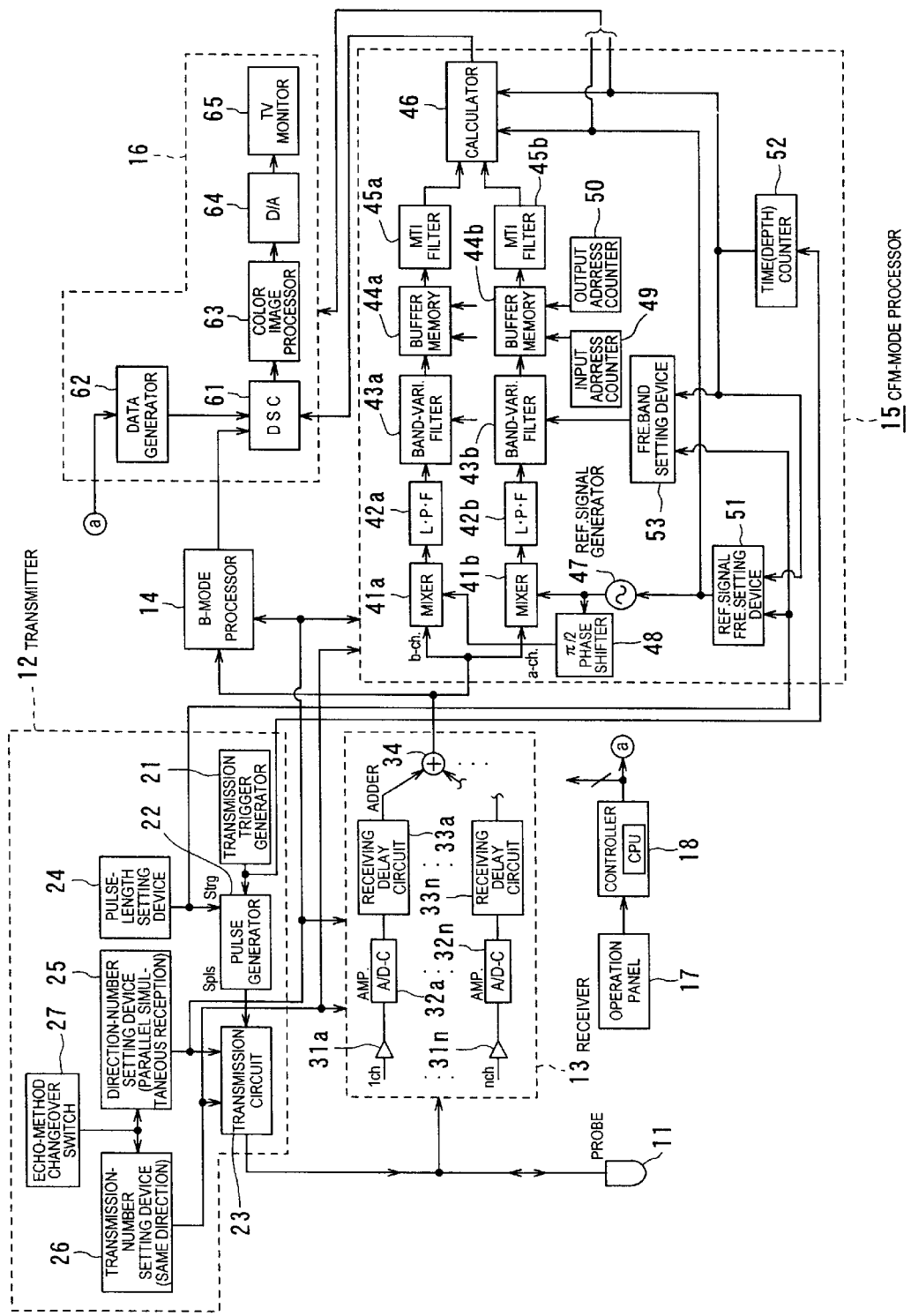
FIG. 17 is a block diagram of a digital type of diagnostic ultrasound apparatus according to a tenth embodiment of the present invention.

As shown in FIG. 17, the transmitter 12 not merely comprises a transmission trigger generator 21, pulse generator 22, transmission circuit 23 in this order in its transmission path but also comprises a pulse-length setting device 24, direction-number setting device 25 for parallel simultaneous reception, transmission-number setting device 26 in relation to the same direction, and echo-method changeover switch 27.

The operation of these constituents will now be outlined. First of all, the transmission trigger generator 21 generates a transmission trigger. The pulse generator 22 generates a transmission pulse responsively to the transmission trigger. Further, the transmission circuit 23 converts the transmission pulse into a driving pulse, and gives it to each transducer of the probe 1. On one hand, the pulse-length setting device 24 is placed to set the length of a pulse, thus sending a setting signal to both the pulse generator 22 and the CFM-mode processor 15. The direction-number setting device 25 is disposed for setting the number of directions for parallel simultaneous reception, thus sending a setting signal to the transmission circuit 23, receiver 13, B-mode processor 14, and CFM-mode processor 15. The direction-number setting device 26 is placed so that the number of times of transmission of an ultrasound pulse in the same direction in transmission, thereby providing a setting signal to the transmission circuit 23, receiver 13, and CFM-mode processor 15. Furthermore, the echo-method changeover switch 27 is a switch that issues changeovers between contrast and non-contrast echo methods, supplying a switch signal to both the direction-number setting device 25 and the transmission-number setting device 26.

These constituents will now be detailed in terms of their configurations and operations.

The transmission trigger generator 21 generates a transmission trigger signal $S_{trg}$ at ultrasound transmission intervals (pulse repetition time) $T_r$. (refer to FIG. 19), the transmission trigger signal $S_{trg}$ being sent to the subsequent pulse generator 22 to trigger it.

The pulse-length setting device 24 provides the pulse generator 22 with information about a transmission frequency $f_0$ and the number of burst waves M which are parameters for determining a pulse length.

Figure 18:
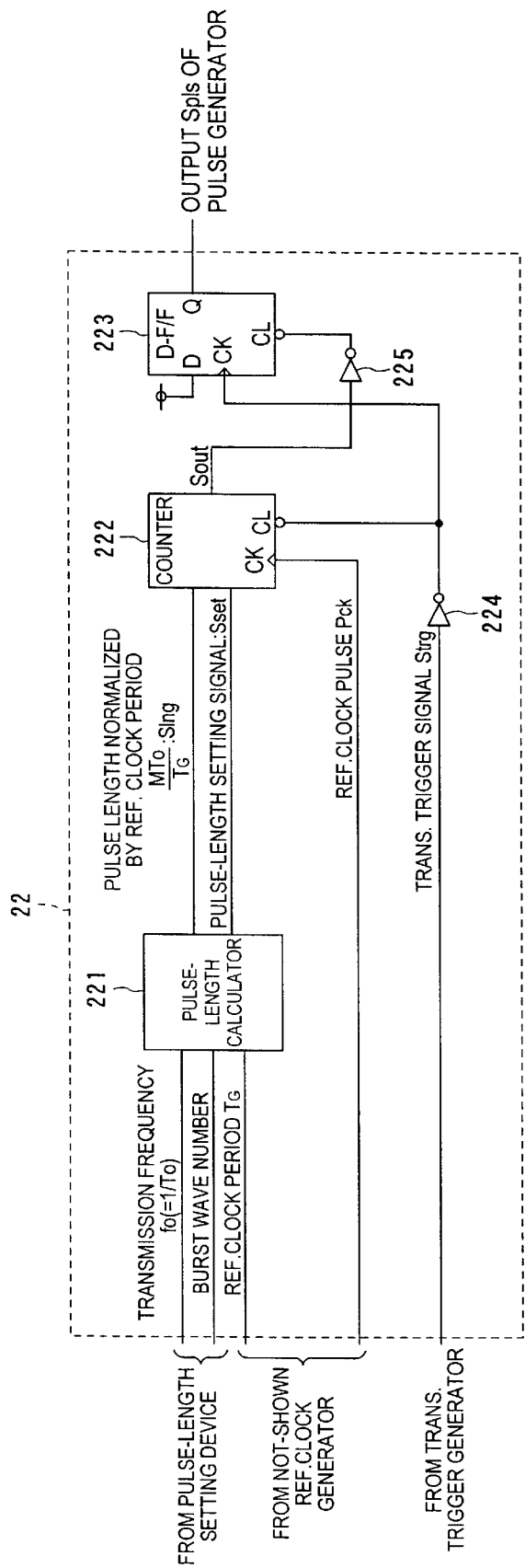
FIG. 18 shows in detail the configuration of a pulse generator employed in the tenth embodiment.

The pulse generator 22 comprises, as shown in FIG. 18, a pulse-length calculator 221, counter 222, D-type flip-flop (D-F/F) 223, and inverters 224 and 225. Of these, the pulse-length calculator 221 receives the transmission frequency $f_0(=1/T_0)$ and the burst wave number M which are given by the pulse-length setting device 24, and further receives a reference clock period $T_G$ provided from a not-shown reference clock generator. Thus, this calculator 221 calculates an expression of "$M \cdot T_0/T_G$" to produce a pulse length scaled at the reference clock and further to outputting a pulse-length signal $S_{lng}$ indicating the pulse length, and outputs a pulse-length setting signal $S_{set}$.

The counter 222 inputs those pulse-length signal $S_{lng}$ and pulse-length setting signal $S_{set}$, a reference clock pulse $P_{ck}$ from a not-shown reference clock generator, and a transmission trigger signal $S_{trg}$ from the transmission trigger generator 21 via the inverter 224 according to the negative logic. An output pulse $S_{out}$ of this counter 222 is provided to a negative-logic clear terminal of the D-F/F 223 via the inverter 225, while the transmission trigger signal $S_{trg}$ is provided a clock terminal thereof via the inverter 224.

Thus, when the transmission trigger signal $S_{trg}$ is on, the counter 222 is cleared and its output signal $S_{out}$ becomes off. The output pulse of the D-F/F, which is an output $S_{pls}$ of the pulse generator 22, is off in the initial state. When the transmission trigger signal falls from on to off, the counter 222 starts measuring the reference clock pulse $P_{ck}$ in response to the last transition, and concurrently the D-F/F 223 is set. Until the counter 222 counts the reference clock pulse $P_{ck}$ up to a value of "$M \cdot T_0/T_G$", the output pulse $S_{out}$ is kept off, during which time the set state of the D-F/F 223 (the output $S_{pls}$ of the pulse-generator 22 is on) is also maintained.

And the counter 222 has finished counting the reference clock pulse $P_{ck}$ up to the value of "$M \cdot T_0/T_G$", the output pulse $S_{out}$ becomes an on state. Responsively to this on state, the D-F/F 223 is cleared. Namely, the output $S_{pls}$ of the pulse generator 22 is also converted into an off state. As a result, the pulse $S_{pls}$ existing in a measurement interval $M \cdot T_0$ counted by the counter 222 is outputted from the pulse generator 22 to the transmission circuit 23.

Figure 19:
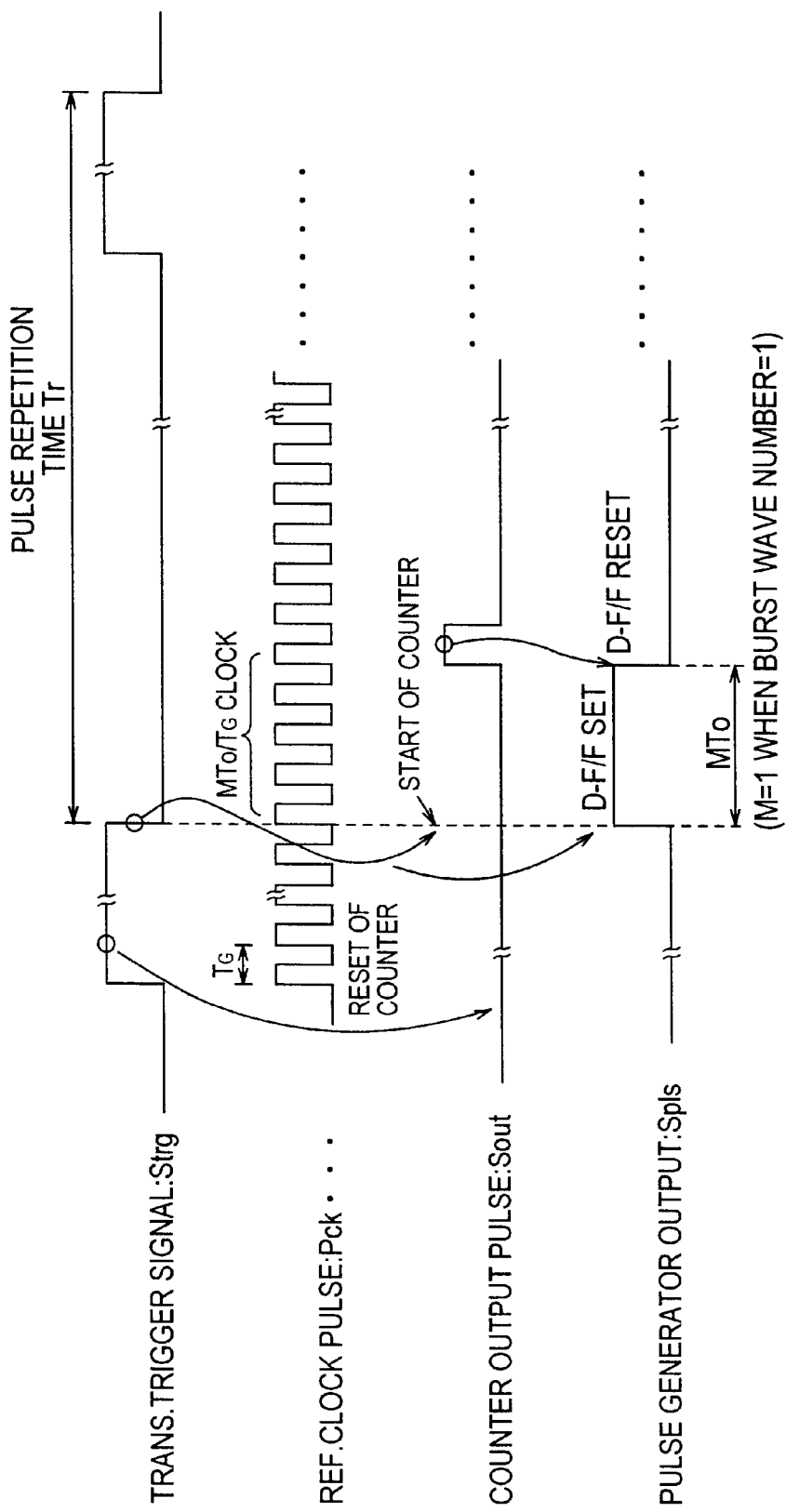
FIG. 19 is a timing chart explaining one example of the operation of the pulse generator.
Figure 20:
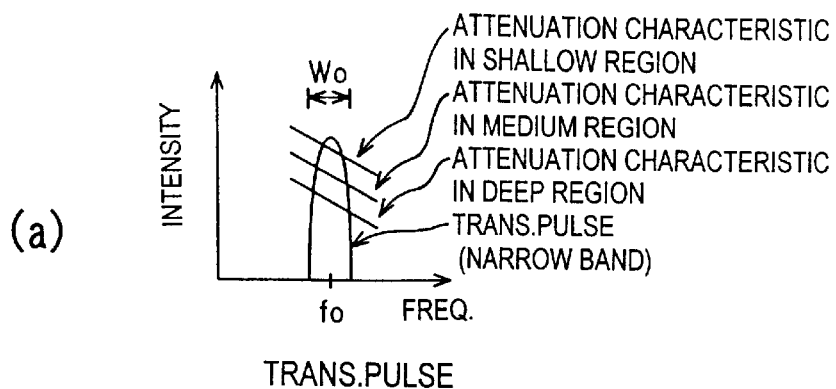
FIG. 20 illustrates waveforms of frequency domains of ultrasound pulses transmitted/received in the conventional apparatus.
Figure 20:
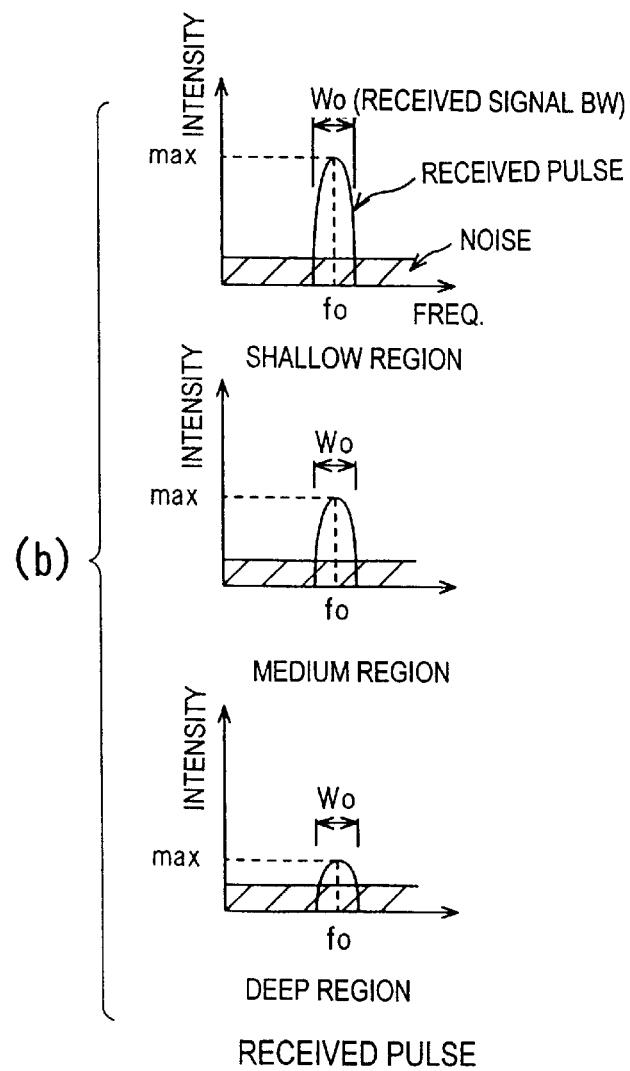
Figure 21:
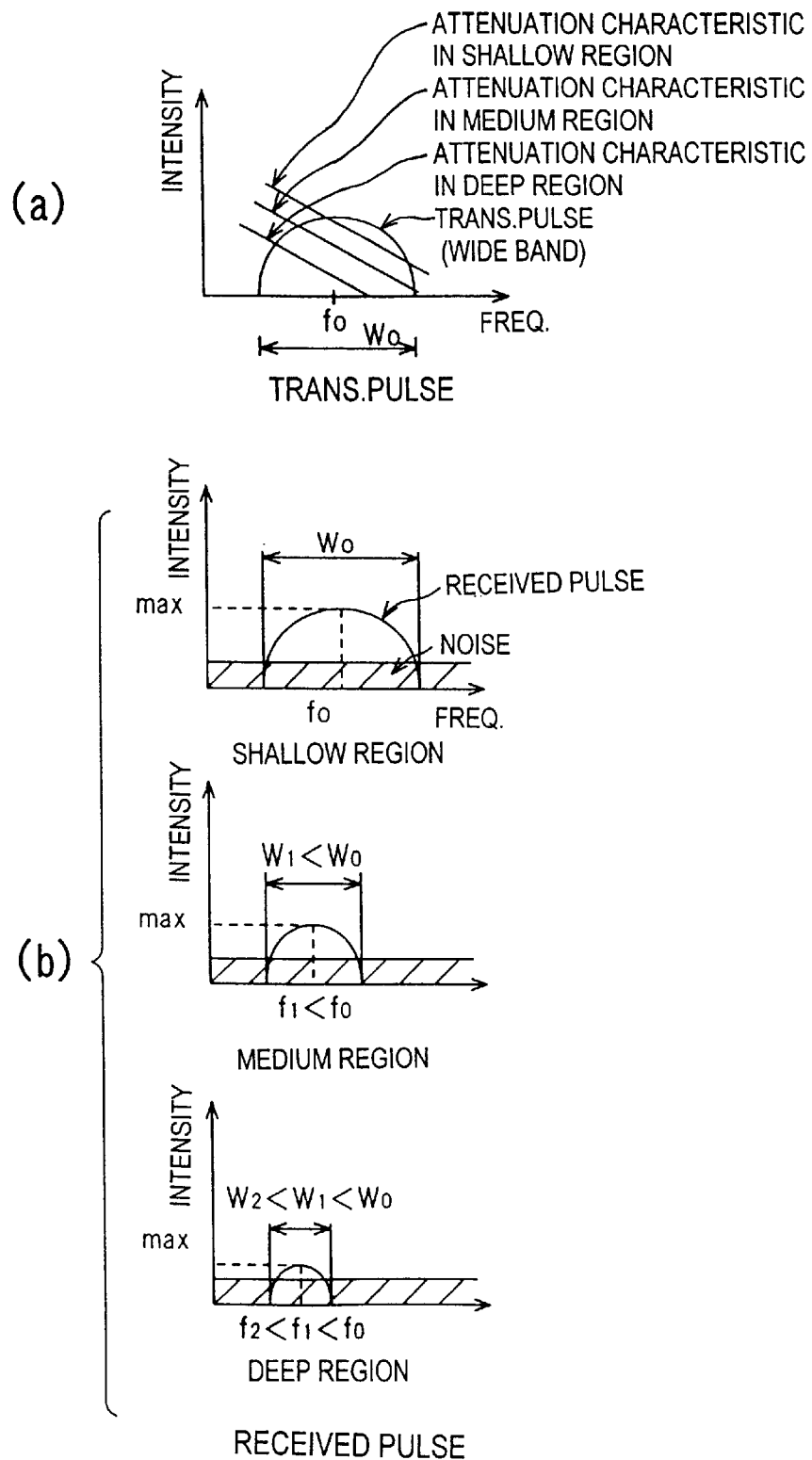
FIG. 21 illustrates waveforms of frequency domains of ultrasound pulses transmitted/received in the embodied apparatus.
Figure 22:
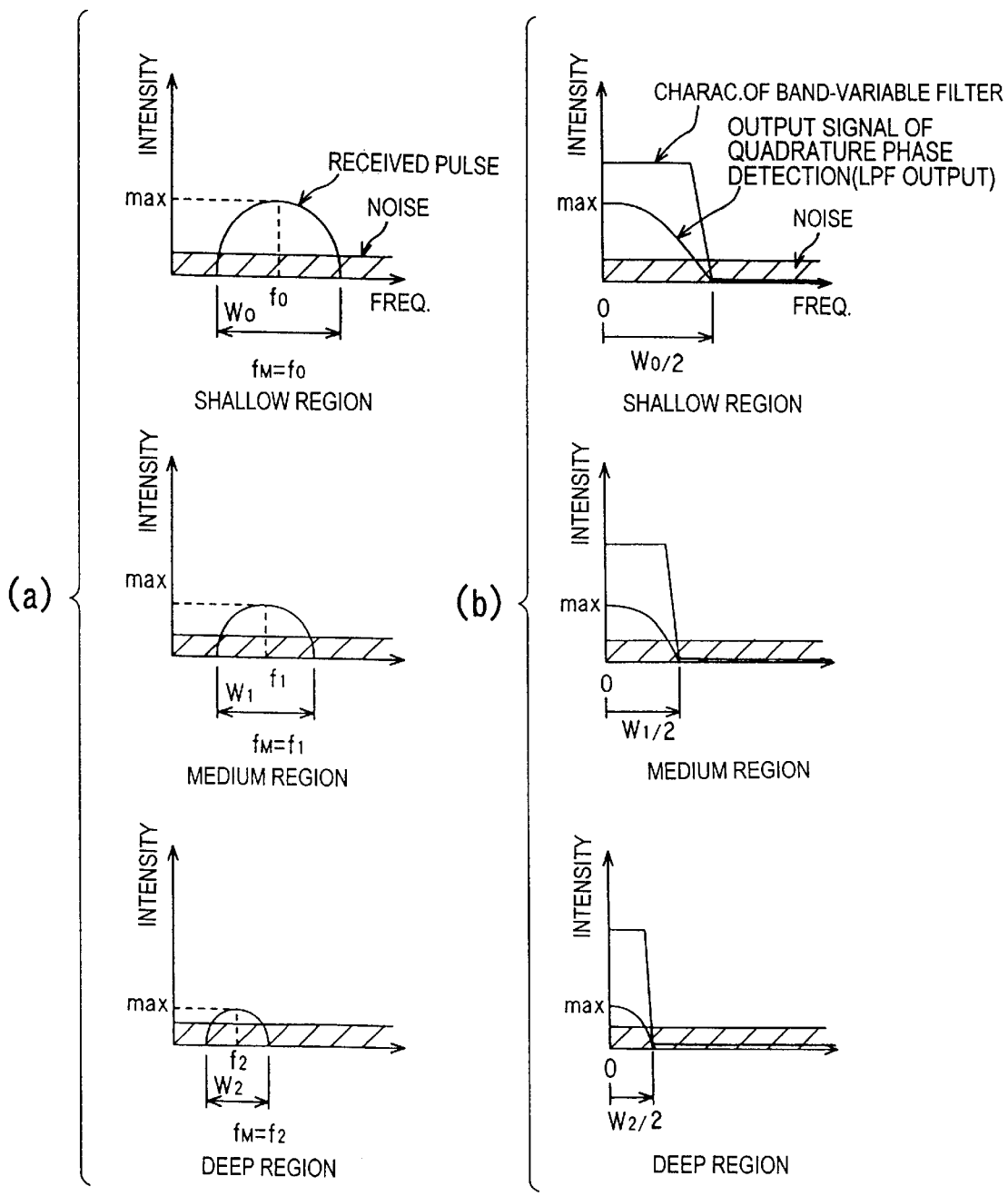
FIG. 22 illustrates characteristics of a band-variable filter adopted in the embodied apparatus.

In this way, the pulse generator 22 generates an electric signal pulse $S_{pls}$ defined by the transmission frequency $f_0$ and one burst wave (in this case, M=1 in "$M \cdot T_0/T_G$") at a pulse repetition time $T_r$ (FIG. 19). This pulse $S_{pls}$ is given the transmission circuit 22.

To the echo-method changeover switch 27, manual setting is made by, for example, an operator about whether ultrasound imaging is to be performed with a contrast echo method or a non-contrast echo method. Information thus-set is given both the setting devices 25 and 26.

In response to this switch information, i.e., according to the contrast or non-contrast echo method, the receiving direction-number setting device 25 automatically changes over the number of times of parallel simultaneous reception differently. On one hand, in response to this switch information, i.e., according to the contrast or non-contrast echo method, the transmission-number setting device 26 automatically and differently changes over the number of times of transmission in the same direction. Namely, the echo-method changeover switch 27 is operated according to if an ultrasound contrast agent is used or not, the parallel simultaneous reception number and the transmission number in the same direction being changed over.

Also provided to the transmission circuit 23 are information indicative of the parallel simultaneous reception number given from the receiving direction-number setting device 25 and information indicative of the transmission number along the same direction in transmission given from the transmission-number setting device 26, which are changed over in compliance with the contrast or non-contrast echo method, as described above.

Therefore, the transmission circuit 23 not only amplifies the pulse $S_{pls}$ given from the pulse generator 22 to produce a driving pulse but also controls, every transmission channel, a delay time of the driving pulse at a delay time pattern considering both the number of beams for parallel simultaneous reception and the beam positions thereof. This control permits the transmission circuit 23 to repetitively provide the prove 11, at the pulse repetition time $T_r$, with the driving pulse having a desired pulse length (transmission frequency $f_0$ and burst wave number=1) delay-controlled toward a desired number of parallel simultaneous reception.

The prove 11 converts the electric driving pulse provided from the transmission circuit 23 into an ultrasound pulse, which is then transmitted into an object body. This transmission is repeated every pulse repetition time $T_r$. During the repetition, the transmission is made by a specified number of times in the same raster direction. The beam of the ultrasound pulse thus-transmitted has a spread beam aperture so that it covers the region of a desired number of reception beams in relation to the parallel simultaneous reception.

In the case of the B-mode transmission, with delay-time control for parallel simultaneous reception accomplished, a delay time of the driving pulse given each piezoelectric transducer is changed by the transmission circuit 23 little by little every ultrasound transmission and reception. This enables a cross section of an object to be scanned in, the B mode. On one hand, in the case of the CFM-mode transmission, with delay-time control for parallel simultaneous reception accomplished, the transmission circuit 23 repetitively supplies each piezoelectric transducer with the driving pulse of which delay time is the same, N times (for example, 16 times) in the same transmitting direction. This allows an ultrasound pulse to repetitively transmitted N times from the probe 11 in the same raster direction. Then with the delay-time control kept, the driving pulse given each piezoelectric transducer is changed in delay time little by little, repeating the transmission similarly. As a result, a cross section of an object is scanned. The pulse transmission for each one frame in the B and CFM modes is performed in an appropriate order, for example, in the alternating order. Still, the transmission frequency $f_0$ and/or voltage (corresponding to the transmission pressure) may be determined separately between the CFM and B modes. Normally, in such a way, transmitting conditions are determined to comply with each mode.

The ultrasound pulse thus-transmitted travels inside the object, and reflects in part at boundaries of which acoustic impedance changes, so that an echo signal emanates. Part or all of the echo signal is received by one or plural transducers of the probe 11, and converted into a corresponding electric echo signal.

10.2.2. Configuration and Operation in Reception Side

The receiver 13, B-mode processor 14, CFM-mode processor 15, and display circuit 16 will then be described.

In parallel with the transmitter 12, the receiver 13 is coupled with the transducers of the probe 11. At the outside of the receiver 13, there are further provided the B-mode processor 14 and the CFM-mode processor 15 arranged in parallel, the outsides of both which processors are coupled with the display system 16.

The receiver 13 has signal processing systems for a plurality of reception channels, which are electrically connected with the respective transducers of the probe. At the input side of each signal processing system of the reception channels, a pre-amplifier 31a (to 31n) is inserted, while at the output side of each pre-amplifier 31a (to 31n), an A/D converter 32a (to 32n), digital type of receiving delay circuit 33a (to 33n) are inserted in this order. Delay outputs from the receiving delay circuits 33a to 33n are added to each other by a digital type of adder 34.

To both the receiving delay circuits 33a to 33n and the adder 34, the number of directions for parallel simultaneous reception, which is from the foregoing direction-number setting device 25, and the number of times of transmission in the same direction, which is from the foregoing transmission-number setting device 26, are provided as specified values different every echo-method.

The echo signal which has received by the probe 11 is taken in the receiver 13 every reception channel as a corresponding electric analog signal. This echo signal is amplified every reception channel, before converted into a digital echo signal. By the receiving delay circuit 33a to 33n, this echo signal is in parallel delay-controlled every reception channel using delay times determined by an entire delay time pattern which is composed by adding L-kinds of delay time pattern differently set in accordance with the parallel simultaneous reception number L to a delay time pattern opposite to that in the transmission. The respective echo signals thus delay-controlled are added to each other by the adder 34, simultaneously, in parallel, for each signal associated with the specified number L for parallel simultaneous reception. This allows a plurality of reception beams to have L-kinds of reception directivities slightly different in direction from each other, but they are almost the same in the transmission, realizing the parallel simultaneous reception. This parallel simultaneous reception number is changed depending on the type of echo method (contrast echo method or non-contrast echo method). Additionally, according to the type of echo method, the transmission number in the same beam (raster) direction is changed, with the result that the receiving delay addition toward the same receiving direction is also changed in a controlled manner.

In the following, for the sake of simplification, the operation for one receiving beam direction will be explained, without omitting the explanation of operation for parallel simultaneous reception (the reception number L). In such case, the totally same operation is carried out for the remaining L-1 directions, temporally in parallel.

10.2.2.1. Configuration and Operation of B-mode Processor

The B-mode processor 14 consists of digital type of circuit groups handling digital signals and has a function of producing B-mode image data from digital-quantity echo signals supplied from the reception circuit 13.

This circuit 14, although not shown in detail, has a logarithm amplifier and an envelope detector. In this circuit 14, an echo signal is first logarithm-amplified by the logarithm amplifier, then an output signal of the logarithm amplifier is subject to envelope-detection in the envelope detector. The detected signal is sent, as tomographic image data, to a frame memory of a DSC of the display system 16. These operations are performed toward each beam derived from the parallel simultaneous reception.

10.2.2.2. Configuration and Operation of CFM-mode Processor

Further, the CFM-mode processor 15 is responsible for producing image data for the observation of blood flow dynamics in the CFM mode and is composed of digital type of circuit groups handing various kinds of processing in the states of digital signals.

The CFM-mode processor 15 has two signal processing systems which split at the input side, and into each system, a mixer 41a (41b), LPF 42a (42b), band-variable filter 43a (43b), buffer memory 44a (44b), and MTI filter 45a (45b) are inserted in this order. The output sides of the MTI filters 45a and 45b are coupled to the display system 16 through the calculator 46.

Of these configurations, a reference signal generator 47 and a π/2 phase sifter 48 are connected to the mixers 41a and 41b. Address counters 49 and 50 for writing and reading data are connected to the buffer memories 44a and 44b.

Further, in this CFM-mode processor 15, there are provided a reference signal frequency setting device 51, time (depth) counter 52, and frequency band setting device 53, which operate as described later.

The pulse-length setting signal provided from the foregoing pulse-length setting device 24 is given both the reference signal frequency setting device 51 and the frequency band setting device 53. Among them, a signal set by the reference signal frequency setting device 51, as will be described later, is supplied to both the reference signal generator 47 and the calculator 46. A signal set by the frequency band setting. device 53, as will be described later, is provided to the band-variable filter 43a and 43b.

Further, the transmission trigger signal $S_{trg}$ generated by the transmission trigger generator 21 is given the time (depth) counter 52. A signal corresponding to a count measured by the counter 52, as will be described later, is sent to the reference signal frequency generator 51, frequency band setting device 53, and calculator 46.

Furthermore, signals generated by the reference signal frequency setting device 51 and time (depth) counter 52 are also sent to the display system 16 which will be described later, and used for display on the screen.

Hereafter, a practical operation of the CFM-Mode processor 15 will now be described, with focusing on a feature of signal processing carried out therein. The feature, which is obtained by performing some modes of the present invention, is that S/N is preferably maintained through signal processing according to the depth from an object body surface, even when the foregoing wideband transmission is performed.

An ultrasound pulse travels in an object body when it is transmitted, during which time the pulse attenuates in energy. The longer the traveling distance, the larger the attenuation. Thus, as a sample point (depth location) becomes deeper in an object, signal intensity (signal sensitivity) is lessened. Additionally this travel has a characteristic depending on frequency, so that the attenuation becomes larger even at the same depth with ultrasound frequency raised. In other words, an attenuation characteristic depending on the frequency (frequency-dependent attenuation) is presented.

Compared to the narrow band transmission, this will be explained. In the narrow band transmission wherein the number of burst waves are three or more, like conventional, a transmission pulse waveform is shown in FIG. 20(a), where the transmission frequency is $f_0$ and there is shown attenuation characteristics of an object. Reception pulse waveforms produced when this narrow-band ultrasound pulse is transmitted are illustrated in FIG. 20(b) concerning respective depths employed as parameters. Because the ultrasound pulse attenuated according to the depth, the sensitivity of a reception pulse is weakened as its reflecting location gets deeper and deeper. However, in this case, the narrow band is set, with the result that a maximum sensitivity frequency at each depth location is sustained at approx. $f_0$. Hence setting the frequency $f_M$ of a reference signal for quadrature phase detection at a constant of about $f_0$ enables the reception to be performed with a maximum sensitivity.

In contrast, the wideband transmission at the number of burst waves=1, which corresponds to one mode of work of the present invention, will now be explained using FIGS. 21(a) and 21(b). FIG. 21(a) represents the waveform of a wideband transmission pulse, where the transmission frequency is $f_0$ and there are also shown attenuation characteristics of an object. FIG. 21(b) represents reception pulse waveforms thereof. Since the ultrasound pulse attenuates depending on the depth, the reception pulse waveforms show that detection sensitivity is lessened as the reflecting location of the reception pulse is deeper and deeper. This is the same as the narrow-band transmission. However, this case is wideband, which results in that a maximum-sensitivity frequency differs in dependence on the depth. Practically, the deeper it is, the lower the maximum-sensitivity frequency is, its amount becomes lower than the transmission frequency $f_0$, and its bandwidth becomes narrower for deeper locations.

In consideration of the reception pulse characteristics associated with such wideband transmission, the following two types of featuring processes are performed, thus S/N being sustained or improved.

A first featuring process is to, as shown in FIG. 22(a), change the frequency $f_M$ of a reference signal in accordance with the detected depth such that the frequency always corresponds to an amount having a maximum sensitivity. Specifically, reference is made to the transmission trigger signal $S_{trg}$ from the transmission trigger generator 21, the time at the depth=0 is determined, and, based on the expression of $$d = T1 \cdot c/2 \tag{3}$$

a relationship between the depth d and the corresponding time T1 thereto can be obtained. c denotes a speed of sound.

This relationship between the time and the depth is calculated by the time (depth) counter 52. The counter 52 receives the transmission trigger signal $S_{trg}$ being outputted from the transmission trigger generator 21 and representing the depth=0, begins to count up the elapsing time T1 at this timing of reception, calculates the depth d from the expression (3) with the use of the counted time T1, and sends one by one the calculated amount to the reference signal frequency setting device 51, frequency band setting device 53, and calculator 46.

Thus, in the reference signal frequency setting device 51, the data (transmission frequency $f_0$ and burst wave number=1) for setting a pulse length is given from the pulse-length setting device 24 and the data of the depth d is given from the time (depth) counter 52. Using both the pulse-length setting data and the depth data, the setting device 51 computes the frequency of a reference signal that is made agree to a maximum-sensitivity frequency of the received pulse at each depth, and gives the reference signal generator 47 a setting signal indicative of this frequency amount.

In effect, an ultrasound pulse is attenuated in an object body at different levels changing according to the frequency of an ultrasound wave, an object's portion, differences in objects themselves, or the like. Thus accuracy is increased by altering the frequency of a transmission pulse so as to measure a maximum-sensitivity frequency of a received pulse at each depth in each diagnostic portion, and by calculating a mean of the maximum-sensitivity frequencies over a large number of objects. This higher-accuracy value (maximum-sensitivity frequency) is written in a ROM, before the ROM is incorporated in the reference signal frequency setting device 51. To read the stored data from the ROM, a transmission frequency $f_0$, such parameters as the burst wave number M (less than three), a depth, an object's diagnostic body are given the ROM as addresses. This permits a corresponding maximum-sensitivity frequency to be read.

A portion to be diagnosed of an object is specified by an operator via a switch panel (not shown) of the operation panel 17. A CPU (not shown) of the apparatus recognizes and codes specified information, and sets a coded signal in the reference signal frequency setting device 51 via an appropriately set buffer in the CFM-mode processor 15.

The reference signal generator 47 generates, as a reference signal $f_M(d)$ (: a function of depth), a signal of which frequency is the same as that at each depth, which is sent in real time from the reference signal frequency setting device 51 as described above. The reference signal $f_M(d)$ thus-formed is supplied to the mixers 41a and 41b constituting part of the quadrature phase detector.

The mixers 41a and 41b and LPFs 42a and 42b constitute the quadrature phase detector to quadrature-phase-detect a digital amount of echo data, so that Doppler data are extracted at each depth location for each transmission/reception. Due to the fact that the frequency of the reference signal generated from the reference signal generator is changed accordingly to the setting signal from the reference signal frequency setting device 51, as described above, its amount varies in accordance with the depth, providing in real time the frequencies which always offer an approximately maximum reception sensitivity. This reference signal is sent to; one mixer 41b and the π/2 phase sifter 48. The phase sifter 48 provides the reference signal with an exact 90-degree phase difference, then the reference signal is sent to the other mixer 41a.

As a result of it, an echo signal outputted from the receiver 13 is multiplied by the reference signals by the mixers 41a and 41b. This multiplication causes signals of which phases differ to each other by 90 degrees. The signals are obliged to pass the respective LPFs 42a and 42b so that harmonic components caused by the mixing are removed, providing Doppler data in the base band. In this way, the same location in a scanned cross section, i.e., the same raster, is scanned a plurality of times N, and for each time of scanning, Doppler data are extracted from an acquired echo signal through the quadrature phase detection. This quadrature phase detection enables the separation of detection (separation of directions) between blood cells toward to the probe and away from the probe.

Accordingly, since the reference signal for phase detection in this quadrature phase detection is in real time adjusted to a frequency always giving a maximum reception sensitivity, the reception sensitivity is kept high at any time, even when the wideband transmission is performed.

The Doppler data thus-extracted, which are always at nearly maximum reception sensitivities are then sent to the band-variable filters 43a and 43b, respectively.

A second featuring process in the CFM-mode processor 15 is concerned with the band-variable filters 43a and 43b.

The band-variable filters 43a and 43b are formed into BPFs (band-pass filters), where their frequency bands are altered in real time accordingly to the setting signal from the frequency band setting device 53. Practically, it is changed in accordance with the frequency band of a received pulse changing in compliance with the depth, thereby noise is removed effectively. In other words, as shown in FIG. 22(b), the frequency characteristic of each of the band-variable filters 43a and 43b are almost made agree to the frequency band of Doppler data produced by the quadrature phase detection. The control is done at each depth location in almost real time.

A practical technique will now be explained. When the priority is given to an improvement in S/N, it is enough that the totally same band characteristic as that of a received pulse is given the band-variable filters 43a and 43b at each depth location. But in this case, the range resolution is deteriorated to some extent. Therefore, the characteristics of the band-variable filters 43a and 43b may be adjusted a little not so as to deteriorate the resolution in the range direction.

Like the reference signal frequency setting device 51, in order to set the characteristics of the frequency band setting devices 43a and 43b, it is preferred to employ a way of incorporating a ROM (not shown) in the frequency band setting device 53. In this ROM, previously stored is a band value enhanced in both accuracy and reliability by measuring the frequency band of a received pulse at each dept in each portion with the transmission frequency changed, and by calculating a mean over the measurements for a large number of objects. Into the frequency band setting device 53, as described above, the data are supplied from the pulse-length setting device 24, time (depth) counter 52, and controller 18, respectively. These data represent the transmission frequency $f_0$, burst wave number M (=less than three), depth location, and object's portion to be diagnosed. These figures are converted into address signals in the frequency band setting device 53, and the address signals are given the ROM incorporated in the setting device. By this, the address signals, i.e., the data of a frequency band characteristic that corresponds to the input data are read from the ROM, and the read data are then sent, as a setting signal, to the band-variable filters 43a and 43b.

As a result, in the filters 43a and 43b, as pictorially shown in FIG. 22(a) as a shallow region, medium region, and deep region, the frequency band characteristic at each depth location is changed in real time according to the setting signal. Thus, filtering in accord with the frequency band of a received pulse (Doppler data) efficiently removes noise down to a sufficiently low level and maintains the S/N at a preferable level or improves it, even when the wideband transmission is carried out.

Particularly, the foregoing first and second features, that is, "the control of the reference signal frequency according to the depth" and "the control of the frequency band of the noise filter according to the frequency band of the received pulse," are used together, thereby a high S/N being acquired, even when the transmission pulse is wide in band.

In this way, the Doppler data that have experienced noise reduction are sequentially loaded into the Doppler buffer memories 44a and 44b.

The Doppler signal is, as described before, a train of data consisting of amounts of phase shifts (amounts of Doppler shifts) per unit time of a reflected signal from blood flow, which is acquired by scanning the same sample location (depth location) at a pulse repetition time $T_r$. A blood flow velocity is obtained from the Doppler signal. To calculated this, data of the received pulses acquired by scanning the same raster position, for example, N times, are sequentially loaded into the buffer memories 44a and 44b.

From the time-sequential Doppler signals, each of which have been acquired by scanning, N times, each sample position in a scanned cross section, a blood flow velocity at each sample position is calculated. However, the Doppler signal at this stage mixedly includes a reflected wave from objects in motion such as blood cells and a reflected wave from stationary objects almost in rest, such as blood vessel wall and tissue. Moreover, in terms of reflected intensity, the latter (objects in rest) becomes a dominant. Additionally, the frequencies of reflected waves from blood cells undergo Doppler shifts, while reflected waves from the stationary reflecting members (clutter components) have not almost experienced the Doppler shifts. To remove clutter components by utilizing such differences in Doppler shift, the MTI filters 45a and 45b are inserted in the channels a and b, respectively.

A train of N-piece Doppler data that has been read in the time-sequential direction at each sample position from each of the buffer memories 44a and 44b, that is, a Doppler signal, is given each of the MTI filters 45a and 45b. Thus, based on the differences in Doppler shift, most of the clutter components are removed, leaving only a reflected wave of which component is mostly from blood cells, thereby a blood flow component being to the calculator 46.

In general, the calculation processing in the calculator 46 includes calculation of the mean (Doppler frequency) of a spectrum, its dispersion, or intensity (power) of reflected signals of blood cells at each sample position corresponding to each depth; the calculation is based on frequency analysis of the N-piece Doppler data in the time-sequential direction. The calculated values are sent, as blood flow information, to the successive display system 16.

The calculator 46 relates to a circuit according to the third feature of the present invention, which is then detailed.

Figure 23:
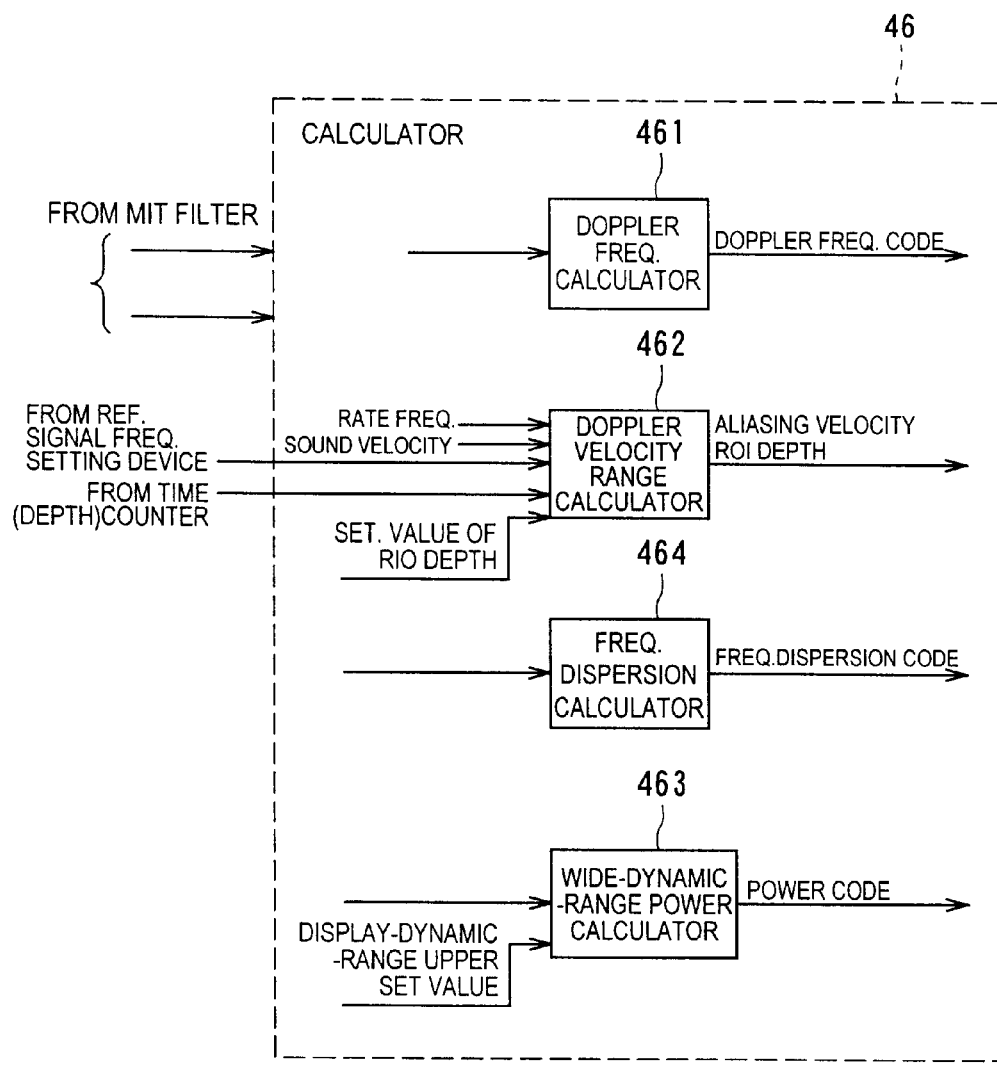
FIG. 23 is a block diagram showing the configuration of a calculator installed into the embodied apparatus.
Figure 24:
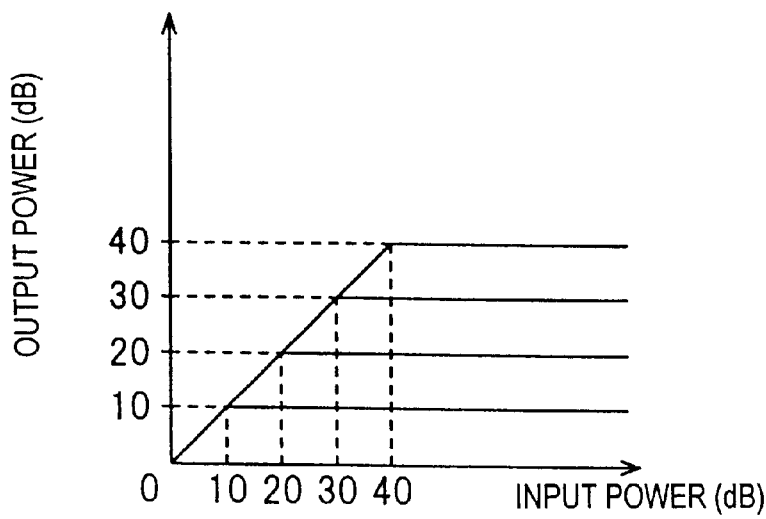
FIG. 24 illustrates a dynamic range used in the embodied apparatus, which is shown compared to conventionally used one.
Figure 24:
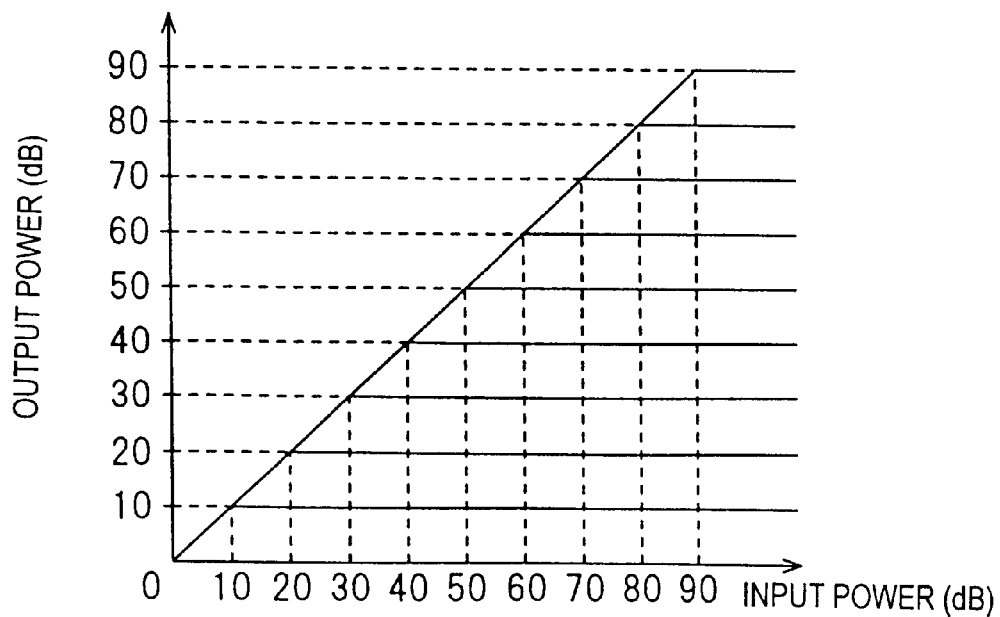

The calculator 46 is, as shown in FIG. 23, provided with a Doppler frequency calculator 461, a Doppler velocity range calculator 462 substituted for a conventional Doppler velocity calculator, and a wide-dynamic-range power calculators 463 as an alternative for a conventional power calculator. Further there is provided a frequency dispersion calculator 464 in the calculator 46. The Doppler velocity range calculator 462 calculates an aliasing velocity range on the basis of information supplied from the time (depth) counter 52 and the reference signal frequency setting device 51. The wide-dynamic-range power calculator 463 is incorporated to enlarge the dynamic range of power display.

The Doppler frequency calculator 461 comprises frequency analyzers such as an auto-corrector, which respectively receives Doppler signals corresponding to a real part and an imaginary part and being outputted from the MTI filters 45a and 45b. In this calculator 461, the Doppler frequency (mean velocity) of a spectrum is analyzed at each sample position, and the resultant value is converted into a corresponding Doppler frequency code and outputted. This analysis result is also given the frequency dispersion calculator 464.

First, the aliasing velocity is explained as bellow. As described before, the Doppler velocity vd is normally calculated on this expression (the foregoing expression (1) is recited again);

$$v_d = f_d \cdot c / 2f_M \cdot \cos\theta$$

(wherein $f_d$: Doppler frequency, c: sound speed, $f_M$: reference signal frequency for mixer, θ: angle between an ultrasound beam and a blood flow). In the conventional, c and $f_M$ are set to constants in the expression (1), but θ differs at each sample location in a scanned cross section. Hence, for the same Doppler frequency, resultant Doppler velocities generally differ from each other (referred to as the angular dependency of Doppler velocities). To eliminate this angular dependency, an alternative technique is employed as follows, through it is has not been put in practical use. In other words, since an original Doppler velocity is possible to calculate when θ=0 in the expression (1) and an aliasing velocity $v_r/2$ at such occasion is expressed by the foregoing expression of:

$$v_r/2 = (f_r/2) \cdot (c/2f_M)$$

(the foregoing expression (2) is recited), a value of the aliasing velocity calculated on this expression is displayed together with a color bar.

In the case of this embodiment, it is meaningless that such display technique is adopted as it is. The countermeasures to improve S/N has been adopted for the wideband transmission, and the frequency $f_M$ of the reference signal is changed in real time according to the depth of sample locations. The reason is, therefore, that the aliasing velocity varies in accordance with the depth of each sample location.

In contrast, in this embodiment, a plurality of aliasing velocities are displayed. To realize this, there are practical techniques including a way of indicating velocities at the shallowest region and the deepest region of a ROI that shows a region displayed on CFM-mode imaging, a way of indicating velocities at the depth=0 and the deepest region of a tomographic image, and a way of indicating, in addition to the above velocity indication, a velocity at a marker placed in a display image. An alternative way of indication may be adopted. In this example, the way of indicating the aliasing velocities at the shallowest and deepest regions in a ROI will be explained.

To accomplish this indication, to the Doppler velocity range calculator 461 of the calculator 46, a rate frequency $f_r$, sound speed c, and ROI-depth setting values d1 (the shallowest region), and d2 (the deepest region) are supplied from the controller 18, the depth d is supplied from the time (depth) counter 52, and the reference signal frequency $f_M$ is supplied from the reference signal frequency setting deceive 51 in synchronism with the depth d, respectively. The Doppler velocity range calculator 461 always monitors the depth d, during which time, when d=d1 is recognized, using a reference signal frequency $f_{Md1}$, an aliasing velocity $v_{rd1}$ at the ROI's shallowest region is calculated by the expression of:

$$v_{rd1}/2=(f_r/2)\cdot(c/2f_{Md1}) \quad (4),$$

which is based on the foregoing expression (2). Like this, using a reference signal frequency $f_{Md2}$ when the depth d=d2 is recognized, an aliasing velocity $v_{rd2}$ at the ROI's deepest region is calculated by the expression of:

$$v_{rd2}/2=(f_r/2)\cdot(c/2f_{Md2}) \quad (5),$$

which is based on the foregoing expression (2). These aliasing velocities $v_{rd1}/2$ and $v_{rd2}/2$ are loaded in a frame memory of a DSC of the display system 16 in combination with the ROI depths d1 and d2.

The dynamic range for display in the power mode will then be described.

This concerns a fourth feature of the present invention. The dynamic range for display is, in effect, a factor that will be determined within the calculator 46. As gradations for display, 64 gradations (gradations from 0 to 63) are exemplified, but other gradations are available.

In processing of received echo signals, to avoid feeble signals from being dropped off, gain is normally set with taking a level of noise as a reference. Thus when the dynamic range for display is too narrow compared to the signal intensities, signals having larger intensities than the display dynamic range will be saturated. In this case, regardless of signal amounts causing the saturation, such signals are flat displayed at an upper limit of the display dynamic range. The gradation is all expressed at a maximum level of 63. Namely, an image is, in part, no gradation providing a flat feeling. Display resolution is also low, thus significant power information being lost.

A blood flow signal obtained in the ordinary CFM that has been conventionally performed is a signal based on the power of reflected signals from blood cells. Because of reflected signals from blood cells are weak in intensity, the display dynamic range of the power is narrow accordingly, being approximately 40 dB at most. Assuming that the display dynamic range is 40 dB, FIG. 24 will be now explained.

FIG. 24(a) shows an example of an input/output power characteristic when determining an ordinary display dynamic range conventionally carried out. An upper limit of the output power, i.e., a display dynamic range can changeably set to 10, 20, 30 and 40 dB, respectively. Because the gradation for display is fixed at 64, this changeable setting requires that a display dynamic range be set as widely as possible and made agree to signal intensities within a range where no saturation is caused, without loosing gradations. For example, if a maximum signal intensity of an object is 16 dB and the display dynamic range is 40 dB, the actual display gradations become 64(16 dB/40 dB)=26 gradations, lessening gradations and darkening an image. This results in a decrease in diagnosis performance. When being set at 20 dB, the actual display gradations is 64(16 dB/20 dB)=51 gradations, increasing gradations and brightening an image, in addition to an improved diagnosis performance.

Thus, as for the power of a reflected signal form blood flow, it is normally enough to determine the display dynamic range at 40 dB at most. Contrary to it, in the case that a contrast agent is injected into an object, echo signals are enhanced in reflected intensity by an amount of a few tens of decibels. Therefore, when the display dynamic range is determined at the maximum range, 40 dB, saturation occurs throughout an image in most cases, resulting in no or less gradations that provide an image with a flat feeling. This decreases diagnostic performance as well.

In this embodiment, as shown in FIG. 24(b), the display dynamic range is enlarged to, for example, 90 dB at most, in which the changeable setting is allowed by an amount of 10 dB, step by step, from 10 dB to 90 dB. This enables the display dynamic range to be determined in an optimum fashion, even when signals of higher intensities are reflected from microbubbles in a contrast agent, as well as signals reflected from blood cells.

To realize this, as shown in FIG. 23, the wide-dynamic-range power calculator 463 is placed in the calculator 46. While the configuration of the calculators 463 is not shown, there are provided a calculator located at the input side to calculate a power amount and a ROM located at the output side. Data indicative of the input/output characteristic shown in FIG. 24(b) are loaded in the ROM. Thus the calculator 463 calculates power amounts on reflected signals from blood flow, which are outputs of the MTI filters 45a and 45b. The power amounts and an upper limit set for the display dynamic range are given the ROM as bits of address information. The upper limit is determined by, for example, making the CPU of the controller 18 send an amount specified by an operator via the operation panel 17 to the wide-dynamic-range power calculator 463. A power amount that corresponds to an input power amount is read form the ROM, and power codes are outputted based on the input/output characteristic of FIG. 24(b).

On one hand, the frequency dispersion calculator 464 of the calculator 46 calculates a piece of dispersion information about a velocity distribution from the frequency analysis results, and outputs corresponding frequency codes thereto.

In this way, the Doppler frequency codes, frequency dispersion codes, power codes, and information on both the aliasing velocities and the ROI depth are sent, as Doppler data representing blood flow dynamics, to a DSC of the display system 16.

10.2.2.3. Configuration and Operation of Display System

The display system 16 is provided with a digital scan converter (DSC) 61 having two types of frame memories for B mode and CFM mode and a read/write control circuit thereof, a data generator 62 generating display data, such as a ROI, color bar, scales, and annotations to be displayed, a color image processor 63 for coloring pixels, a D/A converter 64, and a TV monitor 65 for display. The digital tomographic image and Doppler data outputted from the B-mode and CFM-mode processors 14 and 15 are loaded into the frame memories of the DSC 61, respectively. Additionally, various pieces of operational information given by an operator via the operation panel 17 are supplied to the data generator 62 via the controller 18.

In the DSC 61, the data stored in both the B-mode and CFM-mode frame memories are individually read in the standard TV system. Concurrently, pixels spatially common in both the frame memories are selected alternatively, pixel by pixel, and one frame of image data are formed in which a CFM image (information about contrast agent, i.e., Doppler data indicative of blood flow dynamics, such as blood flow velocities, dispersion, and power) in the CFM mode is superposed on a B-mode tomographic image (background image). Data to be displayed generated by the data generator 62 are also superposed on this image data. Doppler data residing in the image data thus-formed are color-processed by the color image processor 63. The image data thus-produced are converted into analog signals at intervals by the D/A converter 64, thereby being displayed as a CFM image on the TV monitor 65.

Figure 25:
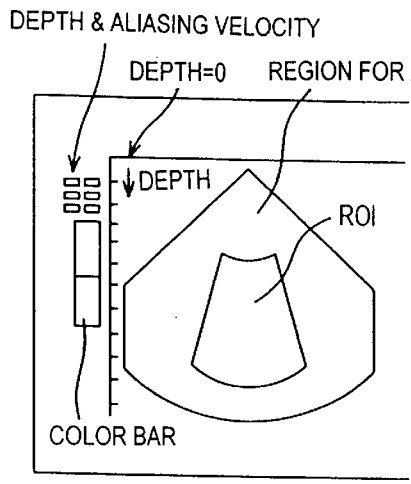
FIG. 25 exemplifies images and color bars displayed on the monitor of the embodied apparatus.
Figure 25:
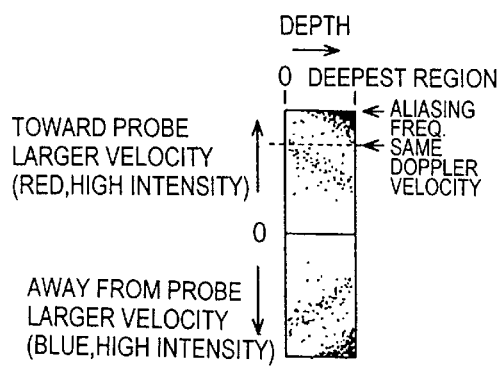
Figure 25:
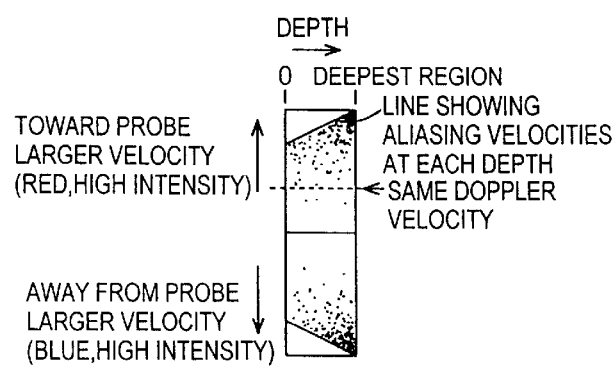
Figure 25:
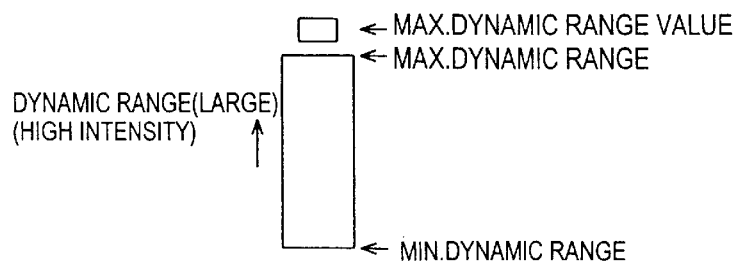

FIG. 25 shows examples of this display. FIG. 25(a) shows one example is played on the monitor screen. In the central portion thereof, a B-mode tomographic image is displayed, in which a convex-like ROI is set in part, and a CFM image is displayed superposedly within the ROI. At the corners thereof, there are displayed various data in the numeral and scale forms (refer to dotted line portions in the figure). Further, in the figure, at the left side of the screen, a scale indicting the depth from the probe is displayed, and a color bar is located adjacent thereto.

FIG. 25(b) shows a color bar showing blood flow velocities, as one example of the color bar. Like the conventional, this color bar shows blood flow velocities of which directions in relation to the probe are separated to each other. Similarly, at upper specified positions above the color bar, upper and lower limits of the depth range of a ROI and aliasing velocity according to the depth range are displayed approximately in real time in windows assigned to them.

Additionally, representative examples of the color bar for the velocities are shown in the figures (c) and (d), respectively. The example shown in (c) has, along the longitudinal axis, Doppler frequencies (blood flow velocities) of which directions are separated, and, along the lateral axis, the range of the depth, wherein the same velocity is colored in the same hue. Both the ends of the longitudinal axis show aliasing frequencies ±fr/2. In this embodiment, the frequency of the reference signal is controlled according to the depth in the depth direction. Hence, even for the same Doppler frequencies, calculated Doppler velocities are different from each other, and aliasing velocities to the aliasing frequency fr/2 are different depending on the depth. Thus, there is provided a color map (bar) pictorially shown in (c). On one hand, a velocity color bar shown in (d) has, along the longitudinal axis, Doppler frequencies of which directions are separated, and, along the lateral axis, the range of the depth, wherein the same velocity is colored in the same hue. Because the frequency of the reference signal is changed according to the locations in the depth direction, this color bar also provides aliasing velocities that are different according to the depth. Thus, an aliasing velocity at each depth forms the color map (bar) illustrated in (d).

Further, a color bar of the power is exemplified in FIG. 25(e). At an upper position which is adjacent to the color bar (herein, 64 gradations as an example) indicating the dynamic range, like the conventional, a maximum dynamic range value changeable from 10 dB to 90 dB is displayed.

10.3. Entire Operation and Advantages

As described above, in this diagnostic ultrasound apparatus, in response to the driving signal delayed in transmission by the transmitter 12, the probe 11 transmits an ultrasound pulse into an object. The transmitted pulse returns as a reflected wave and is detected by the probe 11. Thus, an electric echo signal is outputted from the probe 11, and in the receiver 13, the echo signal is converted into a digital signal, before being reception-delayed. The echo signal is then sent to both the B-mode and CFM-mode processors 14 and 15 in parallel. As a result, as described before, tomographic data in a scanned cross section and CFM image data representing blood flow dynamics therein are formed. In the display system 16, the CFM image data are superposed on the tomographic image data and displayed as a final CFM image on the TV monitor 65.

In obtaining this CFM image, the diagnostic ultrasound image can be obtained various advantages, as described below.

Figure 26:
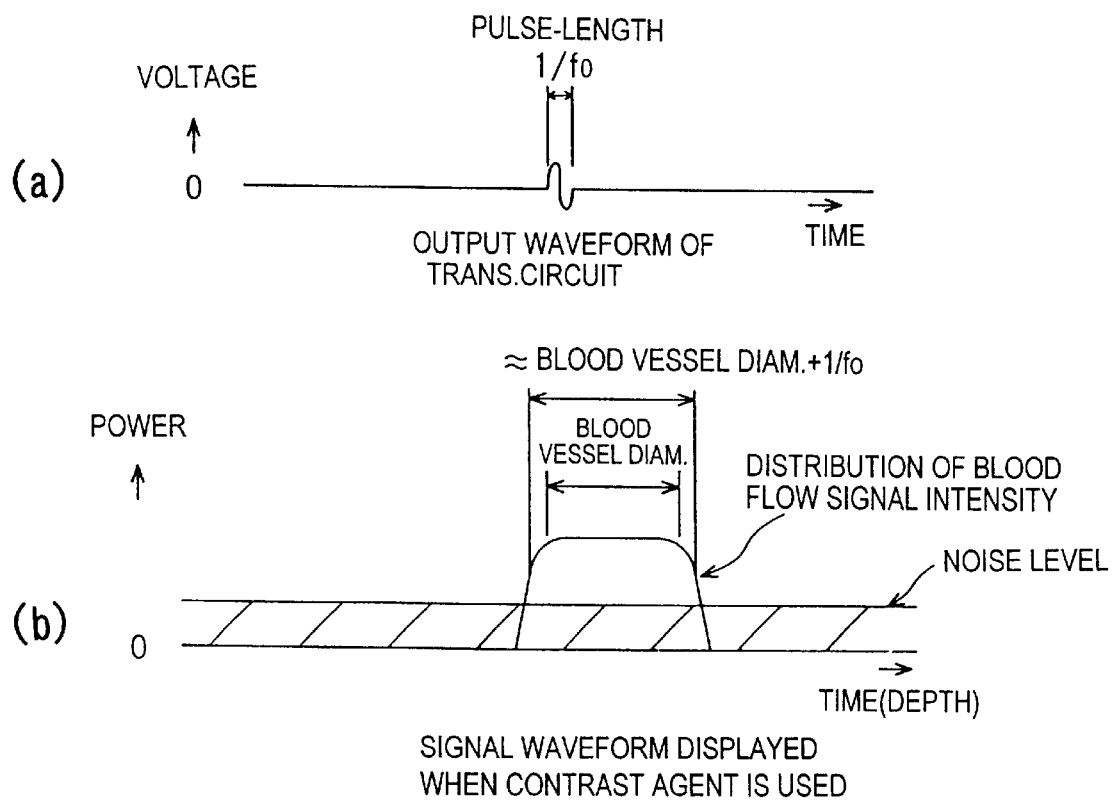
FIG. 26 shows illustrations of a wideband ultrasound pulse transmitted and the spatial resolution thereof.

First, an advantage on the wideband transmission is given. On the TV monitor 65, as exemplified in FIG. 25(a), a ROI is displayed on the CFM image. The CFM image within the ROI is as follows. When scanned with no contrast agent injected (non-contrast method), the CFM image is increased in sensitivity. In particular, if scanned with the contrast echo method where a contrast echo is injected in an object, the detection sensitivity for blood flow is enhanced by approximately a few tens of decibels. In performing the contrast echo method, in this embodiment, as mentioned before, the frequency band of an ultrasound pulse is set to a wideband in the transmitter 12. This permits blood flow signals to be detected with a higher spatial resolution. For example, in the case of the burst wave number=1, as shown in FIG. 26, there can be provided a CFM image (blood flow image) of which range resolution is noticeably improved compared to the conventional CFM. In consequence, there occurs almost no blooming.

Second, there is provided an advantage owing to the fact that the parallel simultaneous reception number can be increased. Since the detection sensitivity is normally raised by nearly a few tens of decibels for scanning in which a contrast agent is injected into an object, the detection sensitivity can fully be secured even for a spatially spread transmission beam and the increased parallel simultaneous reception number. Thus, the direction-number setting device 25 increases the parallel simultaneous reception number for the contrast echo method in comparison with the non-contrast echo method, if commanded by the echo-method changeover switch 27. This largely raises the number of frames (i.e., temporal resolution), making it possible to observe blood flow dynamics in higher realtime performance. As one example, while 6 frames/sec. is obtained for an ordinary CFM with no parallel simultaneous reception, 24 frames/sec. for the parallel simultaneous reception number=4 directions, and 48 frames/sec. for the parallel simultaneous reception number=8 directions, respectively. The realtime performance is improved remarkably.

Third, there is an advantage given by decreasing the transmission number in the same direction to be transmitted. As a blood flow signal is low in intensity, it is likely to be influenced by noise, so that information about blood flow dynamics is easy to fluctuate. To lessen this influence, in detecting blood flow signals, an ultrasound pulse is transmitted and received 16 times in the same raster direction to detect from the same signal source (sampled location in a scanned cross section) a plurality of blood flow data lining up in the time-sequential direction, and then a mean Doppler frequency (Doppler velocity) over those data is obtained. In the case of the contrast echo method, a detection sensitivity toward blood flow is enhanced by an amount of nearly a few tens of decibels, improving S/N and almost eliminating the influence of noise on blood flow signals. This means that a higher S/N and more stable blood flow signal are obtained even when the number of times of transmitting an ultrasound pulse in the same raster direction is lowered. Considering this fact, if the contrast echo method is commanded via the echo-method changeover switch 27, the transmission number in the same direction is lowered by the transmission-number setting device 26. This lowering enables the number of frames per sec. (corresponding to the temporal resolution) to swell, providing CFM images having higher realtime performance. As one example, when 6 frames per sec. is obtained for an ordinary CFM, the number of frames will double up to 12 frames per sec. if the number of transmission times is decreased by ½, accomplishing a largely improved realtime performance.

In the embodiment, the realtime performance is increased remarkably highly, because the number of directions for parallel simultaneous reception is increased and at the same time, the number of times of transmission in the same direction is decreased. If necessary, either technique may be employed.

By the way, the foregoing CFM-mode processor has a configuration in which BPFs functioning band-variable filters are inserted after the quadrature phase detector channel by channel. In this BPF location, the design for BPFs can be simplified.

Still, in the diagnostic ultrasound apparatus of this embodiment, the receiving to processing devices 13 to 15 are composed of digital type of circuits by placing A/D converters immediately after the receiving amplifiers. This digitization contributes to both improving performance of receiving and processing circuits, and diversifying processing, in addition to stability of circuit operation.

Additionally, the CFM mode in this embodiment is not confined to a mode in which a CFM image is overlaid on a tomographic image, but various display modes can be performed.

Still further, it is preferred that the present invention is applied to a diagnostic ultrasound apparatus for both the contrast echo method with the injection of a contrast agent to raise blood flow detection sensitivity and the non-contrast echo method with no contrast agent, but with higher blood flow detection sensitivity.

Further, imaging for the collapse of a contrast agent and imaging for irregular oscillations of microbubbles of a contrast agent, witch has been described in the eighth embodiment, can be applied to this tenth embodiment as well.

10.4. Modifications of Tenth Embodiment

As to the foregoing tenth embodiment, there can be provided various embodiments as follows.

(First Modification)

Figure 27:
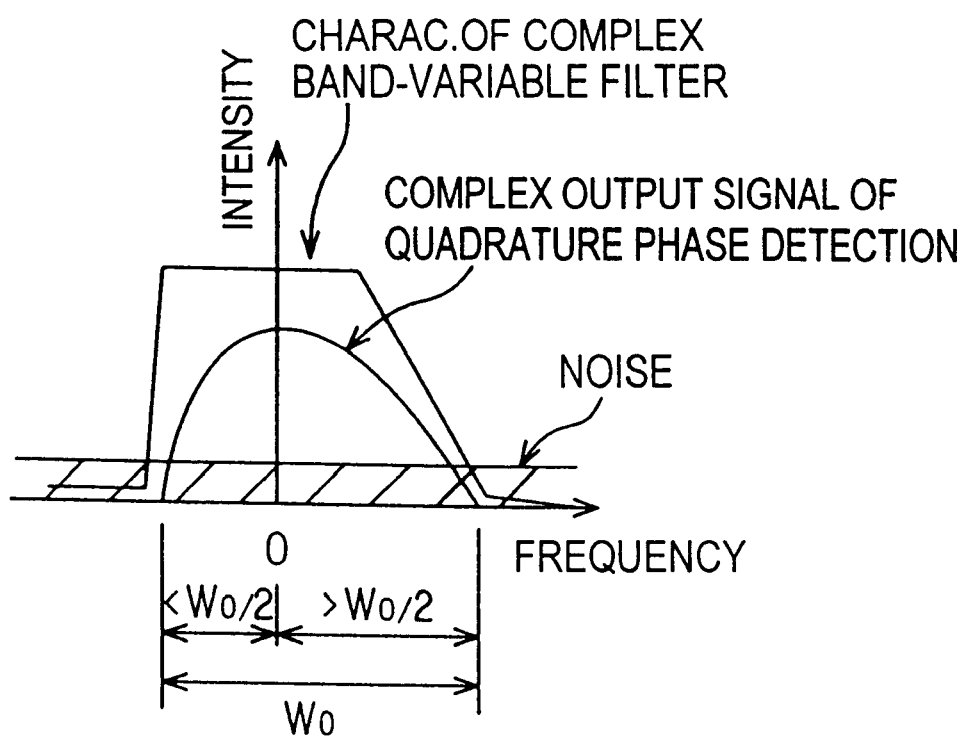
FIG. 27 explains another characteristic of the band-variable filter.
Figure 28:
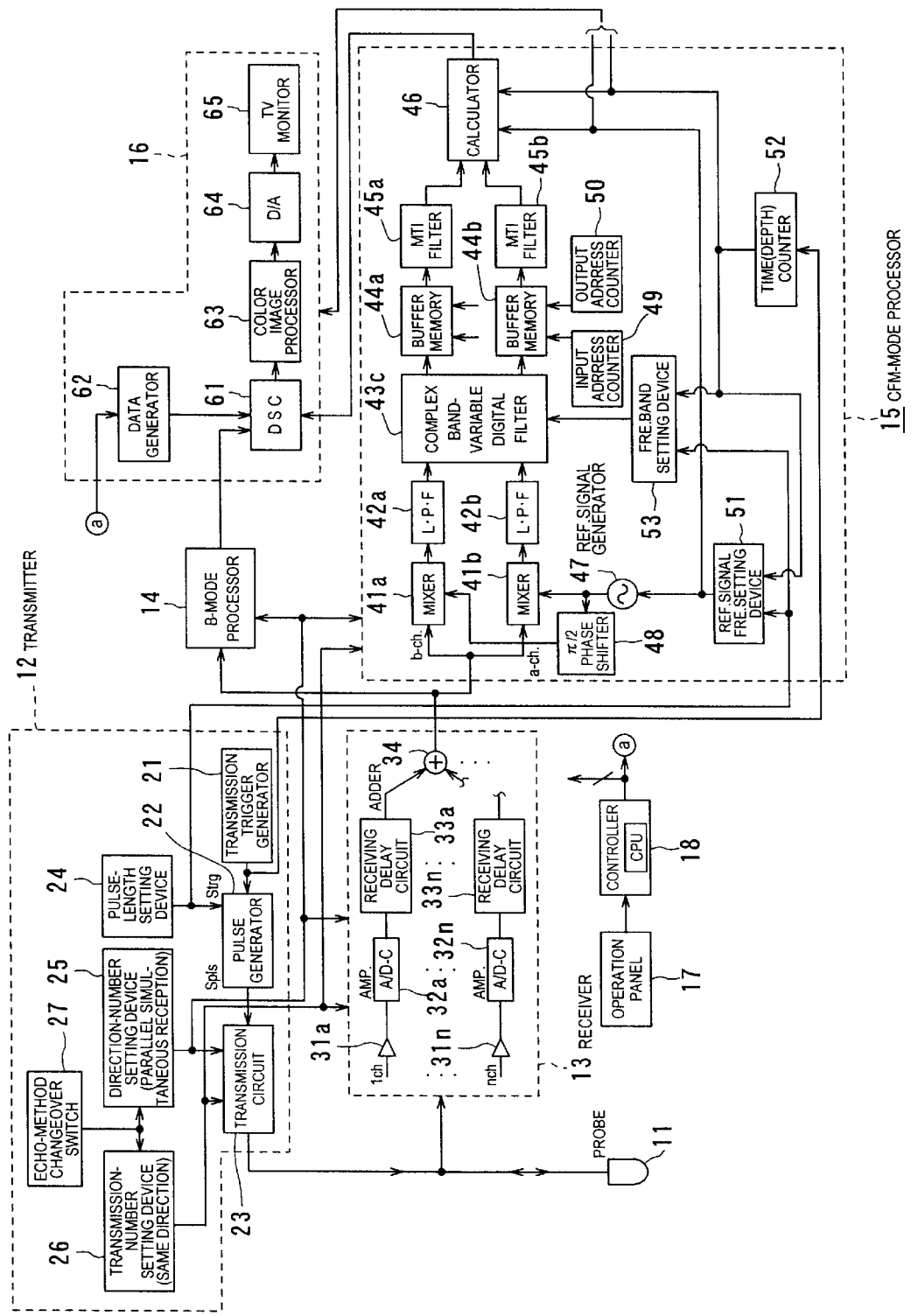
FIG. 28 is a block diagram showing a diagnostic ultrasound apparatus according to a first modification of the tenth embodiment, which uses a complex band-variable digital filter.
Figure 29:
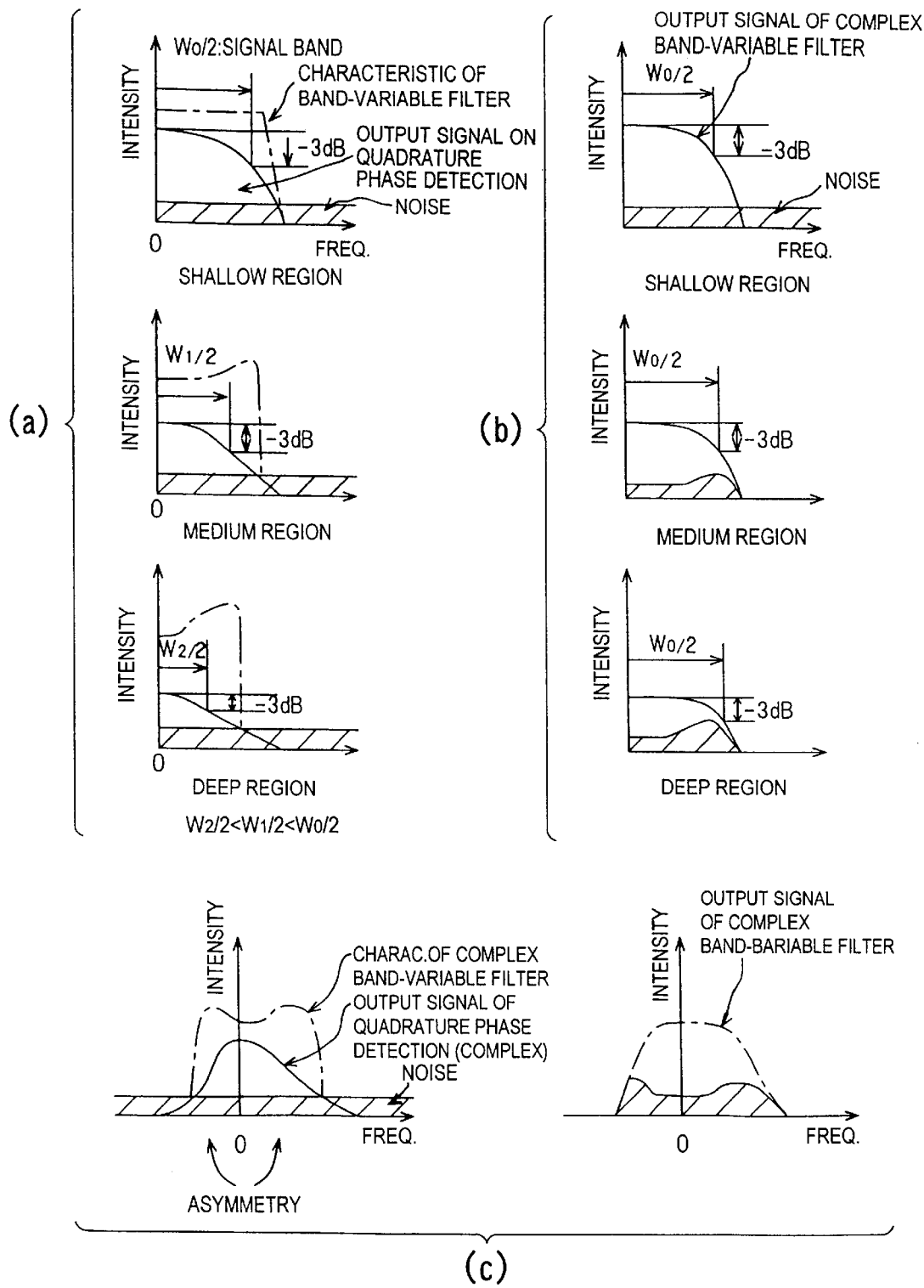
FIG. 29 illustrates other characteristics of the band-variable filter according to a second modification of the tenth embodiment.

A first modification is concerned with the band-variable filters 43a and 43b inserted in the CFM-mode processor 15. A frequency spectrum of an ultrasound pulse, produced by quadrature-phase-detecting a received echo, is almost symmetric between higher and lower frequency sides divided at the center of a maximum sensitivity frequency $f_0$, $f_1$, or $f_2$ (refer to FIG. 21). Therefore, the band-variable filters 43a and 43b are enough even if they are of a real-number type, thus employing a real-number type of filter to be placed in each channel in the foregoing embodiment. Actually, however, such a frequency spectrum is not completely symmetric, as shown in FIG. 27. Therefore, the band-variable filters can be formed into a complex-number type into which a filter of two channels are combined, and its spectrum characteristic can be set asymmetrically to a maximum sensitivity frequency made agree to a quadrature-phase-detected output signal, resulting in that accuracy in filtering is raised more. Such complex band-variable filter 43c is placed in a diagnostic ultrasound apparatus shown in FIG. 28.

(Second Modification)

A second modification is related to controlling only the band characteristic of a band-variable filter, which leads to a great improvement for range resolution. This modification is able to greatly improve range resolution, although the improvement in S/N is not so much as the foregoing embodiment.

In this modification, the frequency fm of the reference signal is always kept almost constant. (The depth is not changed, unlike the foregoing configuration. However, depending on the following desired frequencies, the depth may be changed appropriately.) But as illustrated in FIG. 29(a), according to the frequency spectrum of an input signal changing on the depth, the band characteristics of the band-variable filters 43a and 43b are changed in a controlled manner depth by depth. As a result, as shown in FIG. 29(b), the output signals of the band-variable filters 43a and 43b do not depend on the depth, and are always kept at the same frequency band or thereabouts. (Further, in general, a desired frequency band characteristic is obtained at every depth.) This makes it possible that S/N is improved and a signal band is widened, leading to a substantially improved range resolution, especially at deep locations. That is, a superior range resolution comparable to that of a transmission ultrasound pulse having a wideband characteristic can be sustained.

In this case, the band-variable filter may be of a real-number or complex-number type. In cases a complex-number type of filter is employed, as shown in FIG. 29(c), its band characteristic can be determined asymmetrically, providing a higher degree of freedom in designing the characteristic. As to this modification, it is prefers that the band-variable filter is formed as digital filters so as to have flexibility in design of filtering characteristics.

(Third Modification)

A third modification relates to setting the band of the band-variable filter in using a contrast agent.

Figure 30:
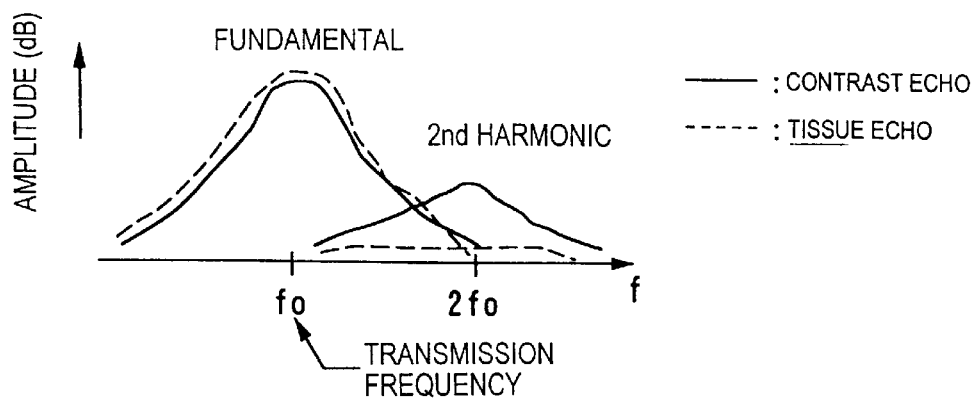
FIG. 30 shows spectra of a third modification according to the tenth embodiment.

Owing to non-linear oscillation characteristics, an echo signal that has reflected from microbubbles composing an essential constituent of a contrast agent contains harmonics, sub-harmonics, and ultra-harmonics. As an example, FIG. 30 shows spectrums of a fundamental wave and $2^{nd}$ harmonic for one transmission wave. In this transmission, the fundamental wave and $2^{nd}$ harmonic are, in part, superposed with each other and returned. Since the fundamental wave is stronger than the $2^{nd}$ harmonic in the intensity of signal from a contrast agent and the $2^{nd}$ harmonic of a tissue echo (clutter) is weak in intensity, an echo from the contrast agent becomes a dominant from the viewpoint of the $2^{nd}$ harmonic.

Figure 31:
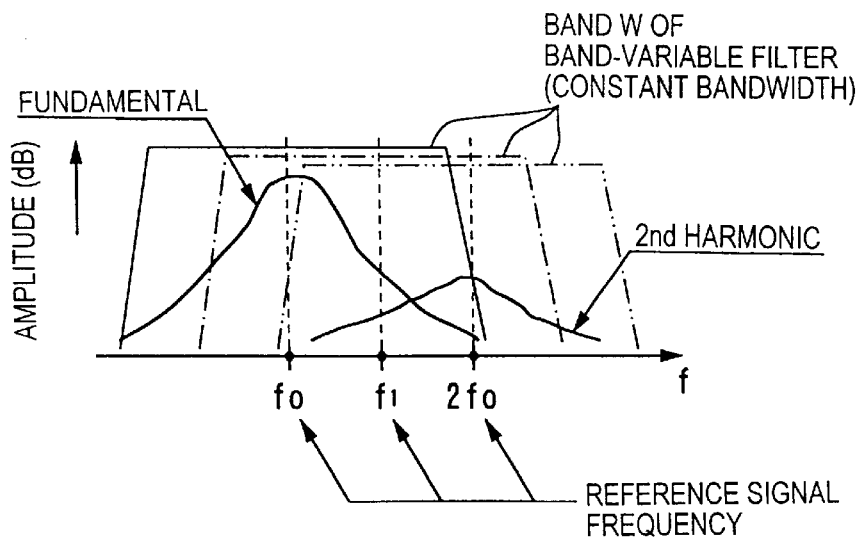
FIG. 31 is an illustration of band shifts provided by a band-variable filter used in the third modification.

Therefore, as shown in FIG. 31, with the bandwidth W of a band-variable filter unchanged, the frequency of a reference signal is shifted, for example, to $f_0$, $f_1$, and $f_2$. When giving priority to the sensitivity of a contrast agent, the fundamental wave is mainly received, whilst when giving priority to a removal capability of clutter, the $2^{nd}$ harmonic is mainly received. This permits signals to be used effectively. For instance, the sensitivity is fully secured in a shallow region in general, thus the band is set mainly toward the $2^{nd}$ harmonic to give priority to the clutter removal capability. (The frequency of a reference signal is located at the center frequency $2f_0$ of the $2^{nd}$ harmonic, for example.) By contrast, in a deep region, the band is set mainly toward the fundamental wave to give priority to sensitivity so that the influence of attenuation in a living body is compensated. (The frequency of a reference signal is placed at the center frequency $f_0$ of the fundamental wave, by way of example, wherein an MTI filter located after the filter essentially removes the clutter.) Moreover, in an intermediate depth, it is preferred that the band is set so that both the waves are mixed. (In this case, by way of example, the frequency of a reference signal is located at the central frequency $f_1$ between the fundamental wave and the $2^{nd}$ harmonic.)

Figure 32:
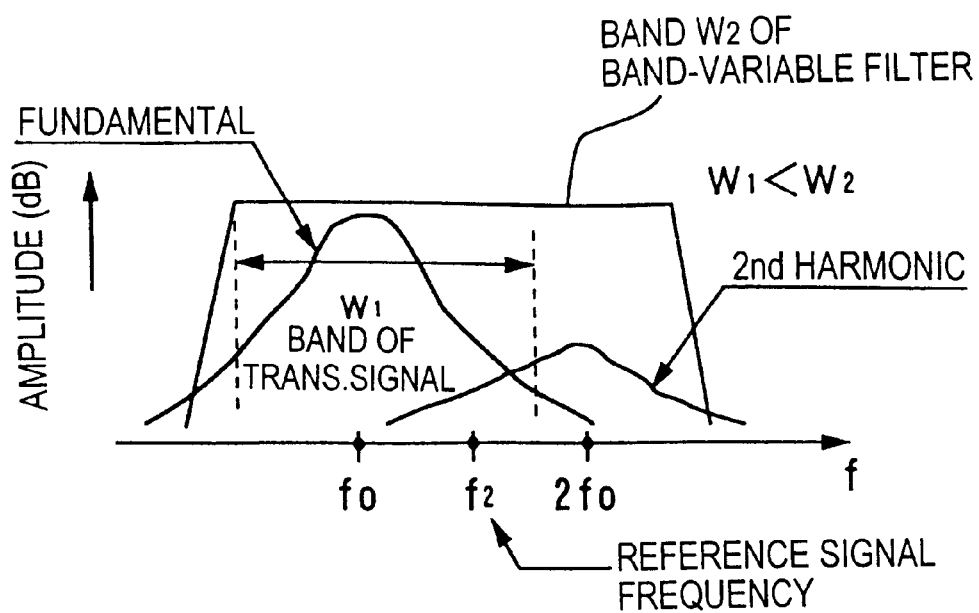
FIG. 32 is an illustration for giving a bandwidth to the band-variable filter describing the third modification.

Another setting technique is shown in FIG. 32, in which a reference signal frequency $f_2$ is located between the center frequency $f_0$ of the fundamental wave and the center frequency $2f_0$ of the $2^{nd}$ harmonic. And, compared to a transmission band $W_1$, the band $W_2$ of a band-variable filter is widened to bridge both the fundamental wave and the harmonic. This provides a signal of which band is wider than the transmission band and the range resolution is increased.

In the foregoing FIG. 4, the spectrum of a signal received from a contrast agent is shown. An echo signal reflected by microbubbles composing an essential constituent of a contrast agent contains harmonics, sub-harmonics, and ultra-harmonics due to non-linear oscillations. Thus, in the case that a harmonic B-mode image is displayed, a reception signal band is set so that it includes non-linear signal bands as well as the transmission signal band.

(Fourth Modification)

Figure 33:
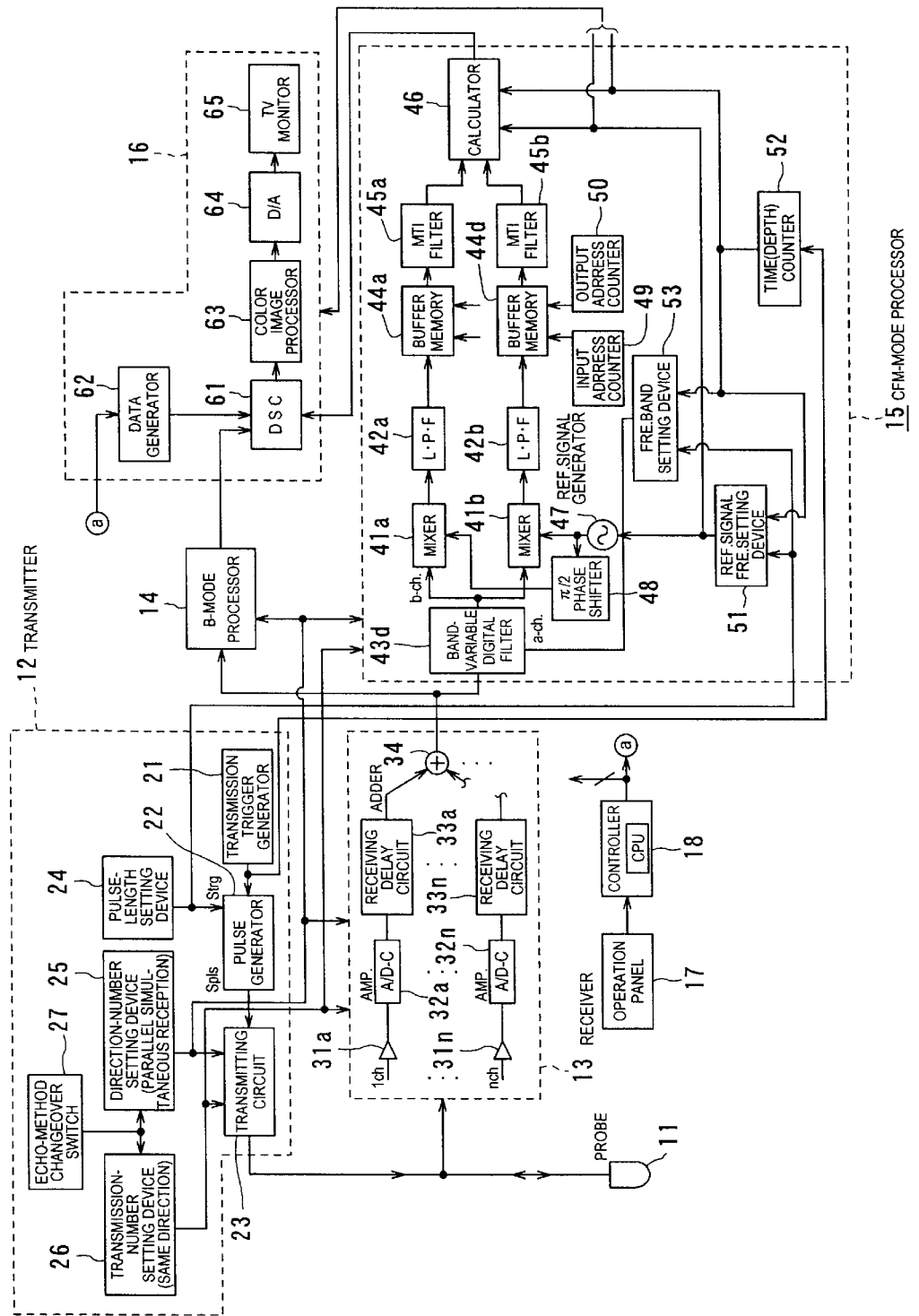
FIG. 33 shows in block form a diagnostic ultrasound apparatus according to a fourth modification of the tenth embodiment, wherein a band-variable digital filter is inserted before a detector.

A fourth modification relates to a location at which the band-variable filter is placed. The band-variable filter is not necessarily confined to a configuration where it is inserted after the LPFs of the quadrature phase detector. Instead, as shown in FIG. 33, the band-variable filter 43*d* may be placed before the mixer of the quadrature phase detector. In such a case, the band-variable filer 43*d* should perform filtering at a radio frequency, but it is enough that the filter is prepared for only one channel.

(Fifth Modification)

Figure 34:
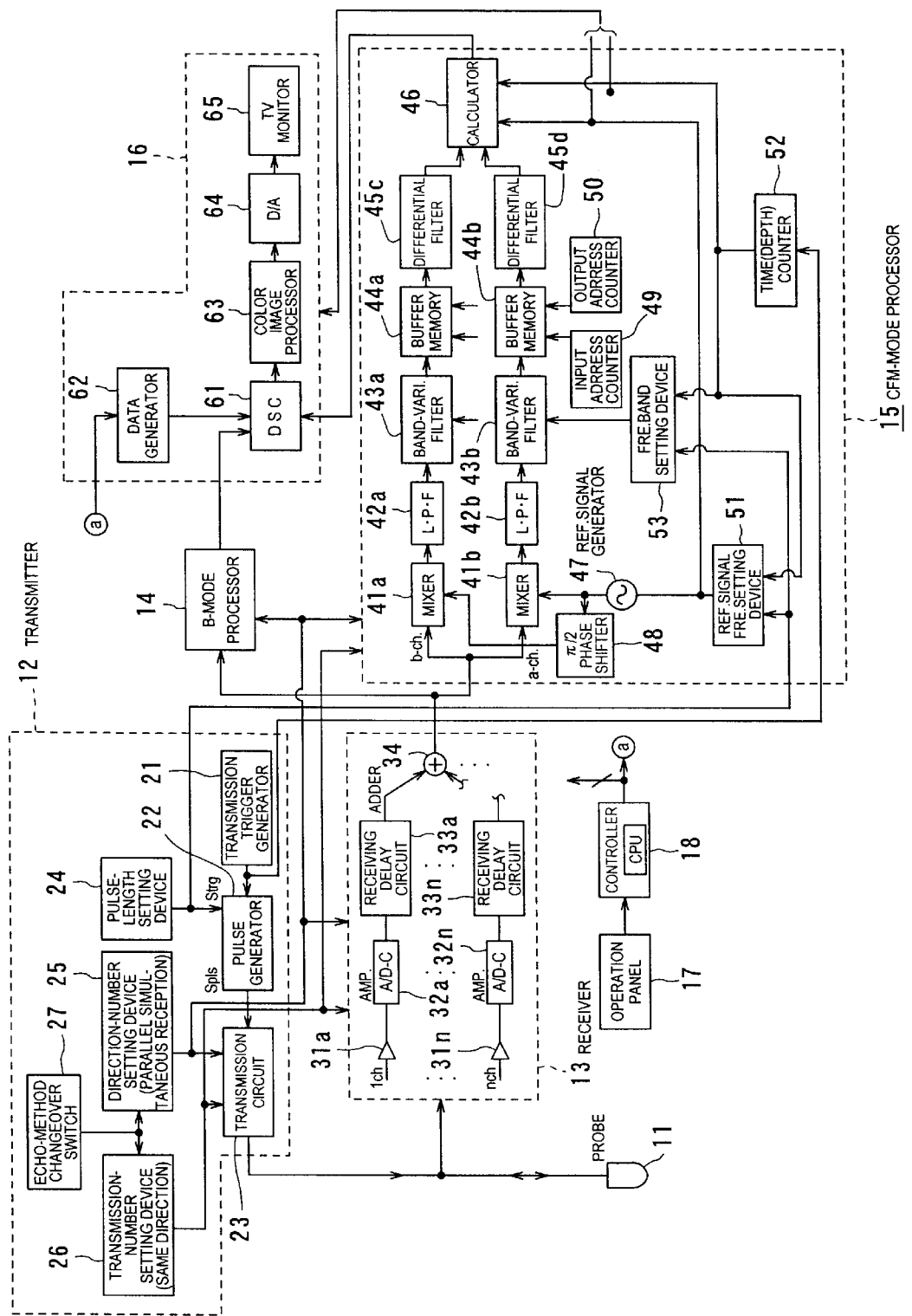
FIG. 34 shows in block form a diagnostic ultrasound apparatus according to a fifth modification of the tenth embodiment, wherein a differentiator is incorporated as a clutter-component removing filter.
Figure 35:
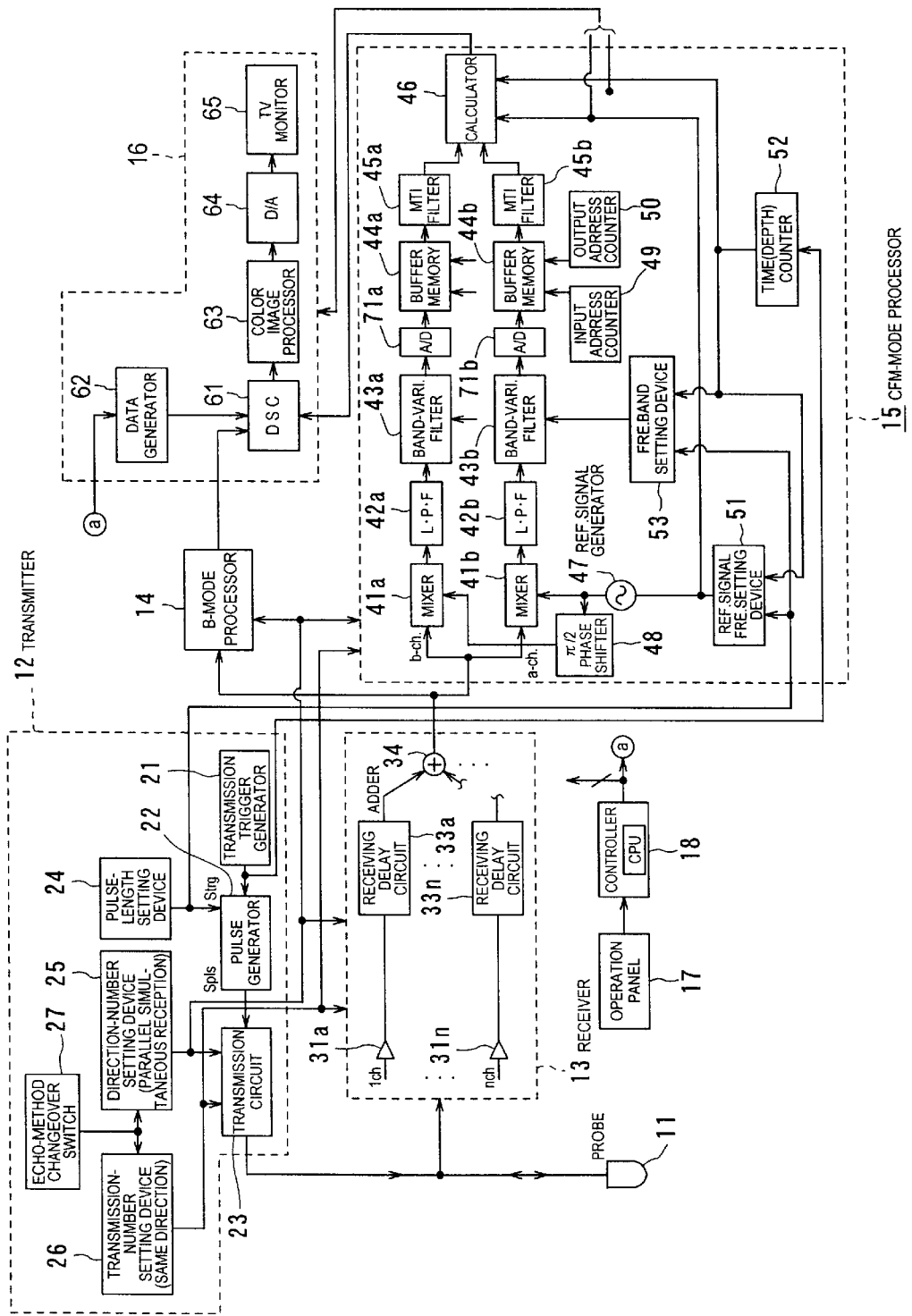
FIG. 35 is a block diagram showing an analog type of diagnostic ultrasound apparatus according to a sixth modification of the tenth embodiment.

A fifth modification is concerned with a filter that removes clutter components. The foregoing CFM-mode processor 15 uses MTI filters 45*a* and 45*b* to remove clutter components. The MTI filters functionally operate as highpass filters (HPF). As an alternative for the MTI filters, a differential filter can be used. FIG. 34 shows an example of the apparatus where differential filters 45*c* and 45*d* are incorporated therein. As the differential technique is used, a transient response phenomenon will not occur, unlike ordinary HPFs. Therefore, the number of times of transmitting an ultrasound pulse in the same raster direction can be lowered by an amount saved by using the differential filters 45*c* and 45*d,* increasing the number of frames per sec., thus increasing the temporal resolution (realtime performance). Practically, at least two times of transmission in the same direction is enough to obtain power data and at least three times of transmission is enough to obtain velocity data.

(Sixth Modification)

A sixth modification is related to a configuration in which A/D converters are inserted in the CFM-mode processor 15, i.e., an analog type of receiving processing system.

In the second embodiment and its modifications, the circuitry of the receiving processing system described so far have adopted a configuration known as a "digital type," where, for example, as shown in FIG. 17, the A/D converters 32*a* (to 32*n*) are placed immediately after the pre-amplifiers 31*a* (to 31*n*) of the receiver 13, thus making it possible to execute reception processing thereafter in the form of digital signals. In contrast, in a receiving processing system of this modification shown in FIG. 35, two A/D converters 71*a* and 71*b* are inserted between the band-variable filters 43*a* and 43*b* and the buffer memories 44*a* and 44*b* in the CFM-mode processor 15, channel by channel. This configuration reduces the number of A/D converters.

Figure 36:
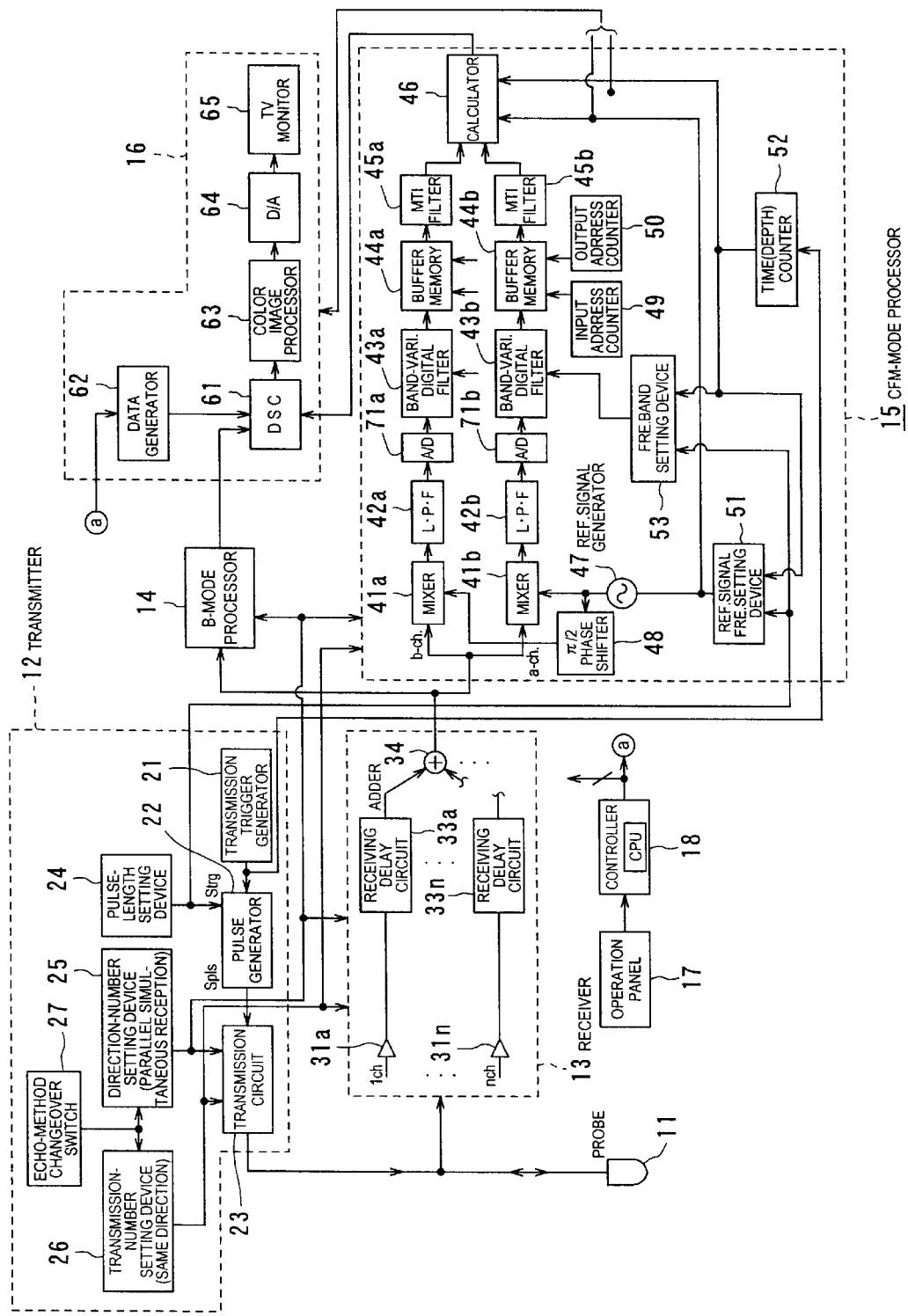
FIG. 36 is a block diagram showing another analog type of diagnostic ultrasound apparatus.

The A/D converters 71*a* and 71*b* may be inserted, as shown in FIG. 36, between the LPFs 42*a* and 42*b* of the quadrature phase detector and the band-variable filters 43*a* and 43*b*, channel by channel. In this case, the filters 43*a* and 43*b* can be constructed as digital type of filters. This provides higher resistance against changes in time, changes in temperature, and the like, as well as a stable filtering characteristic.

The correspondence to the apparatus configuration in FIG. 17 that is a representative of the detailed embodiments will now be described. The probe 11, transmitter 12, receiver 13, and controller 18 constitutes scanning means. The B-mode processor 14; the mixers 41*a* and 41*b*, LPFs 42*a* and 42*b*, band-variable filters 43*a* and 43*b*, buffer memories 44*a* and 44*b*, MTI filters 45*a* and 45*b*, reference signal generator 47, $\pi/2$ phase shifter 48, reference signal frequency setting device 51, time counter 52, and frequency band setting device 53 all placed in the CFM-mode processor 15; the pulse-length setting device 24, direction-number setting device 25, transmission-number setting device 26 all placed in the transmitter 12; and the controller 18 constitute first signal processing means. Further, the display system 16 and the controller 18 corresponds to display means. Still further, the calculator 46, reference signal frequency setting device 51, time counter 52 all placed in the CFM-mode processor 15; the transmission trigger generator 21 and pulse-length setting device 24 all placed in the transmitter 12; and the controller 18 constitute first signal processing means.

Moreover, the present invention is not limited to the foregoing embodiments, and can be practiced into various deformations and combinations without departing from the gist of the present invention.

Figure 37:
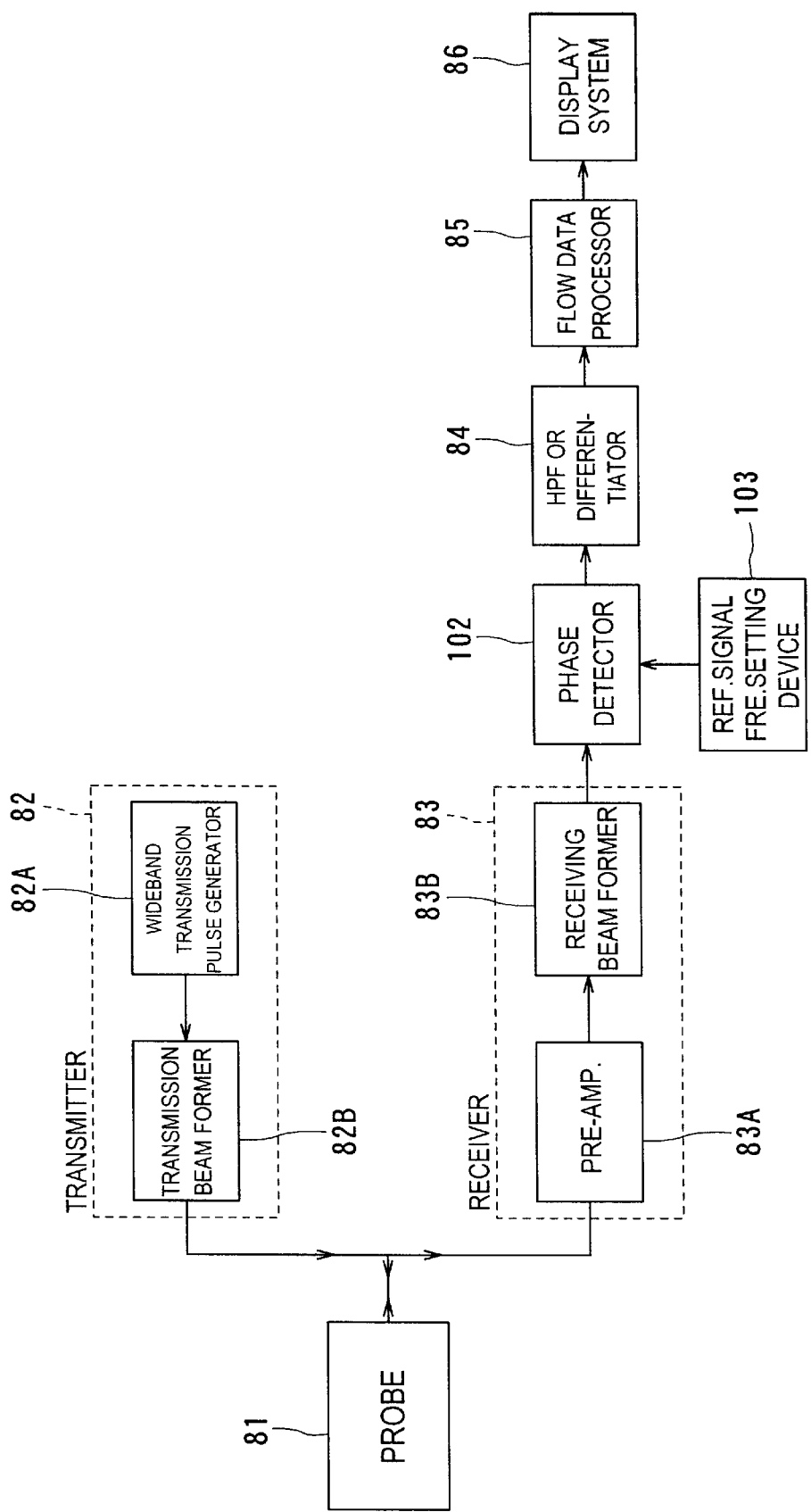
FIG. 37 is a block diagram a diagnostic ultrasound apparatus according to another modification.
Figure 38:
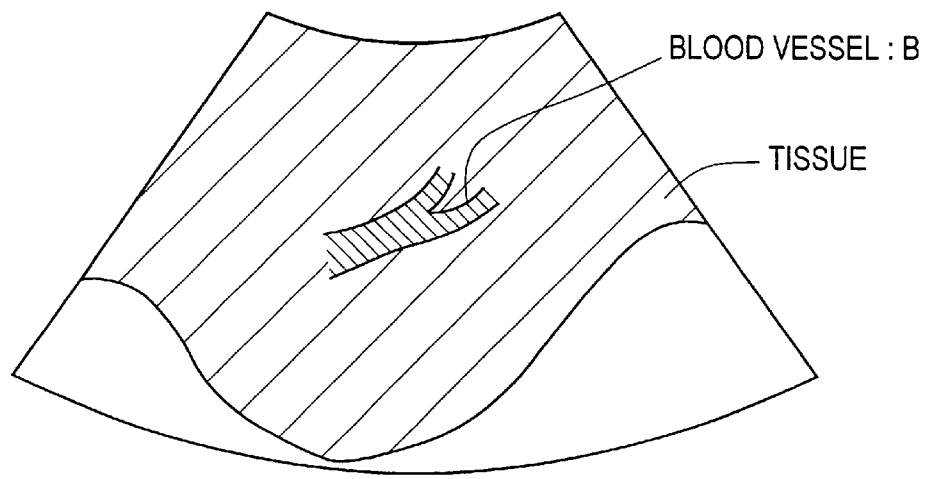
FIG. 38 shows images for explaining drawbacks of the conventional blood flow imaging.
Figure 38:
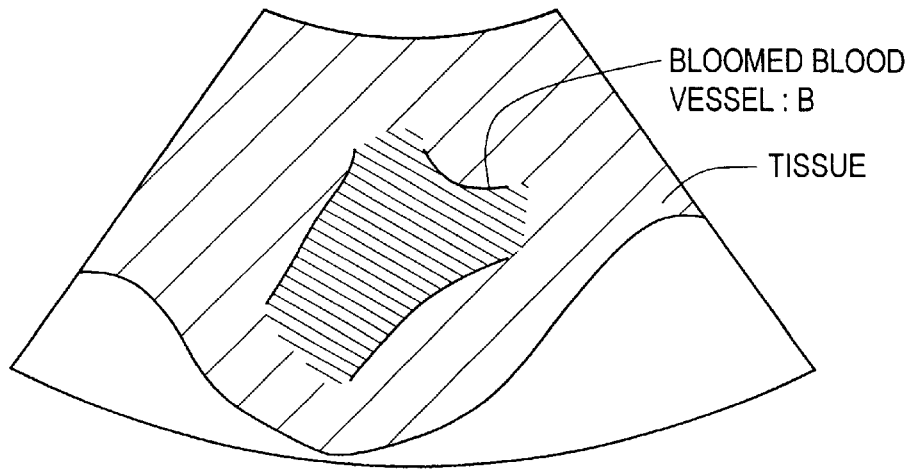

For example, as concerning the apparatus configuration, in the configuration of FIG. 1 operated in the "high-resolution flow mode," a quadrature phase detector 102 can be inserted between the HPF or differentiator 84 and the receiver 83, as shown in FIG. 37. This detector 102 produces a received signal into a base-band signal, detects Doppler data trains of Doppler signals, and performs highpass filtering or differential processing with the data trains, so that signals (clutter components) are removed from tissue and a blood flow image is displayed. In this case, preferably, the frequency of a reference signal used in the detector 102 is adjusted depending on the depth in each raster direction.

Still, in the configurations of the first to seventh embodiments in which the "high-resolution flow mode" is used, the sound pressure level of a wideband ultrasound pulse may be set at an amount that enables not merely a contrast agent to collapse but also an echo signal to include an echo component resulting from the collapse of the contrast agent. Further, the sound pressure level of a wideband ultrasound pulse may be set at an amount that enables not merely irregular oscillations to occur, without collapsing a contrast agent, but also an echo signal to include an echo component resulting from the irregular oscillations of the contrast agent. In this case, the band characteristic of a filter passing desired frequency components of an echo signal may be set at every depth in each raster direction, in relation to at least one of the fundamental component and a harmonic component of an ultrasound pulse.

Further, in the configurations of the first to seventh embodiments practiced in the "high-resolution flow mode," the wide dynamic range capable of processing without saturation the power of echo components resulting from a contrast agent, which has been described in the tenth embodiment, may be adopted.

Further, in the foregoing embodiments and modifications, by way of example, the wideband transmission ultrasound pulse is expressed by using the number of burst waves. Since the wideband cannot be expressed by the number of burst waves, unless the envelope of a transmission pulse is rectangular, a fractional bandwidth at −6 dB or an wave-ranging length at −6 dB can be used to define the wideband, instead. Alternatively, as one of other definition methods, the number of burst waves="not less than 3" can be used for such definition.

Further, in the case of the foregoing embodiments and modifications, pieces of information including blood flow velocities, spectrum dispersions, and Doppler signal power amounts are calculated from Doppler signals and displayed together with a tomogram. Alternatively, only a desired piece of information among them can be displayed directly in an appropriate mode.

As described above, the foregoing embodiments provide a wide variety of advantages as follows.

First, a blood flow is provided as an image showing the luminance or power of echo signals, thus detecting fine blood flows and/or blood flowing at slower speeds in a steadier manner compared to the conventional ordinary CFM image, thus providing blood flow images finely indicative of the presence of blood flow.

Second, the number of burst waves is less than 3, particularly one wave in the most appropriate condition, so that a wideband transmission pulse is established. Therefore, there can be displayed a blood flow image having no or almost no blooming and a higher spatial resolution. Compared to the conventional way, diagnostic performance is noticeably increased.

A third advantage is as follows. Since the number of burst waves is set to a wideband wave, a maximum sensitivity frequency and a frequency band of an echo signal are changed at each depth due to the frequency-dependence attenuation. Specifically, the deeper the depth, the lower the maximum sensitivity frequency and the narrower the reception frequency band. According to the invention, however, various types of correction are performed so that such fluctuations are corrected, therefore the S/N is remarkably increased. Additionally, the clutter removal effect, sensitivity, and range resolution are improved, so diagnostic performance is also upgraded.

As a fourth advantage, a dynamic range for display can be widely and changeably set compared to the conventional method. Hence, even if performing the contrast echo method with a contrast agent, a more appropriate display dynamic range can be set. Image data to be displayed is not saturated and full gradations are obtained. Therefore, it is possible to sufficiently display information about the calculated blood flow power, increasing diagnostic performance.

A fifth advantage is that blood flow images of which realtime performance (temporal resolution) is high can be provided, because the number of parallel simultaneous reception beams in conducting the contrast echo method is raised than those in conducting the non-contrast echo method. This allows a rate of detection per unit time to increase largely, which leads to a remarkably improved diagnostic performance. Additionally, for conducting the contrast echo method, the number of transmission times in the same direction is decreased compared to the non-contrast echo method. This also results in blood flow images that are superior in realtime performance, and contributes to an upgraded diagnostic performance on account of a largely increased detection rate.

Thus, blood flow images are provided which represent finely and accurately the presence of blood flow with higher spatial resolutions. Additionally, in comparison with the conventional CFM, there are provided blood flow images whose spatial resolution is higher and S/N is superior, which leads to an improved diagnostic performance. Moreover, in conducting the contrast echo method, there are provided blood flow images or perfusion images that are superior in the spatial resolution, S/N, and frame rate (temporal resolution) and are wider in the dynamic range for display. Thus diagnostic performance can be improved greatly.

Through the present embodiments have been described as above, the present invention is not limited to the foregoing embodiments. The expert will appreciate that it is possible to appropriately alter or modify them based on measures known from the prior art without departing from the scope of the present invention.

What we claim is:

1. A diagnostic ultrasound apparatus comprising:
   a transmitter/receiver configured to repeatedly scan a cross section of an object at intervals by transmitting a wideband ultrasound pulse along each raster on the cross section and receiving an echo signal reflected from the object in response to the transmitted ultrasound pulse;
   a B-mode image processor configured to produce a B-mode image of the cross section from the received echo signal;
   a processor configured to obtain an analytic value of a moving-element signal in the cross section using the received echo signal reflected, each time of the scanning, from each sample point along each raster on the cross section, the analytic value including a power value of the moving-element signal at each sample point on the cross section; and
   an image synthesizer configured to make a two-dimensional image composed of the B-mode image on which the analytic value is two-dimensionally mapped.

2. The diagnostic ultrasound apparatus of claim 1, wherein the processor includes means for performing desired processing for extracting either a change of the moving element and a change in a phase of the echo signal as a Doppler signal on a train of data indicative of the echo signal aligning in the time axis direction corresponding to each sample position on the cross section.

3. The diagnostic ultrasound apparatus of claim 2, wherein the desired processing is for extracting the change of the moving element and is either one of highpass filtering and differential processing.

4. The diagnostic ultrasound apparatus of claim 3, wherein the processor comprises phase detecting means for phase-detecting the echo signal based on a reference signal, reference-signal frequency changing means for changing a frequency of the reference signal according to a depth in each raster direction along which the ultrasound pulse is transmitted on the cross section, and echo signal processing means performing either the highpass filtering and the differential processing on the phase-detected echo signal.

5. The diagnostic ultrasound apparatus of claim 4, wherein the reference-signal frequency changing means change, every depth in each raster direction, the frequency of the reference signal into the highest frequency in detection sensitivity selected from frequency bands of the echo signal at each depth in each raster direction.

6. The diagnostic ultrasound apparatus of claim 3, wherein the processor comprises filtering means for passing a desired frequency component of the echo signal and echo-signal processing means for performing either the highpass filtering and the differential processing on the echo signal filtered by the filtering means.

7. The diagnostic ultrasound apparatus of claim 6, wherein the filtering means is a band-variable filter of which band characteristic in each raster direction along which the ultrasound pulse is transmitted is changeable.

8. The diagnostic ultrasound apparatus of claim 7, wherein the processor comprises band-characteristic changing means for changing a band characteristic of the band-variable filter in agreement with the depth in each raster direction.

9. The diagnostic ultrasound apparatus of claim 8, wherein the band-characteristic changing means change, every depth in each raster direction, the band characteristic into a band characteristic substantially equivalent to a band of the echo signal at each depth in each raster direction.

10. The diagnostic ultrasound apparatus of claim 6, wherein the filter means is a filter trimming the echo signal in agreement with the echo signal changing in a band characteristic due to factors including living-body attenuation of the object.

11. The diagnostic ultrasound apparatus of claim 3, wherein both of the processor and the image synthesizer have a wide dynamic range permitting processing of power of an echo component provided from the processor and attributable to the contrast agent, in conditions where the power is non-saturated.

12. The diagnostic ultrasound apparatus of claim 11, wherein the wide dynamic range is substantially equivalent to a dynamic range for a B-mode tomography.

13. The diagnostic ultrasound apparatus of claim 11, wherein the wide dynamic range has an upper limit assigned to a value in excess of 40 dB and up to 90 dB.

14. The diagnostic ultrasound apparatus of claim 3, wherein the transmitter/receiver, the B-mode image processor, and the processor are configured to carry out a contrast echo technique under which a contrast agent is administered into the object.

15. The diagnostic ultrasound apparatus of claim 14, wherein the two-dimensional image data are composed of data indicative of either luminance information and power information of the echo signal originated from the contrast agent residing in the cross section.

16. The diagnostic ultrasound apparatus of claim 4, wherein the transmitter/receiver comprises means for assigning a sound level of the wideband ultrasound pulse to a value not only at which the contrast agent is able to vanish but also the echo signal includes an echo component caused by vanishing the contrast agent or another value not only at which the contrast agent causes uneven vibrations but also the echo signal includes an echo component caused by the uneven vibrations of the contrast agent.

17. The diagnostic ultrasound apparatus of claim 16, wherein the processor comprises filter means for passing a desired frequency component of the echo signal and setting means for setting a band characteristic of the filter means in agreement with each depth in each raster along which the ultrasound pulse is transmitted, in relation to at least one of a fundamental component and a harmonic component of the ultrasound pulse.

18. The diagnostic ultrasound apparatus of claim 1, wherein the ultrasound pulse is identical in a frequency characteristic of the wideband to an ultrasound pulse used for obtaining a tomographic image based on a B-mode imaging.

19. The diagnostic ultrasound apparatus of claim 18, wherein the ultrasound pulse is composed of one wave in a pulse length.

20. The diagnostic ultrasound apparatus of claim 18, wherein the transmitter/receiver has wideband setting means for setting the ultrasound pulse of which number of bust waves is less than three, as the wideband ultrasound pulse.

21. The diagnostic ultrasound apparatus of claim 18, wherein the transmitter/receiver has wideband setting means for setting the ultrasound pulse of which fractional bandwidth at −6 dB is 30 percent or more, as the wideband ultrasound pulse.

22. The diagnostic ultrasound apparatus of claim 18, wherein the transmitter/receiver has wideband setting means for setting the ultrasound pulse of which wave train at −6 dB is less than three waves, as the wideband ultrasound pulse.

23. The diagnostic ultrasound apparatus of claim 1, further comprising a unit to obtain image data based on a display mode conventionally used, and a unit to command switchovers between a display mode depending on the processor and a further display mode conventionally used.

24. The diagnostic ultrasound apparatus of claim 23, wherein the further display mode conventionally used is a combination mode of a B-mode and a CFM mode.

25. The diagnostic ultrasound apparatus of claim 1, further comprising
    a unit to selectively command a contrast echo technique of imaging the cross section with the use of a contrast agent administered into the object and a non-contrast echo technique of imaging the cross section with no use of a contrast agent, and
    a unit to switch over at least one of transmission of the ultrasound pulse and processing of the echo signal into an optimum condition, every echo technique, in relation to the contrast echo technique or the non-contrast echo technique commanded by the commanding unit.

26. The diagnostic ultrasound apparatus of claim 25, wherein the switching-over unit is configured to switch over the processing so that, when the contrast echo technique is selected, the number of directions for parallel simultaneous reception of the echo signal in relation to each raster along which the ultrasound pulse is transmitted is increased compared to the non-contrast echo technique.

27. The diagnostic ultrasound apparatus of claim 25, wherein the switching-over unit is configured to switch over the number of times of transmission and reception so that, when the contrast echo technique is selected, the number of times of transmission and reception along the same raster on the cross section is decreased compared to the non-contrast echo technique.

28. The diagnostic ultrasound apparatus of claim 1, wherein the processor comprises means for phase-detecting the echo signal based on a reference signal, and velocity calculating means for calculating information including a movement velocity and a Doppler frequency of the moving element based on the reference signal, the apparatus further comprising a unit to change a frequency of the reference signal in accordance with each depth in each raster along which the ultrasound pulse is transmitted.

29. The diagnostic ultrasound apparatus of claim 28, wherein the image synthesizer comprises means for displaying at least one of the Doppler frequency and the velocity, the Doppler frequency being displayed with an aliasing frequency thereof, and the velocity being displayed with a plurality of aliasing velocities associated with changing the reference frequency according to each depth.

30. The diagnostic ultrasound apparatus of claim 29, wherein the image synthesizer is configured to display the velocity with a color bar according to a mode under which the same hue is assigned to the same velocity, the color bar virtually or substantially having an axis of the Doppler frequency and a further axis of the depth, thereby the velocity corresponding to the Doppler frequency at each depth is two-dimensionally displayed on the color bar.

31. The diagnostic ultrasound apparatus of claim 29, wherein the image synthesizer is configured to display the velocity with a color bar according to a mode under which the same hue is assigned to the same velocity, the color bar virtually or substantially having an axis of the velocity and a further axis of the depth, thereby an aliasing velocity at each depth is two-dimensionally displayed on the color bar.

32. The diagnostic ultrasound apparatus of claim 1, wherein the image synthesizer is configured to present the two-dimensional image composed of the B-mode image on which the power value is two-dimensionally mapped.

33. The diagnostic ultrasound apparatus of claim 1, wherein the processor includes means for performing auto-correlation processing on a train of data indicating the moving-element signal aligning in a time axis direction corresponding to each sample point of the cross section, thereby a frequency of the train of data being analyzed to obtain the analytic value.

34. A diagnostic ultrasound apparatus comprising:

a transmitter/receiver configured to repeatedly scan a cross section of an object at intervals by transmitting a wideband ultrasound pulse along each raster on the cross section and receiving an echo signal reflected from the object in response to the transmitted ultrasound pulse;

a B-mode image processor configured to produce a B-mode image of the cross section from the received echo signal;

a processor configured to obtain analytic values including at least one of a Doppler frequency and a frequency dispersion based on the received echo signal corresponding to the wideband ultrasound pulse, using an MTI filter and an auto-correlater; and an image synthesizer configured to make a two-dimensional image composed of the B-mode image on which the analytic values are two-dimensionally mapped.

35. A method for ultrasound imaging comprising the steps of:

scanning a cross section of an object by transmitting a wideband ultrasound pulse along each raster on the cross section and receiving an echo signal reflected from the object in response to the transmitted ultrasound pulse, the scanning being repeatedly carried out at intervals with the raster changed;

producing a B-mode image of the cross section from the received echo signal and in parallel, obtaining an analytic value of a moving-element signal in the cross section using the received echo signal reflected, each time of the scanning, from each sample point along each raster on the cross section, the analytic value including a power value of the moving-element signal at each sample point on the cross section; and making a two-dimensional image composed of the B-mode image on which the analytic value is two-dimensionally mapped.

36. A method for ultrasound imaging comprising the steps of:

scanning a cross section of an object by transmitting a wideband ultrasound pulse along each raster on the cross section and receiving an echo signal reflected from the object in response to the transmitted ultrasound pulse, the scanning being repeatedly carried out at intervals;

producing a B-mode image of the cross section from the received echo signal and in parallel, obtaining analytic values including at least one of a Doppler frequency and a frequency dispersion based on the received echo signal corresponding to the wideband ultrasound pulse, using an MTI filter and an auto-correlater; and making a two-dimensional image composed of the B-mode image on which the analytic values are two-dimensionally mapped.

* * * * *